US010117913B2

(12) United States Patent
Shellito et al.

(10) Patent No.: US 10,117,913 B2
(45) Date of Patent: Nov. 6, 2018

(54) **ANTIGENS OF *PNEUMOCYSTIS MURINA* AND USES THEREOF**

(71) Applicants: Board of Supervisors of Louisiana State University and Agricultural and Mechanical College, Baton Rouge, LA (US); THE UNIVERSITY OF NEW ORLEANS, New Orleans, LA (US)

(72) Inventors: Judd E. Shellito, New Orleans, LA (US); Alistair John Ramsay, New Orleans, LA (US); David A. Welsh, New Orleans, LA (US); Sanbao Ruan, New Orleans, LA (US); Yang Cai, New Orleans, LA (US)

(73) Assignees: BOARD OF SUPERVISORS OF LOUISIANA STATE UNIVERSITY, Baton Rouge, LA (US); THE UNIVERSITY OF NEW ORLEANS, New Orleans, LA (US)

( * ) Notice: Subject to any disclaimer, the term of this patent is extended or adjusted under 35 U.S.C. 154(b) by 0 days.

(21) Appl. No.: 15/305,190

(22) PCT Filed: May 4, 2015

(86) PCT No.: PCT/US2015/029064
§ 371 (c)(1),
(2) Date: Oct. 19, 2016

(87) PCT Pub. No.: WO2015/171505
PCT Pub. Date: Nov. 12, 2015

(65) Prior Publication Data

US 2017/0042988 A1 Feb. 16, 2017

Related U.S. Application Data

(60) Provisional application No. 61/988,601, filed on May 5, 2014.

(51) Int. Cl.
*A61K 39/40* (2006.01)
*A61K 39/00* (2006.01)
(Continued)

(52) U.S. Cl.
CPC .......... *A61K 39/0002* (2013.01); *A61K 39/00* (2013.01); *C07K 16/40* (2013.01); *C12N 9/48* (2013.01); *A61K 2039/55566* (2013.01)

(58) Field of Classification Search
CPC ........ A61K 39/40; A61K 39/02; A61K 39/00; C07K 14/315; C07K 14/37
(Continued)

(56) References Cited

U.S. PATENT DOCUMENTS

2008/0171053 A1* 7/2008 Gigliotti ............ C07K 14/3156 424/165.1
2013/0058891 A1 3/2013 Kolls et al.

OTHER PUBLICATIONS

International Search Report for PCT/US2015/029064 dated Nov. 2, 2015.

(Continued)

*Primary Examiner* — Jana A Hines
(74) *Attorney, Agent, or Firm* — Baker Donelson

(57) ABSTRACT

A surface protein of the murine fungal pathogen *Pneumocystis murina* can be used to generate an immune response in a recipient animal or human that provides prophylactic protection and an anti-fungal activity in subjects already infected with a *Pneumocystis* species. Further, the disclosure provides novel polypeptides or peptides derived from the *P. murina* surface protein Surface Peptidase 1 (SPD-1) that are useful, alone or in combination with the SPD-1 polypeptide, in compositions and methods for the generation of an anti-*Pneumocystis* immune reaction by a recipient subject. The compositions and methods of the disclosure provide advantageous alternatives to available immunogenic deter- (Continued)

minants for the treatment or prevention of fungal pneumonia.

6 Claims, 17 Drawing Sheets

Specification includes a Sequence Listing.

(51) Int. Cl.
*C07K 16/40* (2006.01)
*C12N 9/48* (2006.01)

(58) Field of Classification Search
USPC ........... 424/165.1, 190.1; 530/324, 326, 327, 530/328, 329, 350
See application file for complete search history.

(56) References Cited

OTHER PUBLICATIONS

UniProtKB accession No. M7NLW2_PNEMU, sequence.
Zheng, et al., "CD4+ T cell-independent DNA vaccination against opportunistic infections", Journal of Clinical Investigation, Dec. 2005, vol. 115, No. 12, 3536-3544.
Zheng, et al., "Novel Pneumocystis Antigen Discovery Using Fungal Surface Proteomics", Infection and Immunity, Jun. 2014, vol. 82, No. 6, pp. 2417-2423.

* cited by examiner

ANTIGENS OF *PNEUMOCYSTIS MURINA* AND USES THEREOF

CROSS-REFERENCE TO RELATED APPLICATIONS

This application is the 35 U.S.C. § 371 national stage application of PCT Application No. PCT/US2015/029064, filed May 4, 2015, where the PCT claims priority to and the benefit of U.S. Provisional Application 61/988,601 titled "ANTIGENS OF *PNEUMOCYSTIS* AND USES THEREOF" filed May 5, 2014, both of which are herein incorporated by reference in their entirety.

STATEMENT REGARDING FEDERALLY SPONSORED RESEARCH OR DEVELOPMENT

This invention was made with government support under Grant No. HL076100 awarded by the National Institutes of Health. The government has certain rights in the invention.

FIELD OF THE DISCLOSURE

The present disclosure relates generally to *Pneumocystis murina* polypeptides suitable for use in therapeutically inducing an immune response in a subject susceptible to *Pneumocystis* pneumonia encoded therein. This disclosure further relates to nucleic acids encoding immunogenic peptides of *P. murina* and immunogenic compositions comprising the peptides

SEQUENCE LISTING

The present disclosure includes a sequence listing incorporated herein by reference in its entirety.

BACKGROUND

*Pneumocystis* has been identified in every mammalian species studied thus far, and genetic analysis has established that each host species harbors a distinct *Pneumocystis* species. For example, man is the primary host for *Pneumocystis jirovecii* (Stringer et al., (2002) *Emerg. Infect. Dis.* 8: 891-896), and the mouse is the primary host of *Pneumocystis murina* (Redhead et al. (2006) *J. Eukaryot. Microbiol.*).

*Pneumocystis jirovecii* is an opportunistic pathogen with a tropism for the alveoli of the lung. The presence of *Pneumocystis* without clinical signs or symptoms of infection, often referred to as colonization, has been documented in humans. In healthy, immunocompetent individuals, the colonized state tends to be transient. However, in individuals with a weakened immune system, colonization is much more persistent (Morris et al., (2008) *J. Infect. Dis.* 198: 1345-1352; Nevez et al., (1999) *J. Eukaryot. Microbiol.*; Morris et al., (2004) *Am. J. Respir. Crit. Care Med.* 170: 408-413). Subsequently, individuals with weakened immune system have increased susceptibility to *Pneumocystis* pneumonia (PCP), a fungal infection of the lungs caused by *Pneumocystis jirovecii*. As the length of survival of HIV, cancer, transplant, and other immunosuppressed patients has increased, so has the prevalence of PCP in the population.

HIV (human immunodeficiency virus) is a viral infection that leads to the progressive failure of the immune system, allowing life-threatening infections and diseases to thrive. In HIV-infected individuals, pulmonary infection with *Pneumocystis* remains the most common opportunistic infection. Clinically, PCP in HIV-infected individuals is characterized by progressive dyspnea, a non-productive cough or cough productive of clear sputum, malaise and low-grade fever. Prior to highly active anti-retroviral therapy (HAART), PCP was the most common cause of death among HIV-infected individuals. Although HAART has helped control PCP in HIV-infected individuals, there continues to be a significant mortality associated with *Pneumocystis* infection (Morris et al., (2003) *AIDS* 17: 73-80; Jain et al., (2003) *Clin. Infect. Dis.* 36: 1030-1038).

The incidence of PCP in non-HIV individuals has historically been rare; however, the increased clinical use of immunosuppressive and chemotherapeutic agents has resulted in a rise in PCP cases (Sowden et al., (2004) *BMC Infect. Dis.* 4: 42; De Castro et al. Rev. Mal. Respir. 2007). Those most at risk for PCP include bone marrow transplant patients, solid organ transplant patients, and cancer patients (for example those with hematological malignancies). Others at risk include individuals with collagen vascular disease, inflammatory bowel disease, rheumatoid arthritis and Crohn's disease. Clinical symptoms of PCP in these individuals include fever, dry cough, and shortness of breath, and can quickly progress to respiratory failure.

*Pneumocystis* infection is generally treated with antimicrobial agents, such as trimethoprim-sulfamethoxazole. Unfortunately, multiple shortcomings have limited the use and effectiveness of these agents. In particular, the incidence of intolerance to these agents is high due to allergies against the sulfa component of the drug. Additionally, long-term use of antimicrobial agents in *Pneumocystis*-colonized individuals has led to selection for mutations giving rise to drug-resistant strains. Consequently, these shortcomings result in treatment failure and increased mortality (Thomas & Limper, (2007) *Nat. Rev. Microbiol.* 5: 298-308). Collectively, the increasing incidence of *Pneumocystis* infection and the shortcomings associated with current *Pneumocystis* therapies underscore unmet needs for (i) novel primary and adjunctive treatments of infection, and (ii) agents to prevent *Pneumocystis* infection or the development of *Pneumocystis* pneumonia. Such a vaccine therapy may serve this dual purpose.

SUMMARY

Provided are compositions and methods incorporating isolated surface-derived immunogenic peptides of the Surface Peptidase 1 (SPD-1) obtained from the murine-associated fungus *Pneumocystis murina* for use in prophylactic prevention or treatment of *Pneumocystis* pneumonia. One aspect of the disclosure, therefore, encompasses embodiments of an immunogenic composition comprising at least one immunogenic component selected from the group consisting of: (a) an isolated Surface Peptidase 1 (SPD-1) polypeptide of *Pneumocystis murina* and having an amino acid sequence having at least 90% similarity to the sequence according to SEQ ID NO: 1 and (b) at least one immunogenic fragment of an SPD-1 polypeptide of *Pneumocystis murina* wherein said at least one fragment has an amino acid sequence of at least 90% similarity to an amino acid sequence selected from the group consisting of: SEQ ID NOs: 2, 4, 6, 7, and 10-40, and wherein the composition further comprises a pharmaceutically acceptable carrier and is formulated to induce an anti-*Pneumocystis* immune response when administered to an animal or human recipient.

In some embodiments of this aspect of the disclosure, the at least one immunogenic fragment of the SPD-1 polypeptide can have an amino acid sequence selected from SEQ ID NO: 2 and SEQ ID NO: 4.

Another aspect of the disclosure encompasses embodiments of an antibody or fragment thereof that can selectively bind to an antigenic region of *Pneumocystis murina* Surface Peptidase 1 (SPD-1).

Yet another aspect of the disclosure encompasses embodiments of an isolated Surface Peptidase 1 (SPD-1) polypeptide of *Pneumocystis murina* having an amino acid sequence of at least 90% similarity to the sequence according to SEQ ID NO: 1, or an immunogenic fragment thereof.

Still another aspect of the disclosure encompasses embodiments of an isolated nucleic acid having a nucleotide sequence encoding a Surface Peptidase 1 (SPD-1) polypeptide of *Pneumocystis murina*, or an immunogenic fragment thereof.

Still yet another aspect of the disclosure encompasses embodiments of a method of generating an immune response to a *Pneumocystis* infection in an animal comprising administering to said animal an immunogenic composition comprising at least one immunogenic component selected from the group consisting of: (a) an isolated Surface Peptidase 1 (SPD-1) polypeptide of *Pneumocystis murina* and having an amino acid sequence having at least 90% similarity to the sequence according to SEQ ID NO: 1 and (b) at least one immunogenic fragment of an SPD-1 polypeptide of *Pneumocystis murina* wherein said at least one fragment has an amino acid sequence of at least 90% similarity to an amino acid sequence selected from the group consisting of: SEQ ID NOs: 2, 4, 6, 7, and 10-40, and wherein the composition further comprises a pharmaceutically acceptable carrier and is formulated to induce an anti-*Pneumocystis* immune response when administered to an animal or human recipient.

In some embodiments of this aspect of the disclosure, the *Pneumocystis* infection in a human and the infectious agent can be *P. jirovecii*.

Yet another aspect of the disclosure encompasses embodiments of a kit comprising a container containing a therapeutic amount of an immunogenic composition according to claim 1 and instructions directing the use of the composition in generating an immune response in a recipient animal or human.

BRIEF DESCRIPTION OF THE DRAWINGS

Aspects of the present disclosure will be more readily appreciated upon review of the detailed description of its various embodiments, described below, when taken in conjunction with the accompanying drawings. The drawings are described in greater detail in the description and examples below.

FIG. 2A is a graph illustrating that sera from mice (CD4 intact) immunized with N230+adjuvant contain antibodies that bind to N230. "+Control" is sera from mice previously infected with *P. murina.*

FIG. 2B is a graph illustrating that sera from mice (CD4 intact) immunized with C450 (or C450+N230)+adjuvant contain antibodies that bind to C450. "+control" is sera from mice previous infected with *P. murina.*

FIG. 3A is a graph illustrating SPD-1 Elisa, 1 week after PC (N230).

FIG. 3B is a graph illustrating SPD-1 Elisa, 4 week after PC (N230).

FIG. 3C is a graph illustrating SPD-1 Elisa, 6 week after PC (N230).

FIG. 4A is a graph illustrating SPD-1 Elisa, 1 week after PC (C450).

FIG. 4B is a graph illustrating SPD-1 Elisa, 4 weeks after PC (C450).

FIG. 4C is a graph illustrating SPD-1 Elisa, 6 weeks after PC (C450).

FIG. 5A is a graph illustrating SPD-1 Elisa, 10 weeks after PC (N230).

FIG. 5B is a graph illustrating SPD-1 Elisa, 10 weeks after PC (C450).

FIG. 6A is a graph illustrating lung 1 week after PC.

FIG. 6B is a graph illustrating lung 4 weeks after PC.

FIG. 6C is a graph illustrating lung 6 weeks after PC.

FIG. 6D is a graph illustrating lung 10 weeks after PC.

FIG. 7A is a graph illustrating lung 1 week after PC.

FIG. 7B is a graph illustrating lung 4 weeks after PC.

FIG. 7C is a graph illustrating lung 6 weeks after PC.

FIG. 7D is a graph illustrating lung 60 weeks after PC.

FIG. 8A is a graph illustrating spleen 1 week after PC.

FIG. 8B is a graph illustrating spleen 4 weeks after PC.

FIG. 8C is a graph illustrating spleen 6 weeks after PC.

FIG. 8D is a graph illustrating spleen 60 weeks after PC.

FIG. 9A is a graph illustrating spleen 1 week after PC.

FIG. 9B is a graph illustrating spleen 4 weeks after PC.

FIG. 9C is a graph illustrating spleen 6 weeks after PC.

FIG. 9D is a graph illustrating spleen 60 weeks after PC.

FIG. 10A is a graph illustrating SPD-1 1 week after PC.

FIG. 10B is a graph illustrating SPD-1 4 weeks after PC.

FIG. 10C is a graph illustrating SPD-1 6 weeks after PC.

DESCRIPTION OF THE DISCLOSURE

Figure 1:
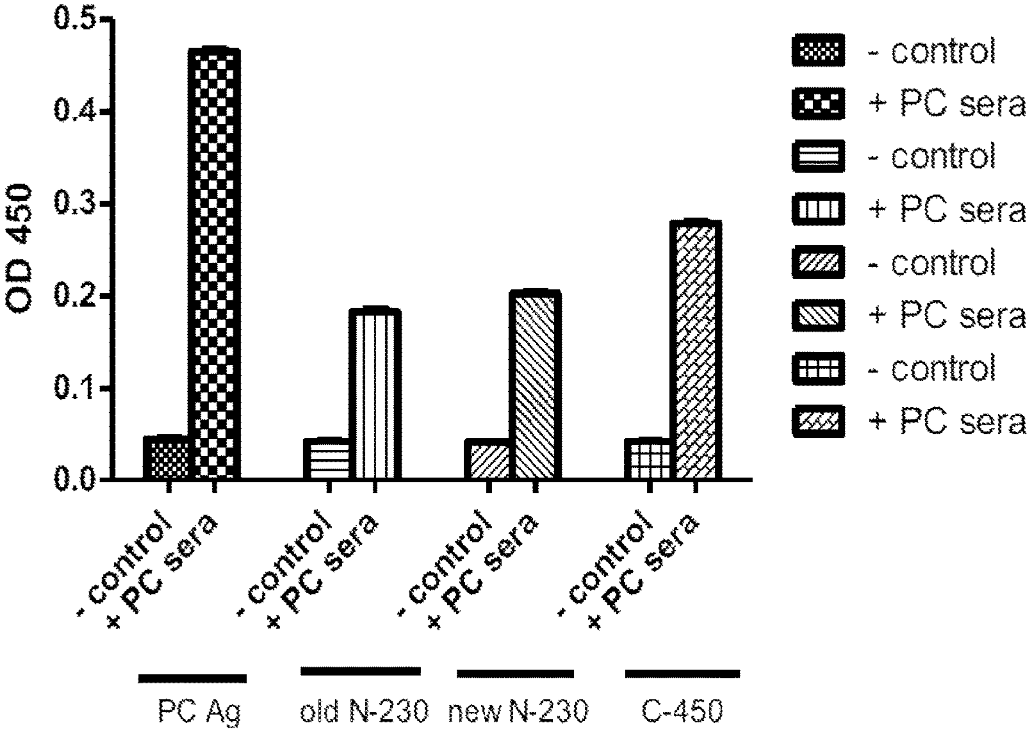
FIG. 1 is a graph illustrating that a "natural" *Pneumocystis* lung infection generates antibodies that recognize *Pneumocystis murina* SPD-1 protein fragments. Sera from mice (CD4 intact) previously infected with *P. murina* contain antibodies that bind to the N230 and C450 protein fragments of SPD-11. "Old" and "new" refer to two separate preparations of N230.
Figure 2A:
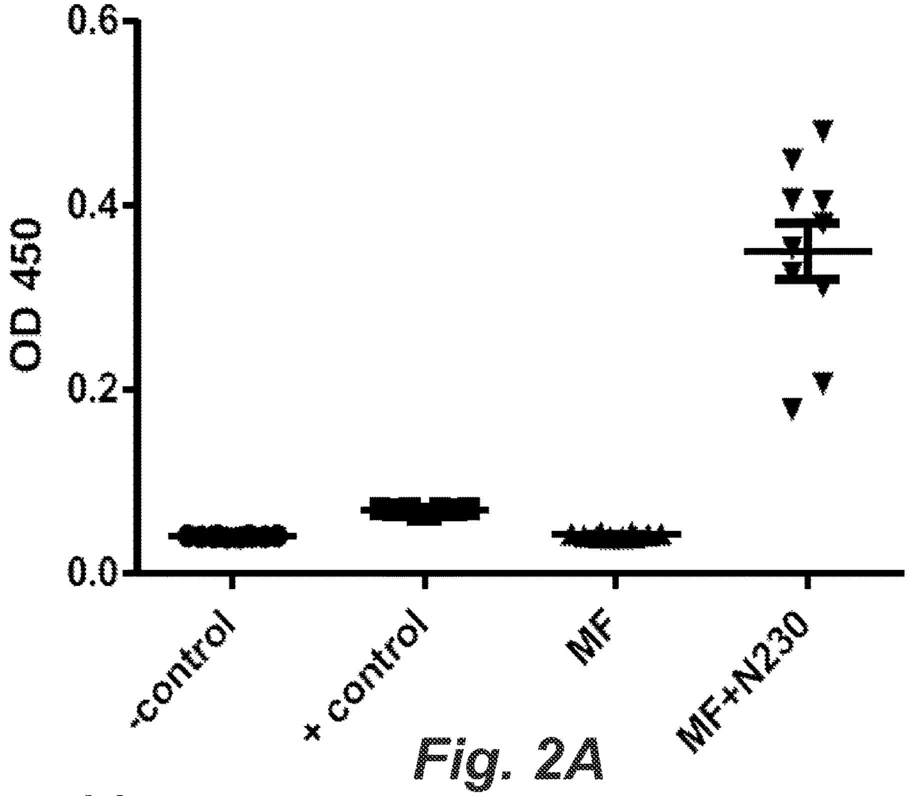
FIGS. 2A and 2B illustrate that immunization generates antibodies against the SPD-1 protein fragments N230 and C450.
Figure 2B:
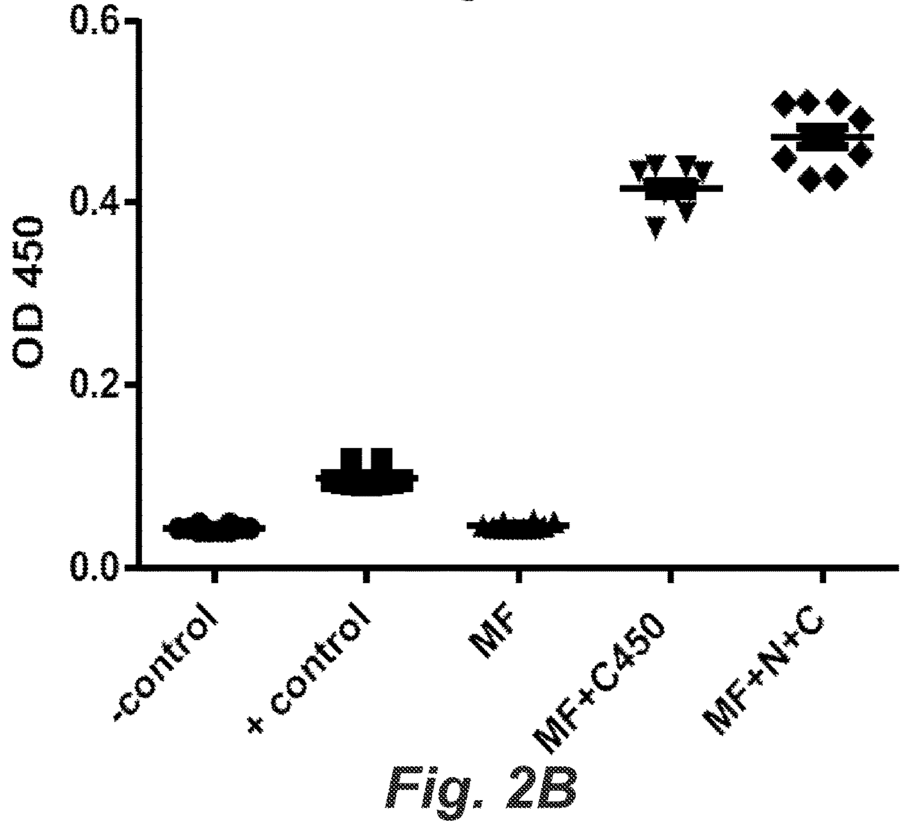
Figure 3A:
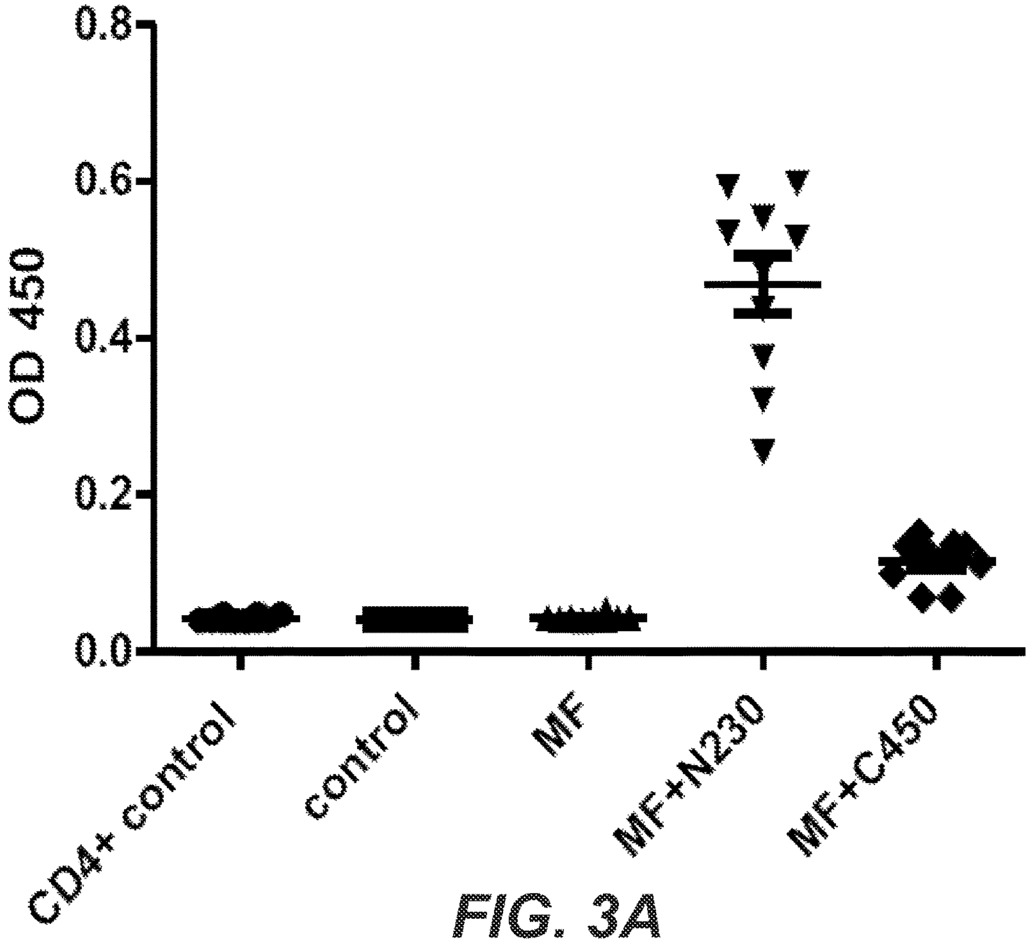
FIGS. 3A-3C show a series of graphs illustrating that immunization-associated antibodies against the SPD-1 protein fragment N230 persist during *Pneumocystis* pneumonia despite CD4 T-cell depletion. Sera from mice (CD4 depleted) that were immunized with N230+adjuvant then infected with *P. murina* contain antibodies that bind to N230. "$CD4^+$ control" is sera from mice previously infected with *P. murina*; 'control' are CD4-depleted & infected mice immunized with saline; 'cMF' are CD4-depleted & infected mice immunized with adjuvant; there is low grade cross reactivity in sera immunized with C450.
Figure 3B:
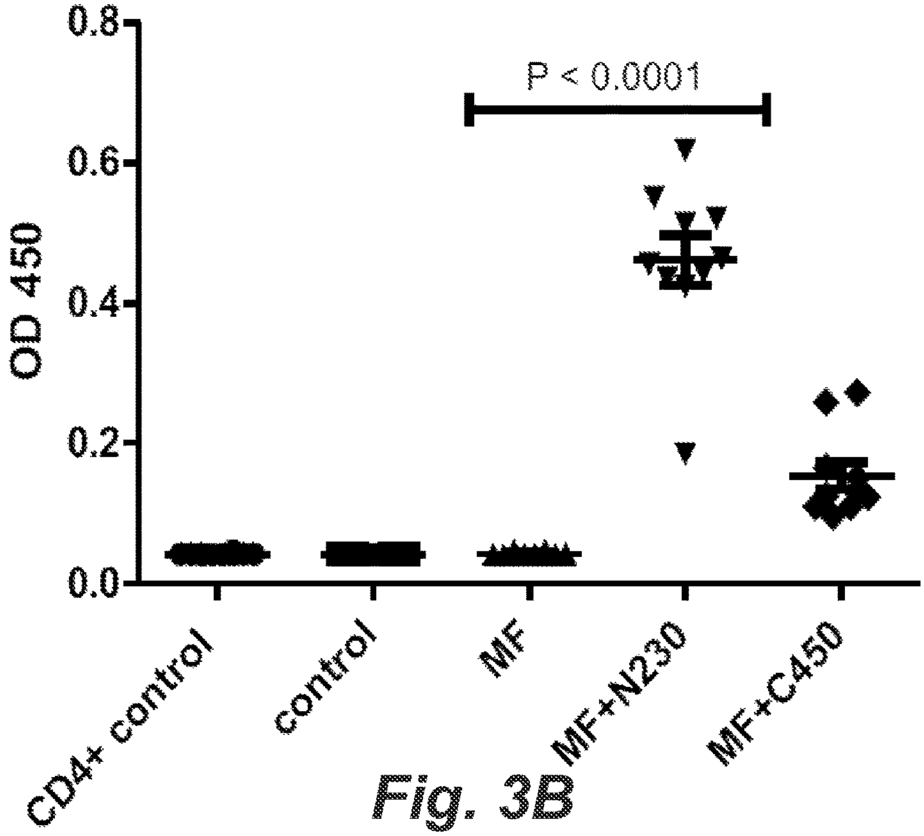
Figure 3C:
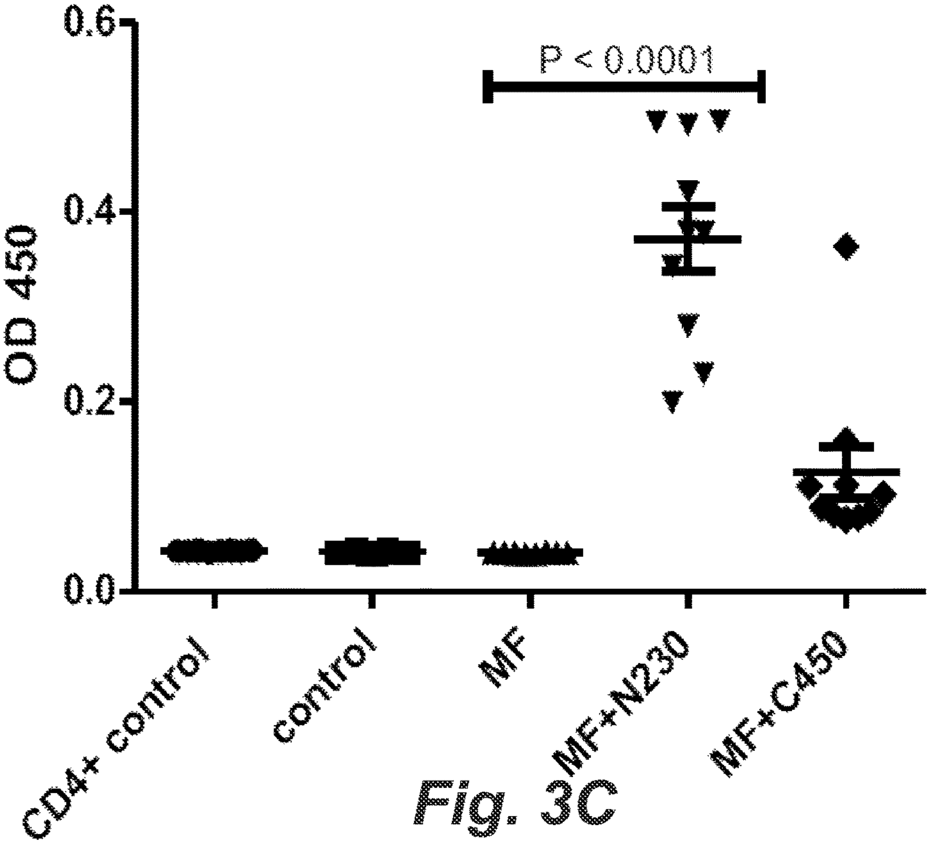
Figure 4A:
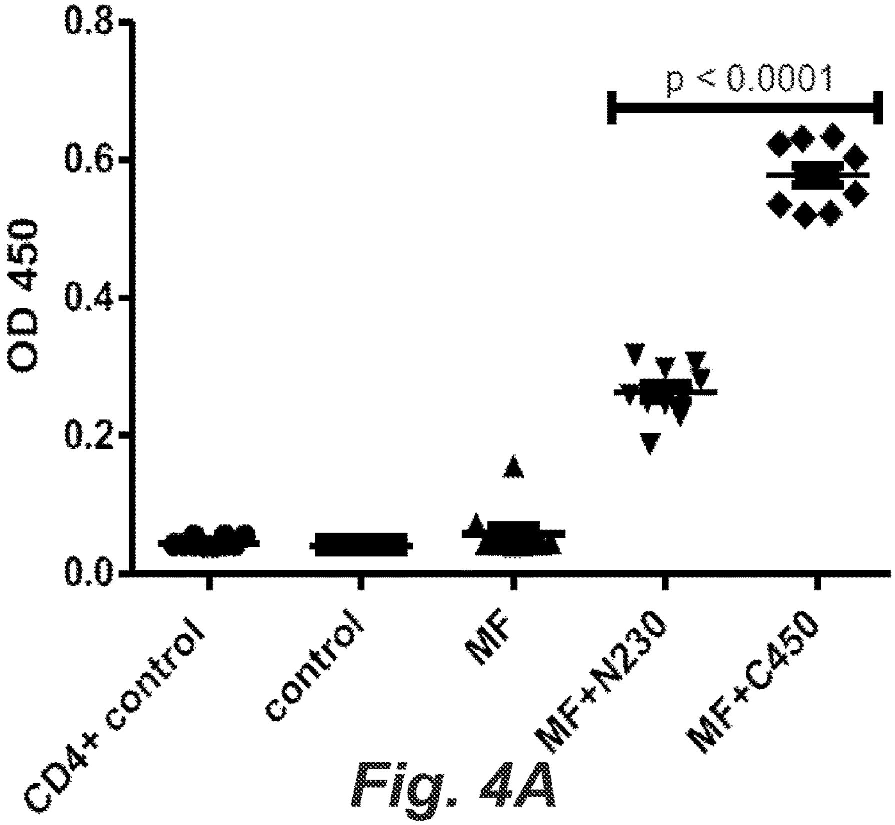
FIGS. 4A-4C is a series of graphs illustrating that immunization-associated antibodies against the SPD-1 protein fragment C450 persist during *Pneumocystis* pneumonia despite CD4 T-cell depletion. Sera from mice (CD4 depleted) immunized with C450+adjuvant then infected with *P. murina* contain antibodies that bind to C450. "CD4+ control" is sera from mice previous infected with *P. murina*; "control" are CD4-depleted & infected mice immunized with saline; 'MF' are CD4-depleted & infected mice immunized with adjuvant; note that there is low grade cross reactivity in sera immunized with N230.
Figure 4B:
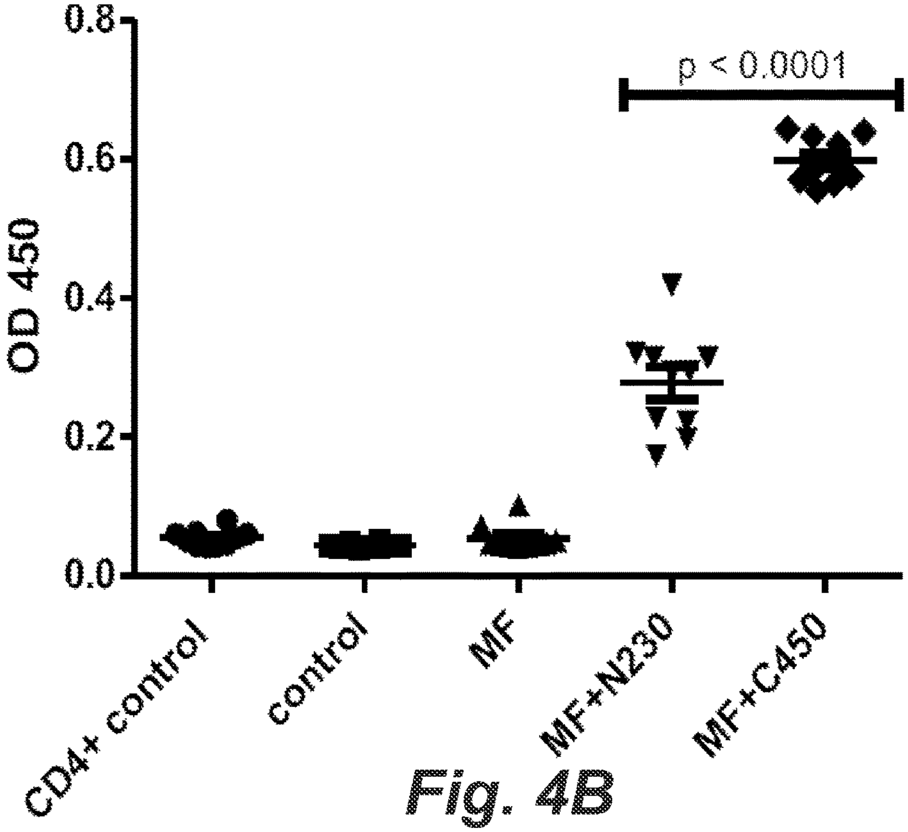
Figure 4C:
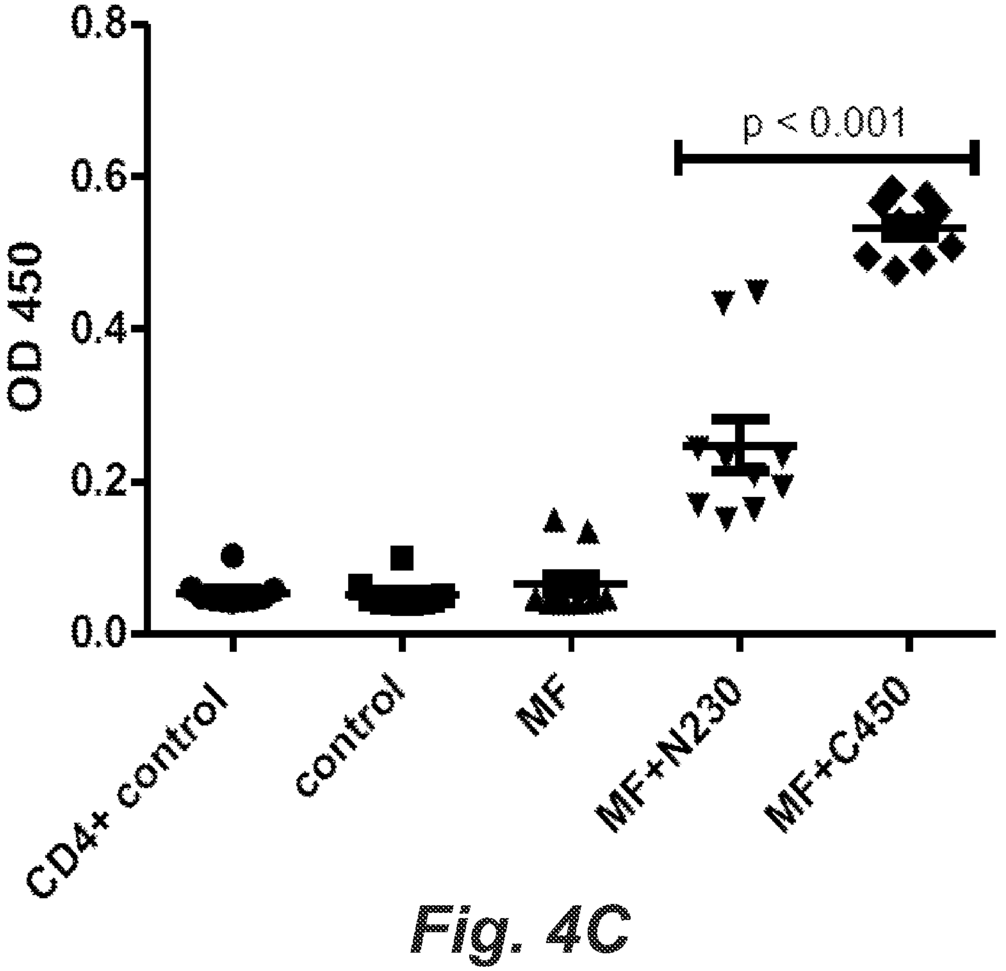
Figure 5A:
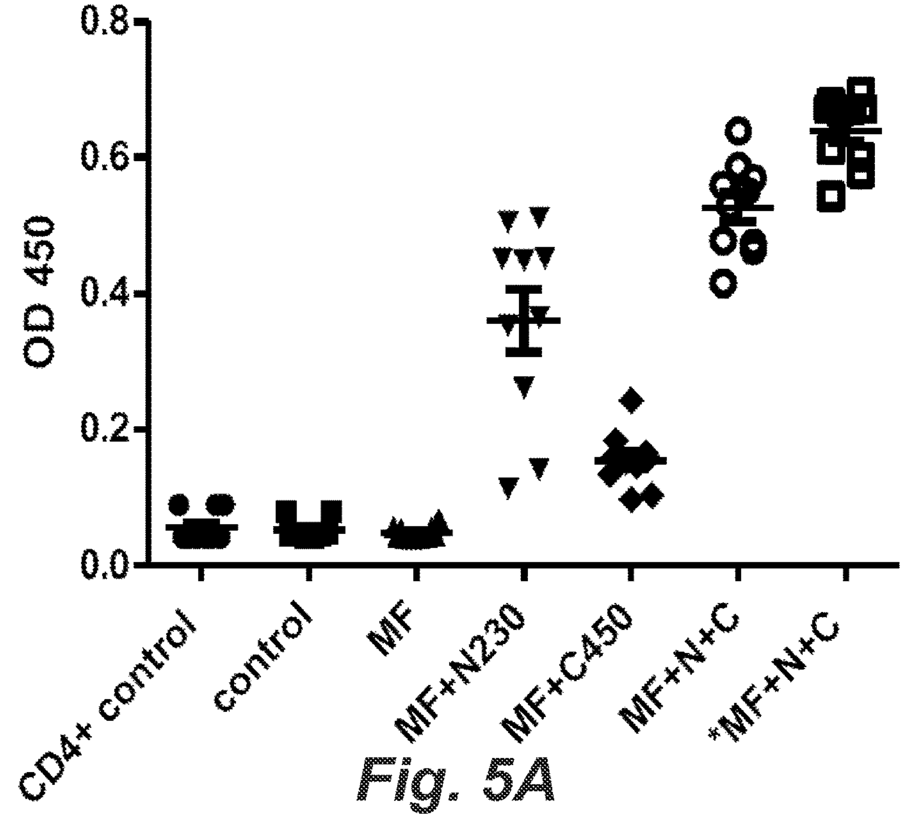
FIGS. 5A and 5B are graphs illustrating that immunization-associated antibodies against the SPD-1 protein fragments persist after *Pneumocystis* pneumonia despite CD4 T-cell depletion. Sera from mice (CD4 depleted) immunized with N230, C450 or both (+adjuvant) then infected with *P. murina* contain antibodies that bind to C450. "CD4+control" is sera from mice previous infected with *P. murina*; "control" are CD4-depleted & infected mice immunized with saline; 'MF' are CD4-depleted & infected mice immunized with adjuvant; note that there is low grade cross reactivity in sera immunized with N230.
Figure 5B:
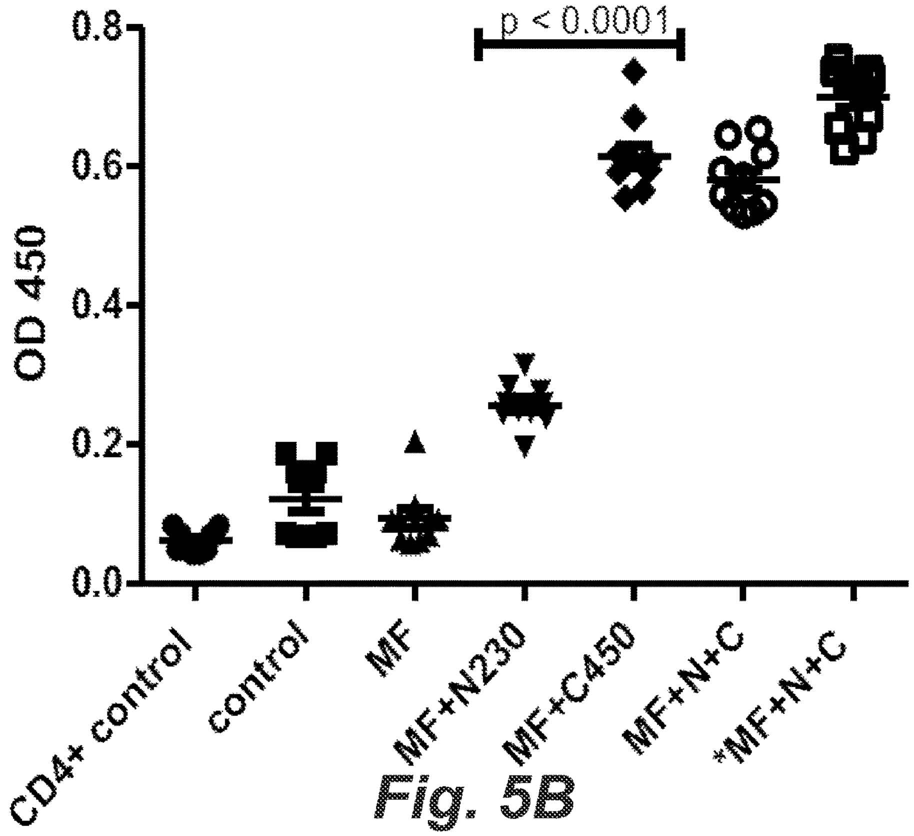
Figure 6A:
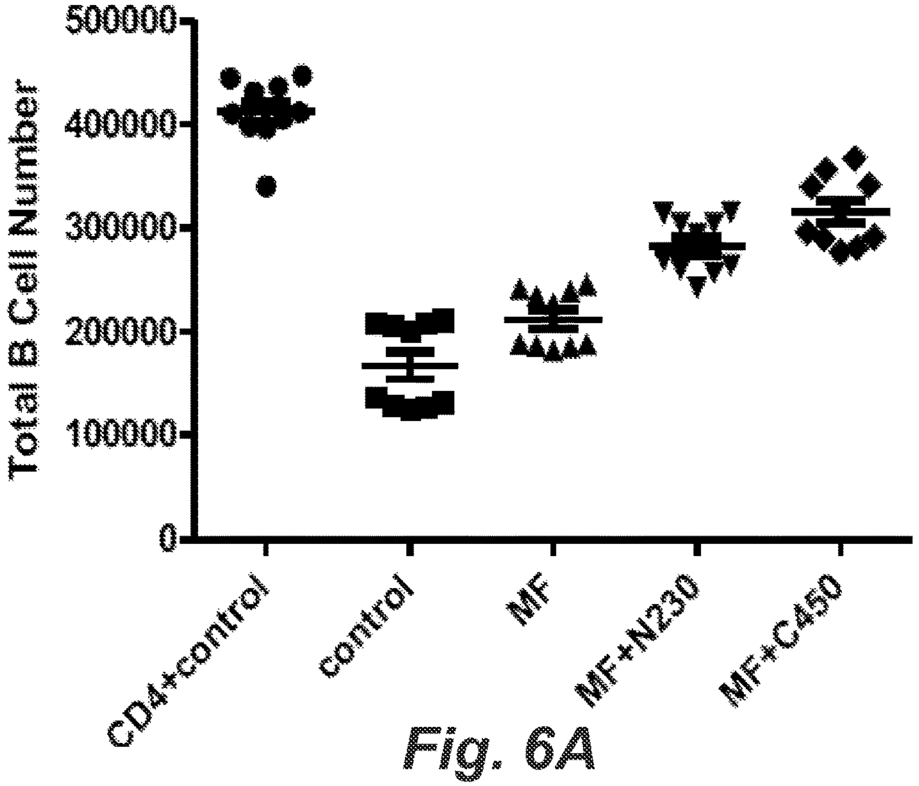
FIGS. 6A-6D is a series of graphs illustrating total pulmonary B-cells after SPD-1 immunization and *Pneumocystis* pneumonia.
Figure 6B:
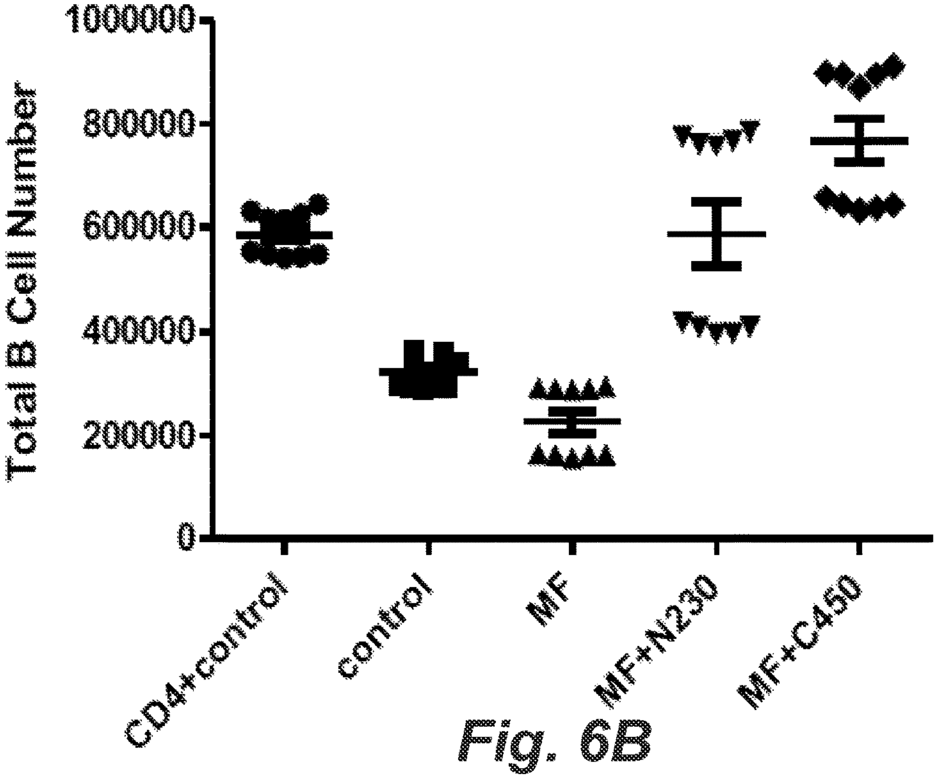
Figure 6C:
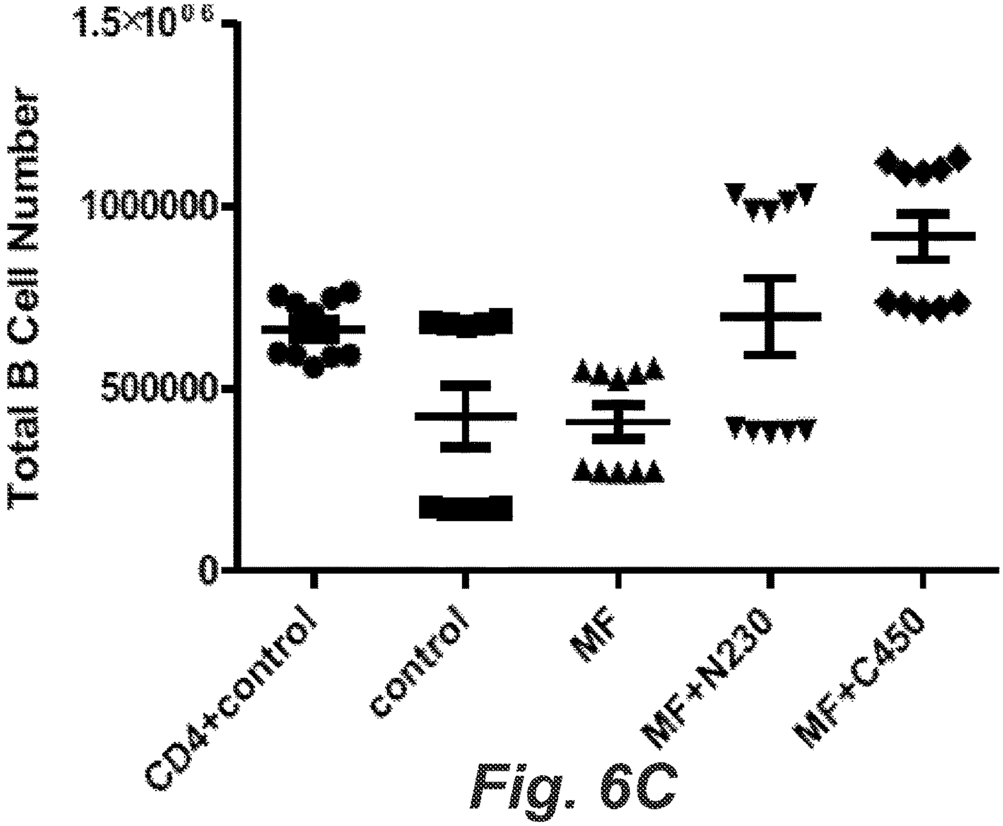
Figure 6D:
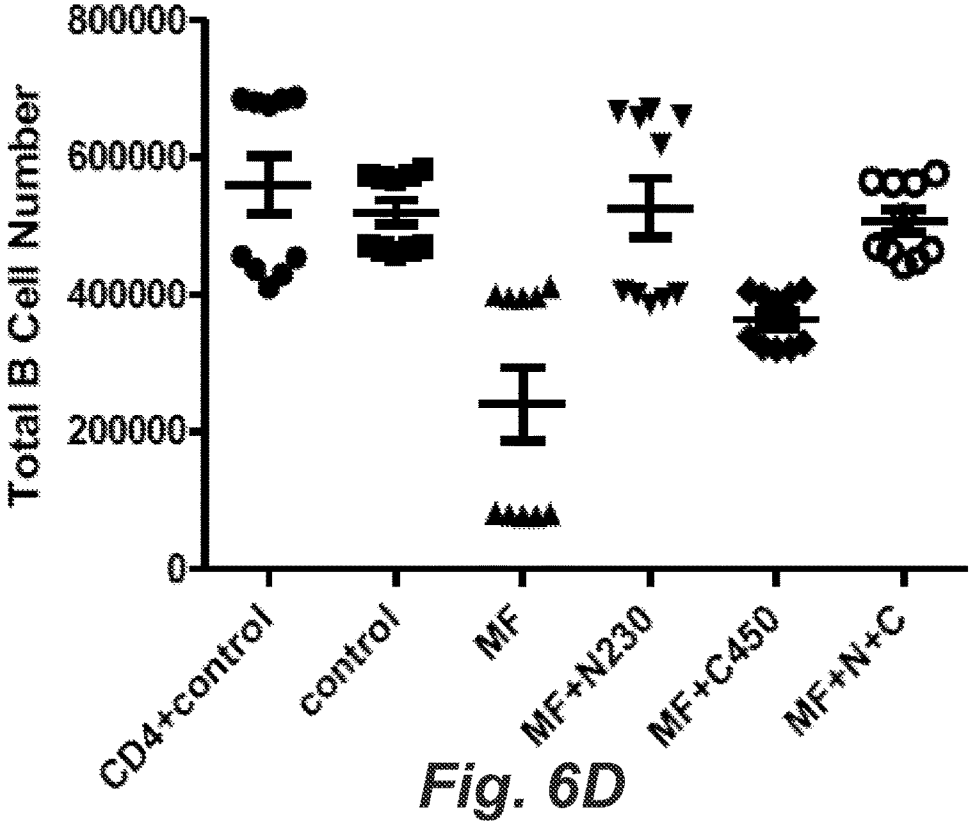
Figure 7A:
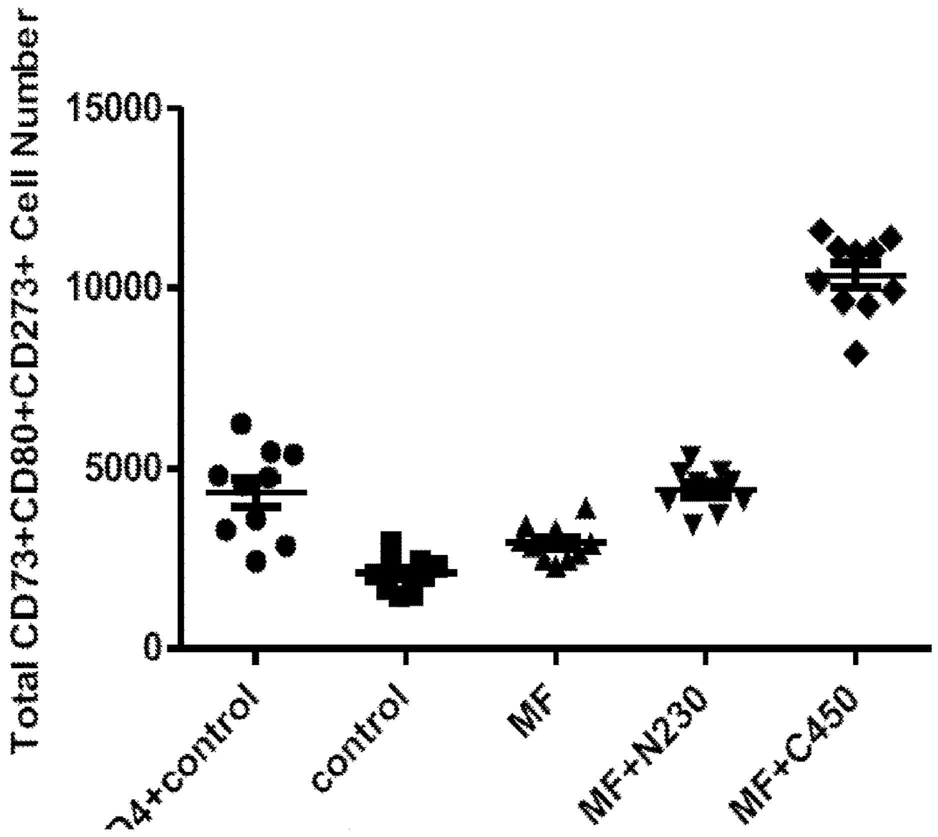
FIGS. 7A-7D is a series of graphs illustrating memory pulmonary B-cells after SPD-1 immunization and *Pneumocystis* pneumonia.
Figure 7B:
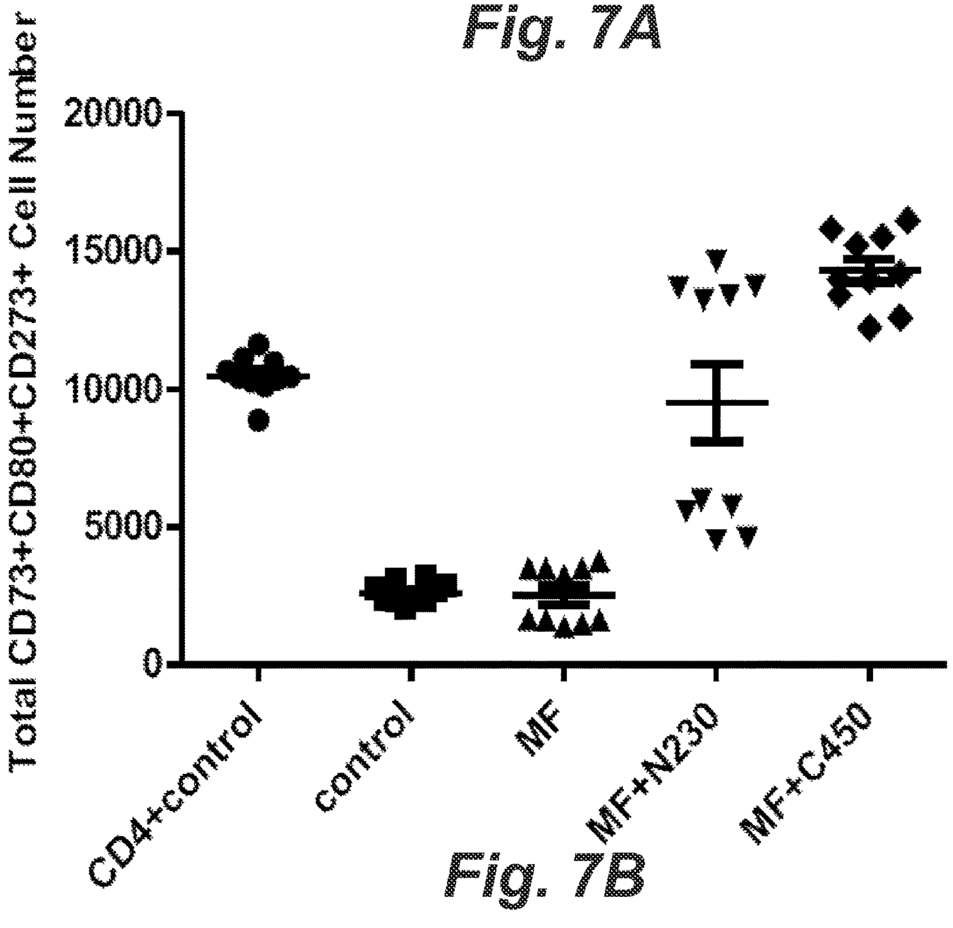
Figure 7C:
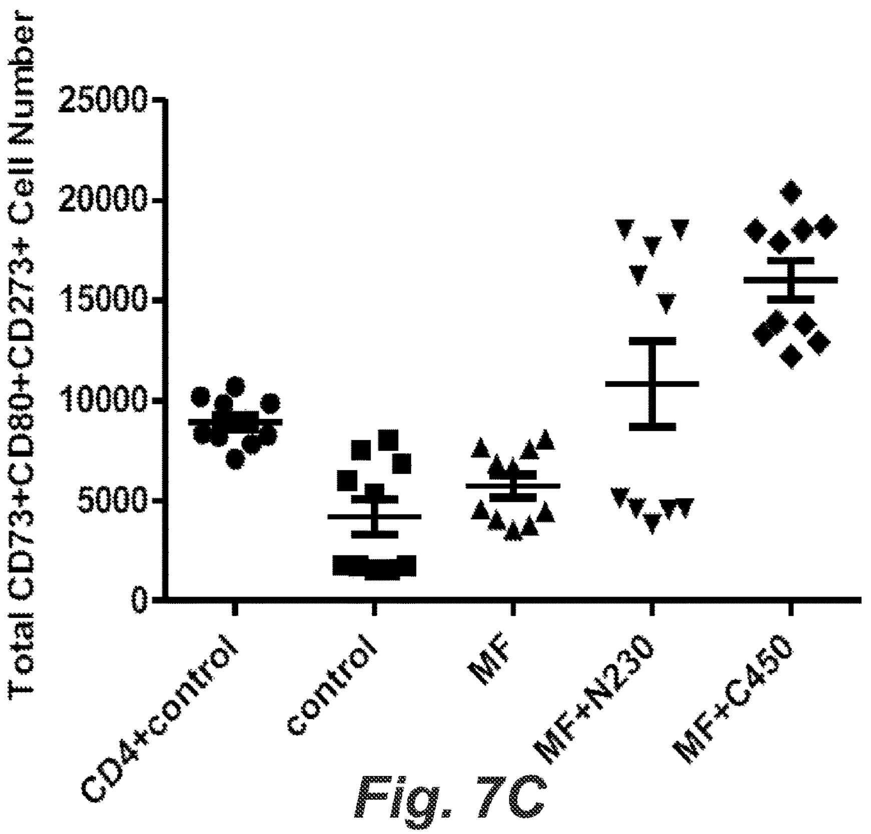
Figure 7D:
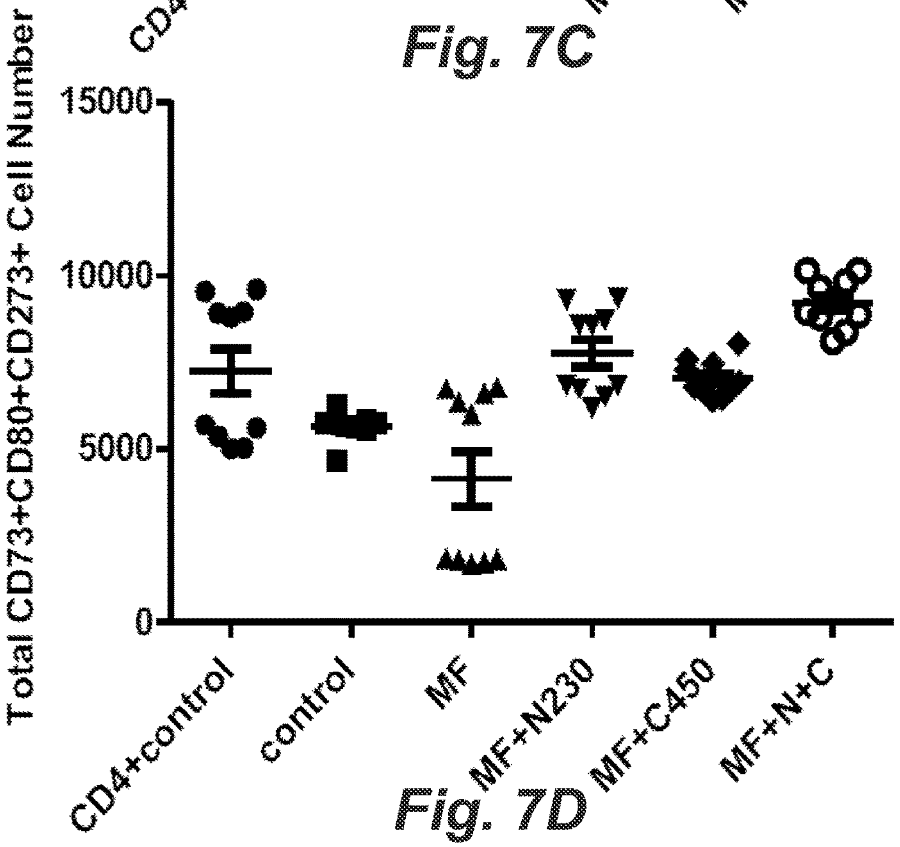
Figure 8A:
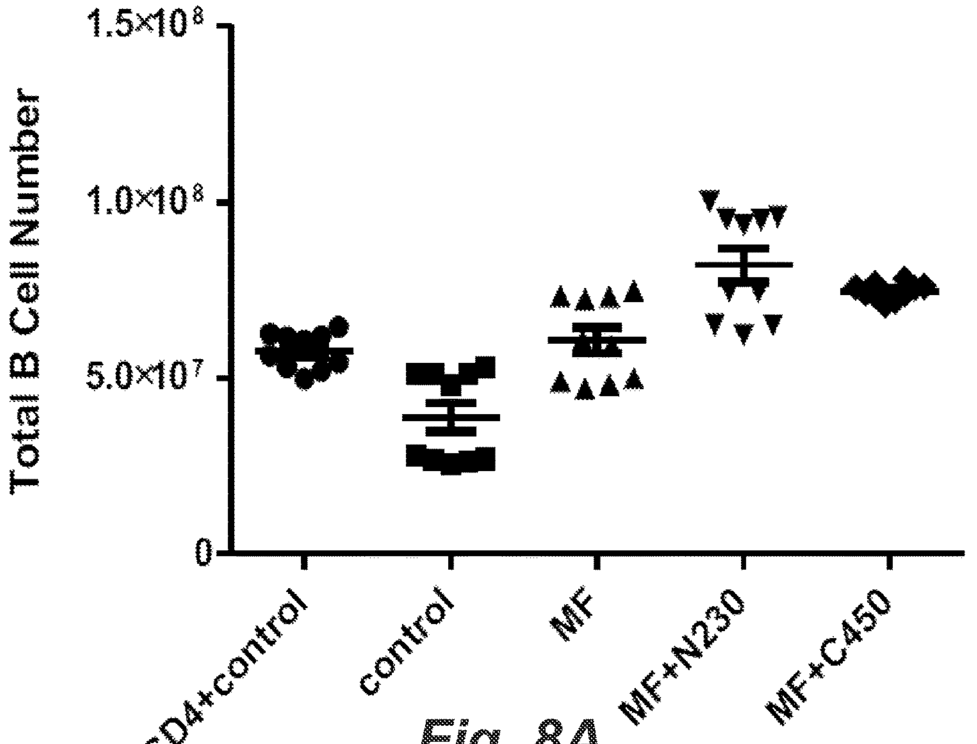
FIGS. 8A-8D shows a series of graphs illustrating total splenic B-cells after SPD-1 immunization and *Pneumocystis* pneumonia.
Figure 8B:
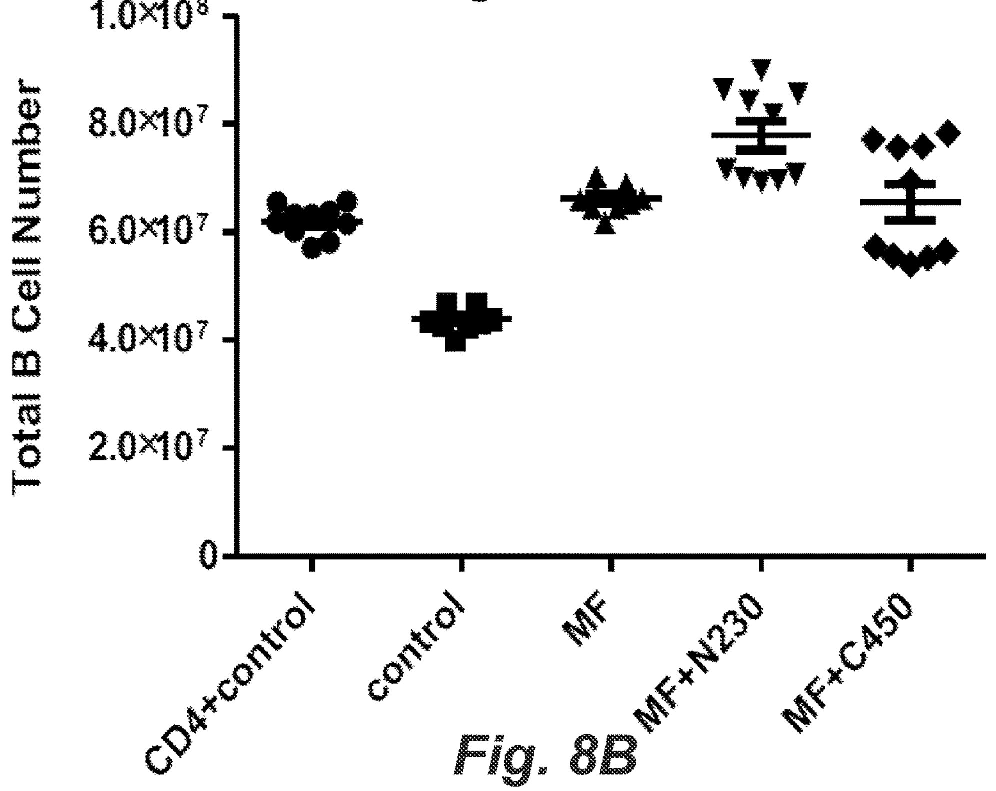
Figure 8C:
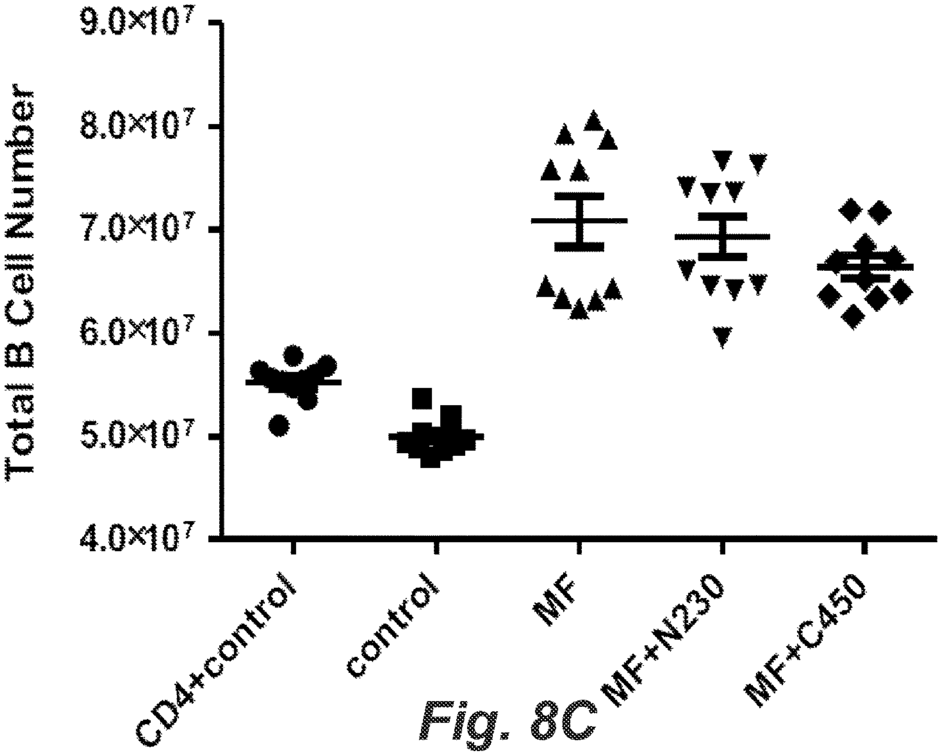
Figure 8D:
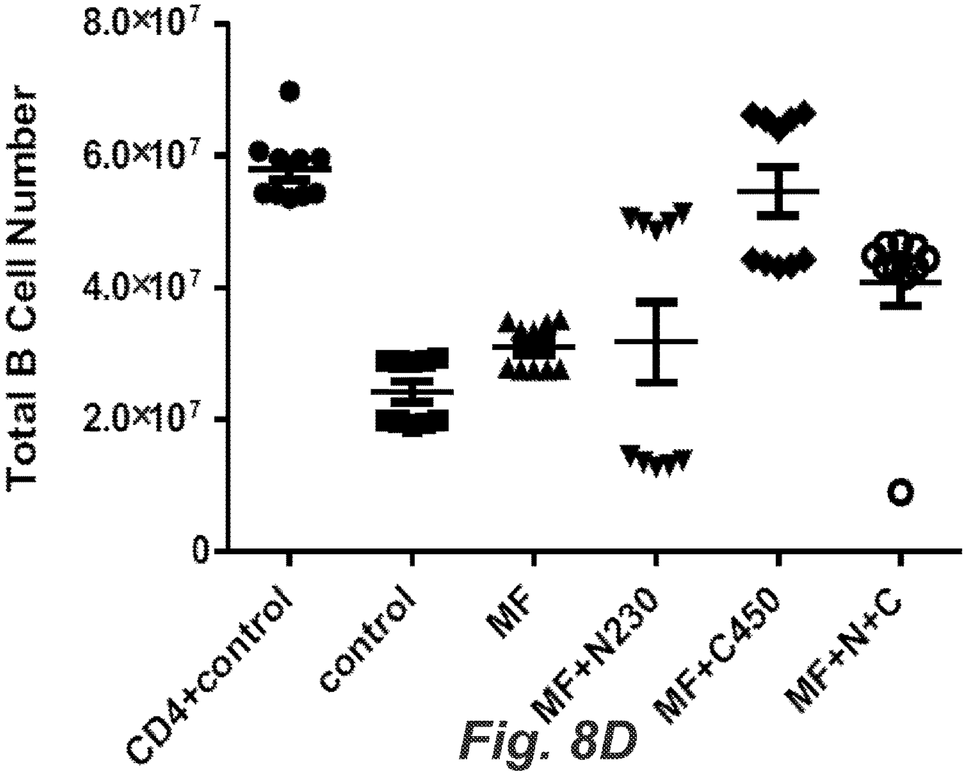
Figure 9A:
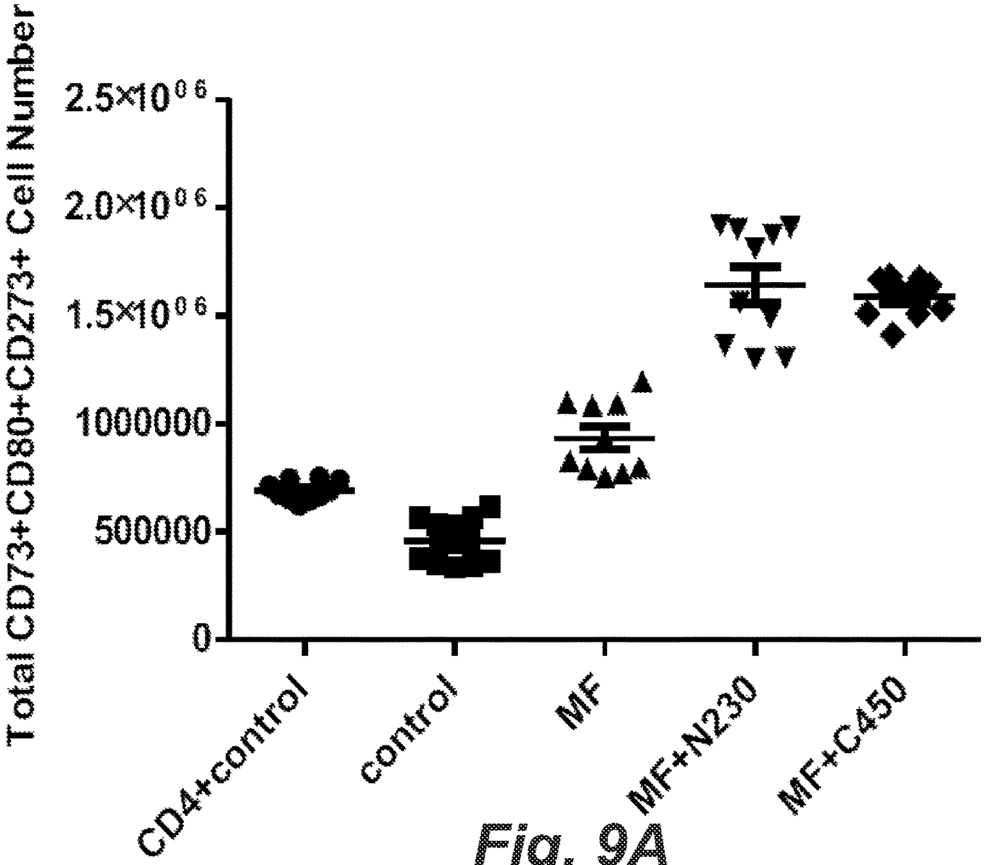
FIGS. 9A-9D is a series of graphs illustrating memory splenic B-cells after SPD-1 immunization and *Pneumocystis* Pneumonia
Figure 9B:
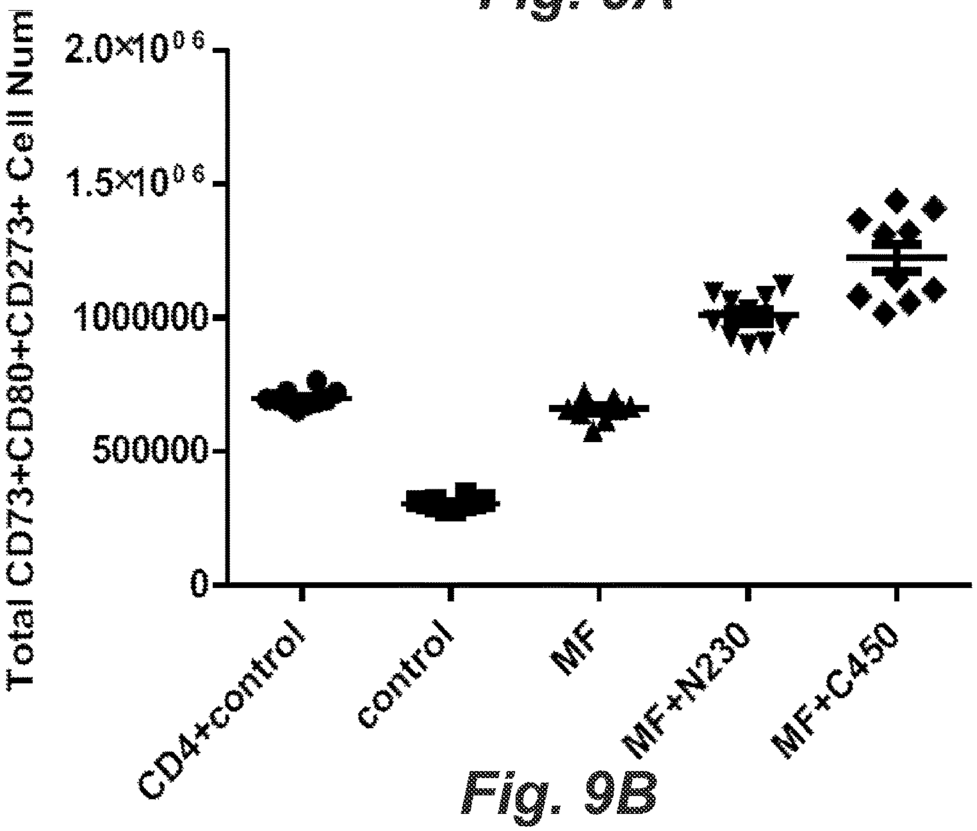
Figure 9C:
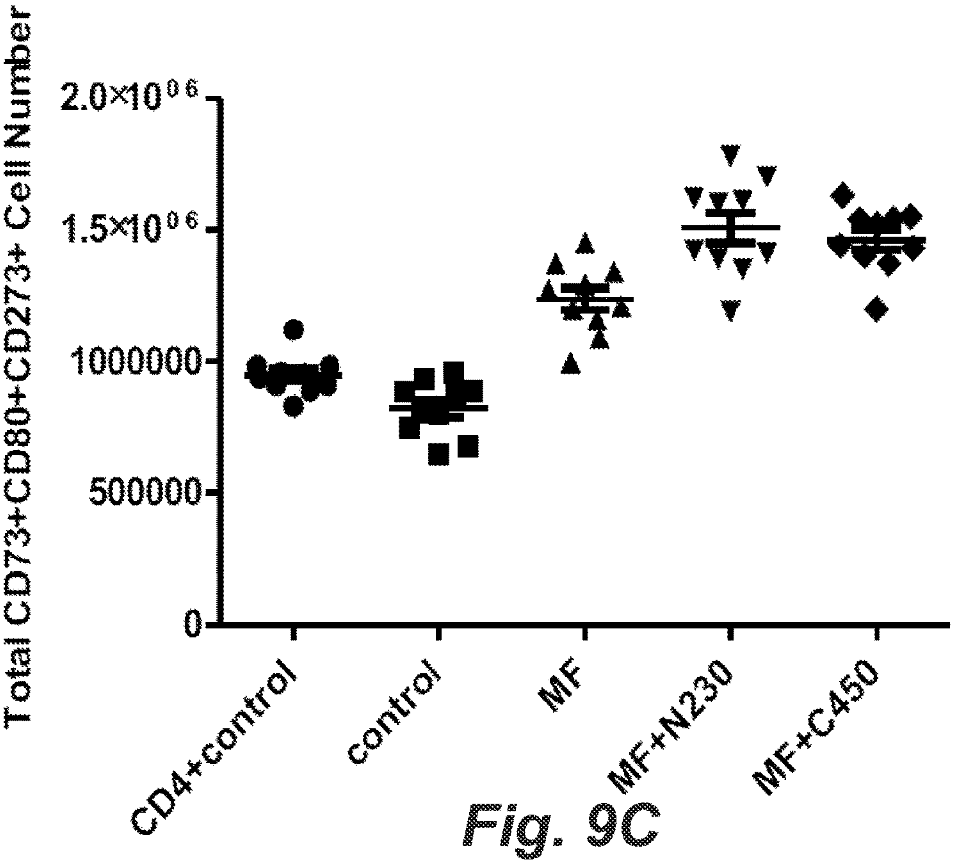
Figure 9D:
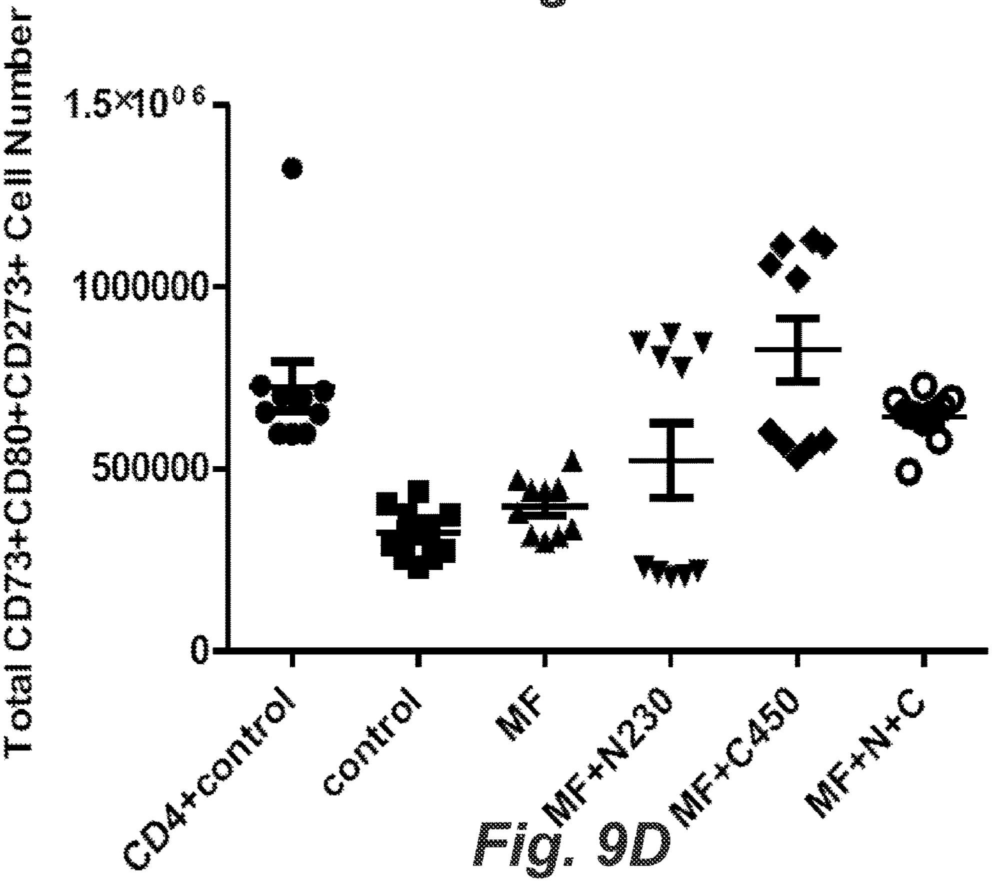
Figure 10A:
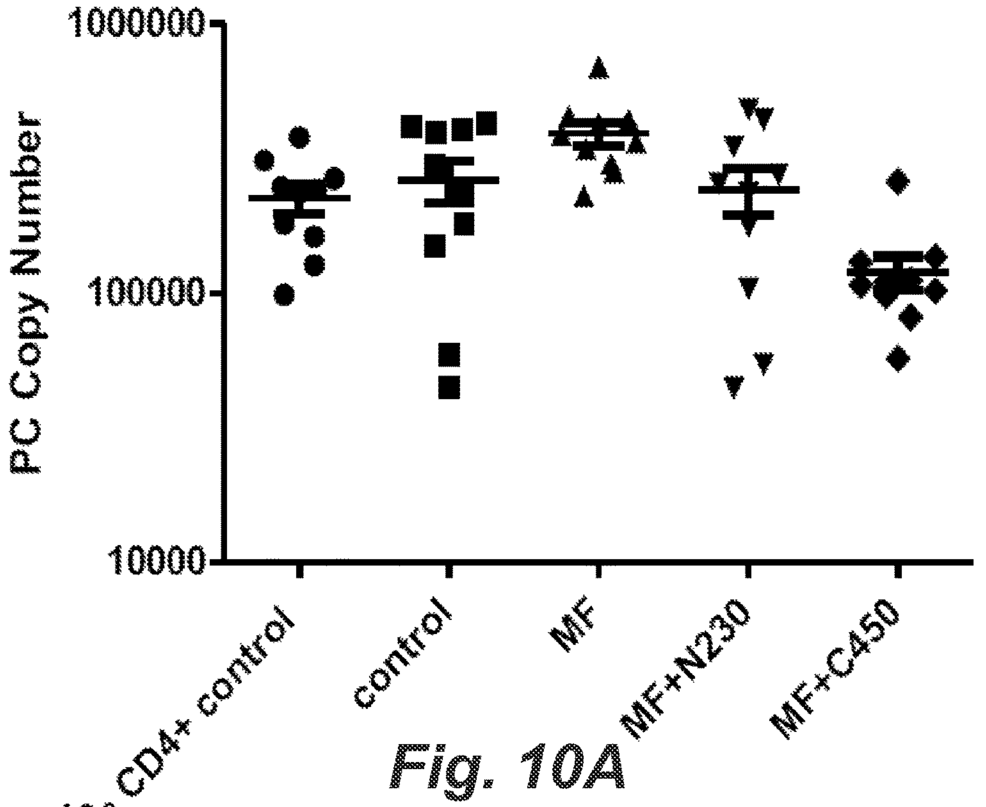
FIGS. 10A-10C is a series of graphs illustrating that both SPD-1 protein fragments (N230 and C450 accelerate *Pneumocystis* clearance with C450 being more effective than N230. Mice were immunized with either N230 or C450 (+adjuvant) then CD4-depleted and infected with *P. murina*. 'CD4$^+$ control' refers to immune-intact mice infected with *P. murina*; 'control' are CD4-depleted & infected mice immunized with saline; 'MF' refers to CD4-depleted & infected mice immunized with adjuvant.
Figure 10B:
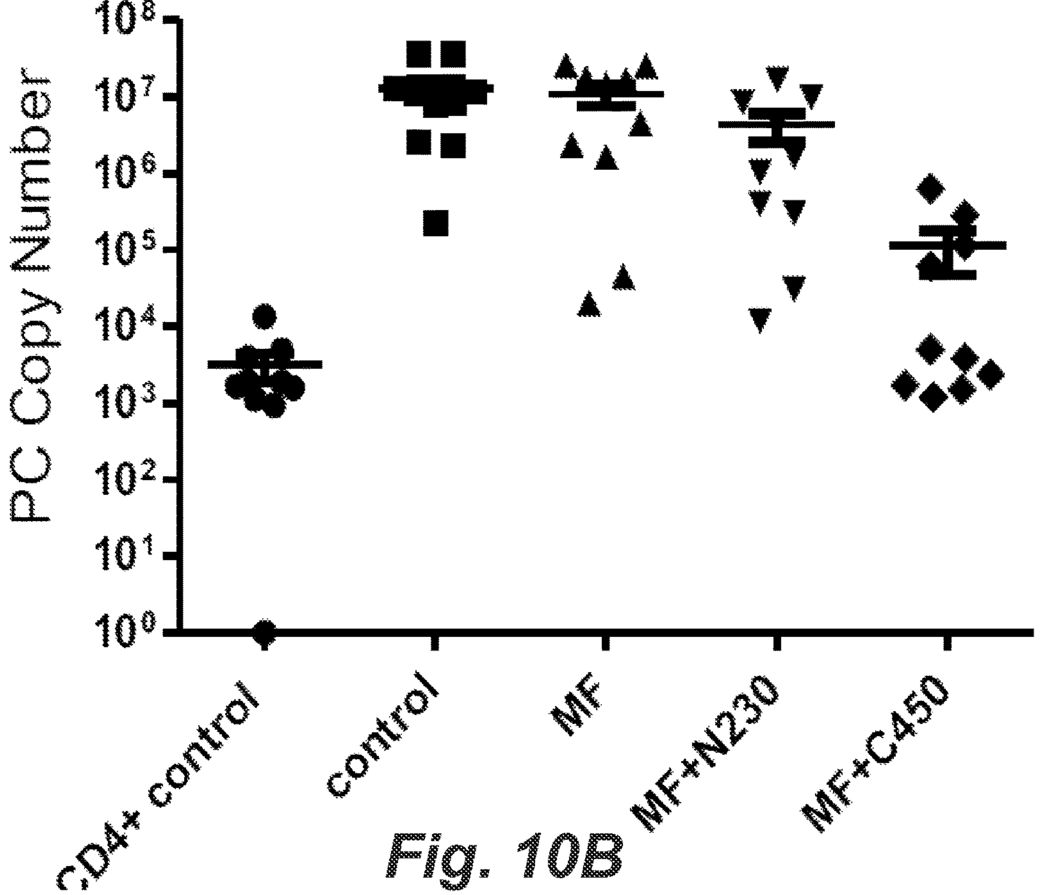
Figure 10C:
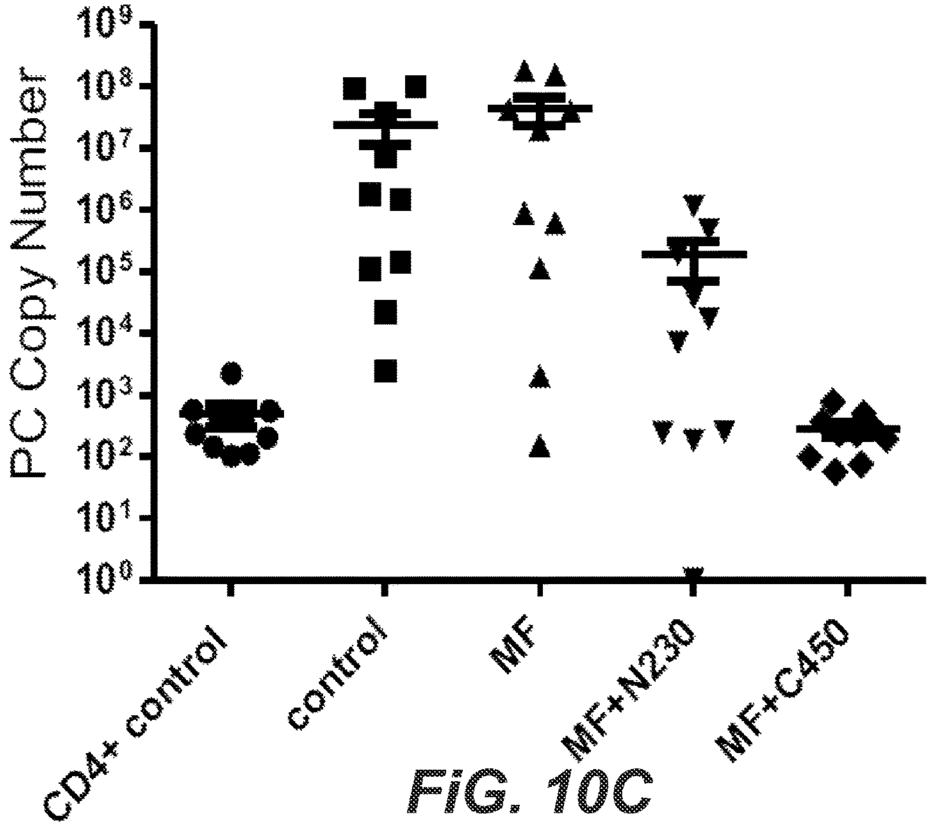
Figure 11:
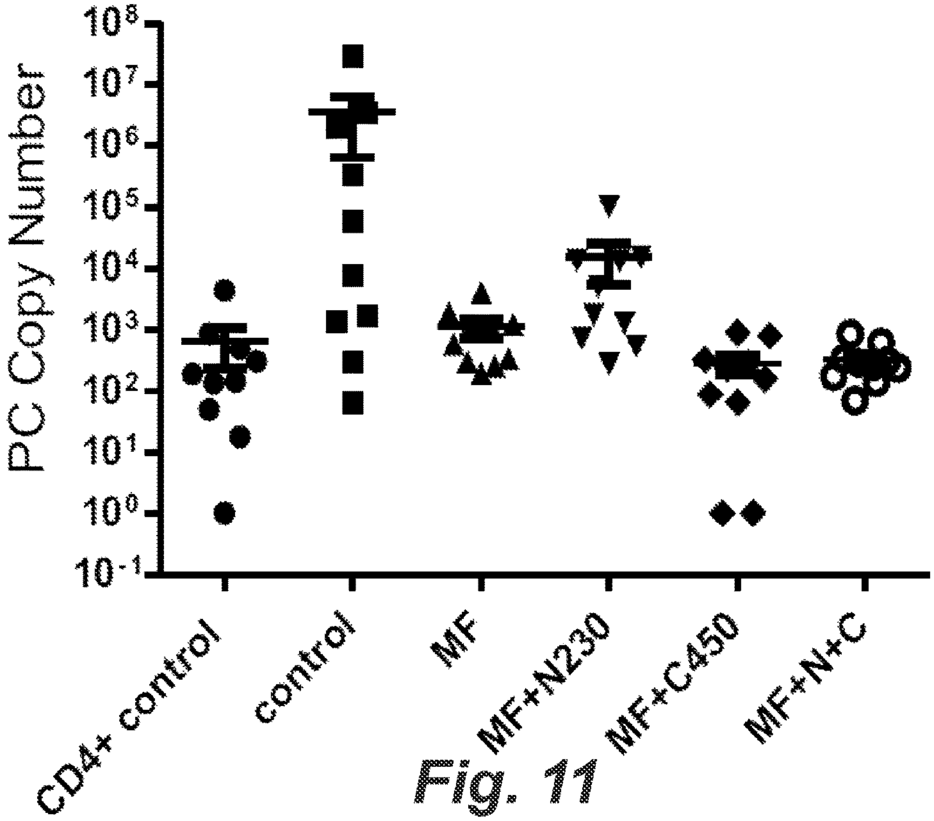
FIG. 11 is a graph illustrating SPD-1 protein fragments & *Pneumocystis* pneumonia resolution. Mice were immunized with either N-230 or C450 or both (+adjuvant) then CD4-depleted and infected with *P. murina*. "CD4+control" refers to immune-intact mice infected with *P. murina*; "control" are CD4-depleted & infected mice immunized with saline; "MF" refers to CD4-depleted & infected mice immunized with adjuvant. The combined N230+C450 immunization strategy was tested only at the 10-week time-point.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law, allowing for the presence of more than that which is recited so long as basic or novel characteristics of that which is recited is not changed by the presence of more than that which is recited, but excludes prior art embodiments.

Abbreviations

SPD-1, Surface Peptidase 1; PCP, *Pneumocystis* pneumonia

Definitions

The term "amino acid" as used herein is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing.

The term "conserved residue" refers to an amino acid that is a member of a group of amino acids having certain common properties. The term "conservative amino acid substitution" refers to the substitution (conceptually or otherwise) of an amino acid from one such group with a different amino acid from the same group. A functional way to define common properties between individual amino acids is to analyze the normalized frequencies of amino acid changes between corresponding proteins of homologous organisms (Schulz, G. E. and R. H. Schinner, Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer, Principles of Protein Structure, Springer-Verlag). Examples of amino acid groups defined in this manner include: (i) a positively-charged group containing Lys, Arg, and His, (ii) a negatively-charged group containing Glu and Asp, (iii) an aromatic group containing Phe, Tyr, and Trp, (iv) a nitrogen ring group containing His and Trp, (v) a large aliphatic nonpolar group containing Val and Leu, (vi) a slightly-polar group containing Met and Cys, (vii) a small-residue group containing Ser, Thr, Asp, Asn, Gly, Ala, Glu, Gln, and Pro, (viii) an aliphatic group containing Val, Leu, Met, and Cys, and (ix) a small, hydroxyl group containing Ser and Thr.

The term "fusion protein" or "fusion polypeptide" as used herein refers to a chimeric protein as that term is known in the art and may be constructed using methods known in the art. In many examples of fusion proteins, there are two different polypeptide sequences, and in certain cases, there may be more. The polynucleotide sequences encoding the fusion protein may be operably linked in frame so that the fusion protein may be translated correctly. A fusion protein may include polypeptide sequences from the same species or from different species. In various embodiments, the fusion polypeptide may contain one or more amino acid sequences linked to a first polypeptide. In the case where more than one amino acid sequence is fused to a first polypeptide, the fusion sequences may be multiple copies of the same sequence, or alternatively, may be different amino acid sequences. The fusion polypeptides may be fused to the N-terminus, the C-terminus, or the N- and C-terminus of the first polypeptide. Exemplary fusion proteins include polypeptides containing a glutathione S-transferase tag (GST-tag), histidine tag (His-tag), an immunoglobulin domain or an immunoglobulin binding domain.

The term "isolated polypeptide" as used herein refers to a polypeptide that may be prepared from recombinant DNA or RNA, or of synthetic origin or natural origin, or some combination thereof, which (1) is not associated with proteins that it are normally found with in nature, (2) is separated from the cell in which it normally occurs, (3) is free of other proteins from the same cellular source, (4) is expressed by a cell from a different species, or (5) does not occur in nature. It is possible for an isolated polypeptide to exist but not to qualify as a purified polypeptide.

The term "isolated nucleic acid" and "isolated polynucleotide" as used herein refers to a polynucleotide whether genomic DNA, cDNA, mRNA, tRNA, rRNA, iRNA, or a polynucleotide obtained from a cellular organelle (such as mitochondria and chloroplast), or whether from synthetic origin, which (1) is not associated with the cell in which the "isolated nucleic acid" is found in nature, or (2) is operably linked to a polynucleotide to which it is not linked in nature. It is possible for an isolated polynucleotide to exist but not qualify as a purified polynucleotide.

The terms "nucleic acid" and "polynucleotide" as used herein refer to a polymeric form of nucleotides, either ribonucleotides or deoxyribonucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

The term "nucleic acid of the disclosure" and "polynucleotide of the disclosure" refers to a nucleic acid encoding a polypeptide of the disclosure. A polynucleotide of the disclosure may comprise all, or a portion of, a subject nucleic acid sequence; a nucleotide sequence at least 60%, 70%, 80%, 90%, 95%, 96%, 97%, 98% or 99% identical to a subject nucleic acid sequence (and every integer between 60 and 100); a nucleotide sequence that hybridizes under stringent conditions to a subject nucleic acid sequence; nucleotide sequences encoding polypeptides that are functionally equivalent to polypeptides of the disclosure; nucleotide sequences encoding polypeptides at least about 60%, 70%, 80%, 85%, 90%, 95%, 98%, 99% homologous or identical with a subject amino acid sequence (and every integer between 60 and 100); nucleotide sequences encoding polypeptides having an activity of a polypeptide of the disclosure and having at least about 60%, 70%, 80%, 85%, 90%, 95%, 98%, 99% or more homology or identity with a subject amino acid sequence (and every integer between 60 and 100); nucleotide sequences that differ by 1 to about 2, 3, 5, 7, 10, 15, 20, 30, 50, 75 or more nucleotide substitutions, additions or deletions, such as allelic variants, of a subject nucleic acid sequence; nucleic acids derived from and evolutionarily related to a subject nucleic acid sequence; and complements of, and nucleotide sequences resulting from the degeneracy of the genetic code, for all of the foregoing and other nucleic acids of the disclosure. Nucleic acids of the disclosure also include homologs, e.g., orthologs and paralogs, of a subject nucleic acid sequence and also variants of a subject nucleic acid sequence which have been codon optimized for expression in a particular organism (e.g., host cell).

The terms "operably linked" and "operatively inserted" as used herein, when describing the relationship between two nucleic acid regions, refer to the juxtaposition wherein the regions are in a relationship permitting them to function in their intended manner. For example, a control sequence "operably linked" to a coding sequence is ligated in such a way that expression of the coding sequence is achieved under conditions compatible with the control sequences, such as when the appropriate molecules (e.g., inducers and polymerases) are bound to the control or regulatory sequence(s).

The term "polypeptide", and the terms "protein" and "peptide" as used herein, and which are used interchangeably herein, refers to a polymer of amino acids. Exemplary polypeptides include gene products, naturally-occurring proteins, homologs, orthologs, paralogs, fragments, and other equivalents, variants and analogs of the foregoing.

The terms "polypeptide fragment" or "fragment", as used herein and when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus or carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. A fragment can retain one or more of the biological activities of the reference polypeptide. In certain embodiments, a fragment may comprise a domain having the desired biological activity, and optionally additional amino acids on one or both sides of the domain, which additional amino acids may number from 5, 10, 15, 20, 30, 40, 50, or up to 100 or more residues. Further, fragments can include a sub-fragment of a specific region, which sub-fragment retains a function of the region from which it is derived. In another embodiment, a fragment may have immunogenic properties.

The term "polypeptide of the disclosure" as used herein refers to a polypeptide containing a subject amino acid sequence, or an equivalent or fragment thereof. Polypeptides of the disclosure include polypeptides containing all or a portion of a subject amino acid sequence; a subject amino acid sequence with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% homologous to a subject amino acid sequence (and every integer between 60 and 100); and functional fragments thereof. Polypeptides of the disclosure also include homologs, e.g., orthologs and paralogs, of a subject amino acid sequence.

It is also possible to modify the structure of the polypeptides of the disclosure for such purposes as enhancing therapeutic or prophylactic efficacy, or stability (e.g., ex vivo shelf life, resistance to proteolytic degradation in vivo, etc.). Such modified polypeptides, when designed to retain at least one activity of the naturally-occurring form of the protein, are considered "functional equivalents" of the polypeptides described in more detail herein. Such modified polypeptides may be produced, for instance, by amino acid substitution, deletion, or addition, which substitutions may consist in whole or part by conservative amino acid substitutions.

For instance, it is reasonable to expect that an isolated conservative amino acid substitution, such as replacement of a leucine with an isoleucine or valine, an aspartate with a glutamate, a threonine with a serine, will not have a major affect on the biological activity of the resulting molecule. Whether a change in the amino acid sequence of a polypeptide results in a functional homolog may be readily determined by assessing the ability of the variant polypeptide to produce a response similar to that of the wild-type protein. Polypeptides in which more than one replacement has taken place may readily be tested in the same manner.

The term "purified" as used herein refers to an object species that is the predominant species present (i.e., on a molar basis it is more abundant than any other individual species in the composition). A "purified fraction" is a composition wherein the object species is at least about 50 percent (on a molar basis) of all species present. In making the determination of the purity or a species in solution or dispersion, the solvent or matrix in which the species is dissolved or dispersed is usually not included in such determination; instead, only the species (including the one of interest) dissolved or dispersed are taken into account. Generally, a purified composition will have one species that is more than about 80% of all species present in the composition, more than about 85%, 90%, 95%, 99% or more of all species present. The object species may be purified to essential homogeneity (contaminant species cannot be detected in the composition by conventional detection methods) wherein the composition is essentially a single species. A skilled artisan may purify a polypeptide of the disclosure using standard techniques for protein purification in light of the teachings herein. Purity of a polypeptide may be determined by a number of methods known to those of skill in the art, including for example, amino-terminal amino acid sequence analysis, gel electrophoresis, mass-spectrometry analysis and the methods described herein.

The terms "recombinant protein" or "recombinant polypeptide" as used herein refer to a polypeptide which is produced by recombinant DNA techniques. An example of such techniques includes the case when DNA encoding the expressed protein or peptide is inserted into a suitable expression vector that is in turn used to transform a host cell to produce the protein or polypeptide encoded by the DNA.

The term "regulatory sequence" as used herein is a generic term used throughout the specification to refer to polynucleotide sequences, such as initiation signals, enhancers, regulators and promoters that are necessary or desirable to affect the expression of coding and non-coding sequences to which they are operably linked. Exemplary regulatory sequences are described in Goeddel; Gene Expression Technology: Methods in Enzymology, Academic Press, San Diego, Calif. (1990), and include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase (e.g., Pho5), the promoters of the yeast α-mating factors, the polyhedron promoter of the baculovirus system and other sequences known to control the expression of genes of prokaryotic or eukaryotic cells or their viruses, and various combinations thereof. The nature and use of such control sequences may differ depending upon the host organism. In prokaryotes, such regulatory sequences generally include promoter, ribosomal binding site, and transcription termination sequences. The term "regulatory sequence" is intended to include, at a minimum, components whose presence may influence expression, and may also include additional components whose presence is advantageous, for example, leader sequences and fusion partner sequences. In certain embodiments, transcription of a polynucleotide sequence is under the control of a promoter sequence (or other regulatory sequence) which controls the expression of the polynucleotide in a cell-type in which expression is intended. It will also be understood that the polynucleotide can be under the control of regulatory sequences which are the same or different from those sequences which control expression of the naturally-occurring form of the polynucleotide.

The term "sequence similarity" as used herein refers to the proportion of base matches between two nucleic acid sequences or the proportion of amino acid matches between two amino acid sequences. When sequence homology is expressed as a percentage, e.g., 50%, the percentage denotes the proportion of matches over the length of sequence from a desired sequence that is compared to some other sequence. Gaps (in either of the two sequences) are permitted to maximize matching; gap lengths of 15 bases or less are usually used, 6 bases or less are used more frequently, with 2 bases or less used even more frequently. The term "sequence identity" means that sequences are identical (i.e., on a nucleotide-by-nucleotide basis for nucleic acids or amino acid-by-amino acid basis for polypeptides) over a window of comparison. The term "percentage of sequence identity" is calculated by comparing two optimally aligned sequences over the comparison window, determining the number of positions at which the identical amino acids or nucleotides occurs in both sequences to yield the number of matched positions, dividing the number of matched positions by the total number of positions in the comparison window, and multiplying the result by 100 to yield the percentage of sequence identity. Methods to calculate sequence identity are known to those of skill in the art and described in further detail below.

The term "soluble" as used herein with reference to a polypeptide of the disclosure or other protein, refers to the expression in cell culture, at least some portion of the polypeptide or protein expressed remains in the cytoplasmic fraction of the cell and does not fractionate with the cellular debris upon lysis and centrifugation of the lysate. Solubility of a polypeptide may be increased by a variety of art recognized methods, including fusion to a heterologous amino acid sequence, deletion of amino acid residues, amino acid substitution (e.g., enriching the sequence with amino acid residues having hydrophilic side chains), and chemical modification (e.g., addition of hydrophilic groups).

The solubility of polypeptides may be measured using a variety of art recognized techniques, including, dynamic light scattering to determine aggregation state, UV absorption, centrifugation to separate aggregated from non-aggregated material, and SDS gel electrophoresis (e.g., the amount of protein in the soluble fraction is compared to the amount of protein in the soluble and insoluble fractions combined). When expressed in a host cell, the polypeptides of the disclosure may be at least about 1%, 2%, 5%, 10%, 20%, 30%, 40%, 50%, 60%, 70%, 80%, 90% or more soluble, e.g., at least about 1%, 2%, 5%, 10%, 20%, 30%, 40%, 50%, 60%, 70%, 80%, 90% or more of the total amount of protein expressed in the cell is found in the cytoplasmic fraction. In certain embodiments, a one liter culture of cells expressing a polypeptide of the disclosure will produce at least about 0.1, 0.2, 0.5, 1, 2, 5, 10, 20, 30, 40, 50 milligrams of more of soluble protein. In an exemplary embodiment, a polypeptide of the disclosure is at least about 10% soluble and will produce at least about 1 milligram of protein from a one liter cell culture.

The term "specifically hybridizes" as used herein refers to detectable and specific nucleic acid binding. Polynucleotides, oligonucleotides and nucleic acids of the disclosure selectively hybridize to nucleic acid strands under hybridization and wash conditions that minimize appreciable amounts of detectable binding to nonspecific nucleic acids. Stringent conditions may be used to achieve selective hybridization conditions as known in the art and discussed herein. Generally, the nucleic acid sequence identity between the polynucleotides, oligonucleotides, and nucleic acids of the disclosure and a nucleic acid sequence of interest will be at least 30%, 40%, 50%, 60%, 70%, 80%, 85%, 90%, 95%, 98%, 99%, or more (and every integer between 30 and 100). In certain instances, hybridization and washing conditions are performed under stringent conditions according to conventional hybridization procedures and as described further herein.

The terms "stringent conditions" or "stringent hybridization conditions" as used herein refer to conditions which promote specific hybridization between two complementary polynucleotide strands so as to form a duplex. Stringent conditions may be selected to be about 5° C. lower than the thermal melting point ($T_m$) for a given polynucleotide duplex at a defined ionic strength and pH. The length of the complementary polynucleotide strands and their GC content will determine the $T_m$ of the duplex, and thus the hybridization conditions necessary for obtaining a desired specificity of hybridization. The $T_m$ is the temperature (under defined ionic strength and pH) at which 50% of a polynucleotide sequence hybridizes to a perfectly matched complementary strand. In certain cases it may be desirable to increase the stringency of the hybridization conditions to be about equal to the $T_m$ for a particular duplex.

A variety of techniques for estimating the $T_m$ are available. Typically, G-C base pairs in a duplex are estimated to contribute about 3° C. to the $T_m$, while A-T base pairs are estimated to contribute about 2° C., up to a theoretical maximum of about 80-100° C.

However, more sophisticated models of $T_m$ are available in which G-C stacking interactions, solvent effects, the desired assay temperature and the like are taken into account. For example, probes can be designed to have a dissociation temperature ($T_d$) of approximately 60° C., using the formula: $T_d$=(((3×#GC)+(2×#AT))×37)−562) #bp)−5; where #GC, #AT, and #bp are the number of guanine-cytosine base pairs, the number of adenine-thymine base pairs, and the number of total base pairs, respectively, involved in the formation of the duplex.

Hybridization may be carried out in 5×SSC, 4×SSC, 3×SSC, 2×SSC, 1×SSC or 0.2×SSC for at least about 1 hour, 2 h, 5 h, 12 h, or 24 h. The temperature of the hybridization may be increased to adjust the stringency of the reaction, for example, from about 25° C. (room temperature), to about 45° C., 50° C., 55° C., 60° C., or 65° C. The hybridization reaction may also include another agent affecting the stringency, for example, hybridization conducted in the presence of 50% formamide increases the stringency of hybridization at a defined temperature.

The hybridization reaction may be followed by a single wash step, or two or more wash steps, which may be at the same or a different salinity and temperature. For example, the temperature of the wash may be increased to adjust the stringency from about 25° C. (room temperature), to about 45° C., 50° C., 55° C., 60° C., 65° C., or higher. The wash step may be conducted in the presence of a detergent, e.g., 0.1 or 0.2% SDS. For example, hybridization may be followed by two wash steps at 65° C. each for about 20 min in 2×SSC, 0.1% SDS, and optionally two additional wash steps at 65° C. each for about 20 min in 0.2×SSC, 0.1% SDS.

Exemplary stringent hybridization conditions include overnight hybridization at 65° C. in a solution containing 50% formamide, 10×Denhardt (0.2% Ficoll, 0.2% polyvinylpyrrolidone, 0.2% bovine serum albumin) and 200 μg/ml of denatured carrier DNA, e.g., sheared salmon sperm DNA, followed by two wash steps at 65° C. each for about 20 min in 2×SSC, 0.1% SDS, and two wash steps at 65° C. each for about 20 min in 0.2×SSC, 0.1% SDS.

Hybridization may consist of hybridizing two nucleic acids in solution, or a nucleic acid in solution to a nucleic acid attached to a solid support, e.g., a filter. When one nucleic acid is on a solid support, a prehybridization step may be conducted prior to hybridization. Prehybridization may be carried out for at least about 1 h, 3 h or 10 h in the same solution and at the same temperature as the hybridization solution (without the complementary polynucleotide strand).

Appropriate stringency conditions are known to those skilled in the art or may be determined experimentally by the skilled artisan. See, for example, Current Protocols in Molecular Biology, John Wiley & Sons, N.Y. (1989), 6.3.1-12.3.6; Sambrook et al., 1989, Molecular Cloning, A Laboratory Manual, Cold Spring Harbor Press, N.Y.; S. Agrawal (ed.) Methods in Molecular Biology, volume 20; Tijssen (1993) Laboratory Techniques in Biochemistry and Molecular Biology-Hybridization With Nucleic Acid Probes, e.g., part I chapter 2 "Overview of principles of hybridization and the strategy of nucleic acid probe assays", Elsevier, N.Y.; and Tibanyenda et al., (1984) *Eur. J. Biochem.* 139: 19 and Ebel et al., (1992) *Biochem.* 31: 12083.

The term "vector" as used herein refers to a nucleic acid capable of transporting another nucleic acid to which it has been linked. One type of vector which may be used in accord with the disclosure is an episome, i.e., a nucleic acid capable of extra-chromosomal replication. Other vectors include those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA molecules which, in their vector form are not bound to the chromosome. In the present specification, "plasmid" and "vector" are used interchangeably as the plasmid is the most commonly used form of vector. However, the disclosure is intended to include such other forms of expression vectors which serve equivalent functions and which become known in the art subsequently hereto.

The nucleic acids of the disclosure may be used as diagnostic reagents to detect the presence or absence of the target DNA or RNA sequences to which they specifically bind, such as for determining the level of expression of a nucleic acid of the disclosure. In one aspect, the present disclosure contemplates a method for detecting the presence of a nucleic acid of the disclosure or a portion thereof in a sample, the method of the steps of: (a) providing an oligonucleotide at least eight nucleotides in length, the oligonucleotide being complementary to a portion of a nucleic acid of the disclosure; (b) contacting the oligonucleotide with a sample containing at least one nucleic acid under conditions that permit hybridization of the oligonucleotide with a nucleic acid of the disclosure or a portion thereof; and (c) detecting hybridization of the oligonucleotide to a nucleic acid in the sample, thereby detecting the presence of a nucleic acid of the disclosure or a portion thereof in the sample. In another aspect, the present disclosure contemplates a method for detecting the presence of a nucleic acid of the disclosure or a portion thereof in a sample, by (a) providing a pair of single stranded oligonucleotides, each of which is at least eight nucleotides in length, complementary to sequences of a nucleic acid of the disclosure, and wherein the sequences to which the oligonucleotides are complementary are at least ten nucleotides apart; and (b) contacting the oligonucleotides with a sample containing at least one nucleic acid under hybridization conditions; (c) amplifying the nucleotide sequence between the two oligonucleotide primers; and (d) detecting the presence of the amplified sequence, thereby detecting the presence of a nucleic acid of the disclosure or a portion thereof in the sample.

In another aspect of the disclosure, the polynucleotide of the disclosure is provided in an expression vector containing a nucleotide sequence encoding a polypeptide of the disclosure and operably linked to at least one regulatory sequence. It should be understood that the design of the expression vector may depend on such factors as the choice of the host cell to be transformed and/or the type of protein desired to be expressed. The vector's copy number, the ability to control that copy number and the expression of any other protein encoded by the vector, such as antibiotic markers, should be considered.

An expression vector containing the polynucleotide of the disclosure can then be used as a pharmaceutical agent to reduce an infection in a subject infected with a *Pneumocystis* sp. or as a vaccine (also a pharmaceutical agent) to prevent an animal from being infected with such as *P. jirovecii*, or to reduce the symptoms and course of the disease if the subject patient does become infected. One manner of using an expression vector as a pharmaceutical agent is to administer a nucleic acid vaccine to the animal at risk of being infected or to the animal after being infected. Nucleic acid vaccine technology is well-described in the art. Some descriptions can be found in U.S. Pat. No. 6,562,376 (Hooper et al.); U.S. Pat. No. 5,589,466 (Felgner et al.); U.S. Pat. No. 6,673,776 (Felgner et al.); and U.S. Pat. No. 6,710,035 (Felgner et al.). Nucleic acid vaccines can be injected into muscle or intradermally, can be electroporated into the animal (see WO 01/23537, King et al.; and WO 01/68889, Malone et al.), via lipid compositions (see U.S. Pat. No. 5,703,055, Felgner et al.), or other mechanisms known in the art field.

The polynucleotide of the disclosure may be used to cause expression and over-expression of a polypeptide of the disclosure in cells propagated in culture, e.g. to produce proteins or polypeptides, including fusion proteins or polypeptides.

This disclosure pertains to a host cell transfected with a recombinant gene in order to express a polypeptide of the disclosure. The host cell may be any prokaryotic or eukaryotic cell. For example, a polypeptide of the disclosure may be expressed in bacterial cells, such as *E. coli*, insect cells (baculovirus), yeast, plant, or mammalian cells. In those instances when the host cell is human, it may or may not be in a live subject. Other suitable host cells are known to those skilled in the art. Additionally, the host cell may be supplemented with tRNA molecules not typically found in the host so as to optimize expression of the polypeptide. Alternatively, the nucleotide sequence may be altered to optimize expression in the host cell, yet the protein produced would have high homology to the originally encoded protein. Other methods suitable for maximizing expression of the polypeptide will be known to those in the art.

The present disclosure further pertains to methods of producing the polypeptides of the disclosure. For example, a host cell transfected with an expression vector encoding a polypeptide of the disclosure may be cultured under appropriate conditions to allow expression of the polypeptide to occur. The polypeptide may be secreted and isolated from a mixture of cells and medium containing the polypeptide. Alternatively, the polypeptide may be retained cytoplasmically and the cells harvested, lysed and the protein isolated.

A cell culture includes host cells, media and other byproducts. Suitable media for cell culture are well known in the art. The polypeptide may be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of a polypeptide of the disclosure.

Thus, a nucleotide sequence encoding all or a selected portion of polypeptide of the disclosure, may be used to produce a recombinant form of the protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, may be employed to prepare recombinant polypeptides of the disclosure by microbial means or tissue-culture technology.

Suitable vectors for the expression of a polypeptide of the disclosure include plasmids of the types: pTrcHis-derived plasmids, pET-derived plasmids, pBR322-derived plasmids, pEMBL-derived plasmids, pEX-derived plasmids, pBTacderived plasmids and pUC-derived plasmids for expression in prokaryotic cells, such as *E. coli*. The various methods employed in the preparation of the plasmids and transformation of host organisms are well known in the art. For other suitable expression systems for both prokaryotic and eukaryotic cells, as well as general recombinant procedures, see Molecular Cloning, A Laboratory Manual, 2nd Ed., ed. by Sambrook, Fritsch and Maniatis (Cold Spring Harbor Laboratory Press, 1989) Chapters 16 and 17.

Fusion expression systems can be useful when it is desirable to produce an immunogenic fragment of a polypeptide of the disclosure. For example, the VP6 capsid protein of rotavirus may be used as an immunologic carrier protein for portions of polypeptide, either in the monomeric form or in the form of a viral particle. The nucleic acid sequences corresponding to the portion of a polypeptide of the disclosure to which antibodies are to be raised may be incorporated into a fusion gene construct which includes coding sequences for a late vaccinia virus structural protein to produce a set of recombinant viruses expressing fusion proteins comprising a portion of the protein as part of the virion. The Hepatitis B surface antigen may also be utilized in this role as well. Similarly, chimeric constructs coding for fusion proteins containing a portion of a polypeptide of the disclosure and the poliovirus capsid protein may be created to enhance immunogenicity (see, for example, EP Publication NO: 0259149; and Evans et al., (1989) Nature 339:385; Huang et al., (1988) J. Virol. 62: 3855; and Schlienger et al., (1992) J. Virol. 66:2).

Fusion proteins may facilitate the expression and/or purification of proteins. For example, a polypeptide of the disclosure may be generated as a glutathione-S-transferase (GST) fusion protein. Such GST fusion proteins may be used to simplify purification of a polypeptide of the disclosure, such as through the use of glutathione-derivatized matrices (see, for example, Current Protocols in Molecular Biology, eds. Ausubel et al., (N.Y.: John Wiley & Sons, 1991)). A fusion gene coding for a purification leader sequence, such as a poly-(His)/enterokinase cleavage site sequence at the N-terminus of the desired portion of the recombinant protein, may allow purification of the expressed fusion protein by affinity chromatography using a $Ni^{2+}$ metal resin. The purification leader sequence may then be subsequently removed by treatment with enterokinase to provide the purified protein (e.g., see Hochuli et al., (1987) *J. Chromatography* 411: 177; and Janknecht et al., *Proc. Natl. Acad. Sci U.S.A.* 88: 8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene may be synthesized by conventional techniques including automated DNA synthesizers. Alternatively, PCR amplification of gene fragments may be carried out using anchor primers that give rise to complementary overhangs between two consecutive gene fragments that may subsequently be annealed to generate a chimeric gene sequence (see, for example, Current Protocols in Molecular Biology, eds. Ausubel et al., John Wiley & Sons: 1992).

Polypeptides and fragments thereof of the disclosure will have one or more biological properties (e.g., in vivo, in vitro or immunological properties) of the native full-length polypeptide. Non-functional polypeptides are also included within the scope of the disclosure because they may be useful, for example, as antagonists of the functional polypeptides. The biological properties of analogues, fragments, or derivatives relative to wild type may be determined, for example, by means of biological assays.

Polypeptides, including analogues, fragments and derivatives, can be prepared synthetically (e.g., using the well known techniques of solid phase or solution phase peptide synthesis). Preferably, solid phase synthetic techniques are employed. Alternatively, the polypeptides of the disclosure can be prepared using well known genetic engineering techniques, as described infra.

The *Pneumocystis murina* polypeptide analogues include those polypeptides having the amino acid sequence, wherein one or more of the amino acids are substituted with another amino acid which substitutions do not substantially alter the biological activity of the molecule.

According to the disclosure, the polypeptides of the disclosure produced recombinantly or by chemical synthesis and fragments or other derivatives or analogues thereof, including fusion proteins, may be used as an immunogen to generate antibodies that recognize the polypeptides.

The term “antigenic” as used herein refers to a molecule capable of specifically interacting with an antigen recognition molecule of the immune system, such as an immunoglobulin (antibody) or T cell antigen receptor. An antigenic amino acid sequence contains at least about 5, and preferably at least about 10, amino acids. An antigenic portion of a molecule can be the portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

The term “antibody” is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567, as well as antigen binding portions of antibodies, including Fab, F(ab') .sub.2 and F(v) (including single chain antibodies). Accordingly, the phrase “antibody molecule” in its various grammatical forms as used herein contemplates both an intact immunoglobulin molecule and an immunologically active portion of an immunoglobulin molecule containing the antibody combining site. An “antibody combining site” is that structural portion of an antibody molecule comprised of heavy and light chain variable and hypervariable regions that specifically binds an antigen.

Exemplary antibody molecules are intact immunoglobulin molecules, substantially intact immunoglobulin molecules and those portions of an immunoglobulin molecule that contain the paratope, including those portions known in the art as Fab, Fab', F(ab').sub.2 and F(v), which portions are preferred for use in the therapeutic methods described herein.

Fab and $F(ab')_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab') .sub.2 portions followed by reduction with mercaptoethanol of the disulfide bonds linking the two heavy chain portions, and followed by alkylation of the resulting protein mercaptan with a reagent such as iodoacetamide. An antibody containing intact antibody molecules is preferred herein.

The phrase "monoclonal antibody" in its various grammatical forms and as used herein refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The term "adjuvant" as used herein refers to a compound or mixture that enhances the immune response to an antigen. An adjuvant can serve as a tissue depot that slowly releases the antigen and also as a lymphoid system activator that non-specifically enhances the immune response (Hood et al., in Immunology, p. 384, Second Ed., Benjamin/Cummings, Menlo Park, Calif. (1984). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (Bacille Calmette-Guerin) and *Corynebacterium parvum*. Preferably, the adjuvant is pharmaceutically acceptable.

Various procedures known in the art may be used for the production of polyclonal antibodies to the polypeptides and fragments thereof of the disclosure. For the production of an antibody(ies), various host animals can be immunized by injection with the polypeptide of the disclosure, including but not limited to rabbits, mice, rats, sheep, goats, etc. In one embodiment, a polypeptide of the disclosure can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies directed toward a polypeptide of the disclosure, any technique that provides for the production of antibody molecules by continuous cell lines in culture may be used. These include but are not limited to the hybridoma technique originally developed by Kohler et al., (1975) Nature, 256: 495-497, the trioma technique, the human B-cell hybridoma technique (Kozbor et al., (1983) Immunology Today, 4: 72), and the EBV-hybridoma technique to produce human monoclonal antibodies (Cole et al., (1985) in Monoclonal Antibodies and Cancer Therapy, pp. 77-96, Alan R. Liss, Inc.). Immortal, antibody-producing cell lines can be created by techniques other than fusion, such as direct transformation of B lymphocytes with oncogenic DNA, or transfection with Epstein-Barr virus. See, e.g., U.S. Pat. Nos. 4,341,761; 4,399,121; 4,427,783; 4,444,887; 4,451,570; 4,466,917; 4,472,500; 4,491,632; and 4,493,890.

Antibody fragments, which contain the idiotype of the antibody molecule, can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA, "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present disclosure. For example, to select antibodies that recognize a specific epitope of a polypeptide of the disclosure, one may assay generated hybridomas for a product that binds to a fragment of a polypeptide of the disclosure containing such epitope.

The disclosure also covers diagnostic and prognostic methods to detect the presence of *Pneumocystis* sp. using a polypeptide of the disclosure and/or antibodies that bind to the polypeptide of the disclosure and kits useful for diagnosis and prognosis of *Pneumocystis* sp. infections.

Diagnostic and prognostic methods will generally be conducted using a biological sample obtained from a subject. The term "sample" as used herein refers to an animal's tissue or fluid suspected of containing a *Pneumocystis* species, such as *P. jirovecii*, or its polynucleotides or its polypeptides. Examples of such tissue or fluids include, but not limited to, plasma, serum, fecal material, urine, lung, heart, skeletal muscle, stomach, intestines, and in vitro cell culture constituents.

The disclosure provides methods for detecting the presence of a polypeptide of the disclosure in a sample, with the following steps: (a) contacting a sample suspected of containing a polypeptide of the disclosure with an antibody (preferably bound to a solid support) that specifically binds to an SPD-1 polypeptide, or to fragments thereof, of the disclosure under conditions which allow for the formation of reaction complexes comprising the antibody and the polypeptide of the disclosure; and (b) detecting the formation of reaction complexes comprising the antibody and polypeptide of the disclosure in the sample, wherein detection of the formation of reaction complexes indicates the presence of the polypeptide of the disclosure in the sample.

Preferably, the antibody used in this method is derived from an affinity-purified polyclonal antibody, and more preferably a monoclonal antibody. In addition, it is preferable for the antibody molecules used herein be in the form of Fab, Fab', $F(ab')_2$ or F(v) portions or whole antibody molecules.

Particularly preferred methods for detecting *P. jirovecii* based on the above method include enzyme linked immunosorbent assays, radioimmunoassays, immunoradiometric assays and immunoenzymatic assays, including sandwich assays using monoclonal and/or polyclonal antibodies.

Three such procedures that are especially useful utilize either polypeptide of the disclosure (or a fragment thereof) labelled with a detectable label, antibody Ab.sub.1 labelled with a detectable label, or antibody Ab.sub.2 labelled with a detectable label. The procedures may be summarized by the following equations wherein the asterisk indicates that the particle is labelled and "AA" stands for the polypeptide of the disclosure: $AA^*+Ab_1=AA^*Ab_1$ (A.) $AA+Ab^*_1=AAAb_1^*$(B.) $AA+Ab_1+Ab_2^*=Ab_1AAAb_2^*$(C.)

The procedures and their application are all familiar to those skilled in the art and accordingly may be utilized within the scope of the present disclosure. The "competitive" procedure, Procedure A, is described in U.S. Pat. Nos. 3,654,090 and 3,850,752. Procedure B is representative of well-known competitive assay techniques. Procedure C, the "sandwich" procedure, is described in U.S. Pat. Nos. RE 31,006 and 4,016,043. Still other procedures are known, such as the "double antibody" or "DASP" procedure, and can be used.

In each instance, the polypeptide of the disclosure form complexes with one or more antibody(ies) or binding partners and one member of the complex is labelled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This reaction is because $Ab_1$, raised in one mammalian species, has been used in another species as an antigen to raise the antibody, $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary antibody, and $Ab_2$ will be referred to as a secondary or anti-$Ab_1$ antibody.

The labels most commonly employed for these studies are radioactive elements, enzymes, chemicals that fluoresce when exposed to ultraviolet light, and others. Examples of fluorescent materials capable of being utilized as labels include fluorescein, rhodamine and auramine. A particular detecting material is anti-rabbit antibody prepared in goats and conjugated with fluorescein through an isothiocyanate. Examples of preferred isotope include $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. The radioactive label can be detected by any of the currently available counting procedures. While many enzymes can be used, examples of preferred enzymes are peroxidase, β-glucuronidase, β-D-glucosidase, β-D-galactosidase, urease, glucose oxidase plus peroxidase and alkaline phosphatase. Enzymes are conjugated to the selected particle by reaction with bridging molecules such as carbodiimides, diisocyanates, glutaraldehyde and the like. Enzyme labels can be detected by any of the presently utilized colorimetric, spectrophotometric, fluorospectrophotometric, amperometric or gasometric techniques. U.S. Pat. Nos. 3,654,090; 3,850,752; and 4,016,043 are referred to by way of example for their disclosure of alternate labelling material and methods.

The disclosure also provides a method of detecting antibodies to a polypeptide of the disclosure in biological samples, using the following steps: (a) providing a polypeptide of the disclosure or a fragment thereof; (b) incubating a biological sample with said polypeptide of the disclosure under conditions which allow for the formation of an antibody-antigen complex; and (c) determining whether an antibody-antigen complex with the polypeptide of the disclosure is formed.

In another embodiment of the disclosure there are provided in vitro methods for evaluating the level of antibodies to a polypeptide of the disclosure in a biological sample using the following steps: (a) detecting the formation of reaction complexes in a biological sample according to the method noted above; and (b) evaluating the amount of reaction complexes formed, which amount of reaction complexes corresponds to the level of polypeptide of the disclosure in the biological sample.

Further there are provided in vitro methods for monitoring therapeutic treatment of a disease associated with a *Pneumocystis* spp. in an animal host by evaluating, as described above, the levels of antibodies to a polypeptide of the disclosure in a series of biological samples obtained at different time points from an animal host undergoing such therapeutic treatment.

The present disclosure further provides methods for detecting the presence or absence of a *Pneumocystis* spp in a biological sample by: (a) bringing the biological sample into contact with a polynucleotide probe or primer of polynucleotide of the disclosure under suitable hybridizing conditions; and (b) detecting any duplex formed between the probe or primer and nucleic acid in the sample.

According to one embodiment of the disclosure, detection of *Pneumocystis* spp may be accomplished by directly amplifying polynucleotide sequences from biological sample, using known techniques and then detecting the presence of polynucleotide of the disclosure sequences.

In one form of the disclosure, the target nucleic acid sequence is amplified by PCR and then detected using any of the specific methods mentioned above. Other useful diagnostic techniques for detecting the presence of polynucleotide sequences include, but are not limited to: 1) allele-specific PCR; 2) single stranded conformation analysis; 3) denaturing gradient gel electrophoresis; 4) RNase protection assays; 5) the use of proteins which recognize nucleotide mismatches, such as the *E. coli* mutS protein; 6) allele-specific oligonucleotides; and 7) fluorescent in situ hybridization.

In addition to the above methods polynucleotide sequences may be detected using conventional probe technology. When probes are used to detect the presence of the desired polynucleotide sequences, the biological sample to be analyzed, such as blood or serum, may be treated, if desired, to extract the nucleic acids. The sample polynucleotide sequences may be prepared in various ways to facilitate detection of the target sequence; e.g. denaturation, restriction digestion, electrophoresis or dot blotting. The targeted region of the sample polynucleotide sequence usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Sample polynucleotide sequences and probes are incubated under conditions that promote stable hybrid formation of the target sequence in the probe with the putative desired polynucleotide sequence in the sample. Preferably, high stringency conditions are used in order to prevent false positives.

Detection, if any, of the resulting hybrid is usually accomplished by the use of labelled probes. Alternatively, the probe may be unlabeled, but may be detectable by specific binding with a ligand that is labelled, either directly or indirectly. Suitable labels and methods for labelling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labelled moiety.

It is also contemplated within the scope of this disclosure that the nucleic acid probe assays of this disclosure may employ a cocktail of nucleic acid probes capable of detecting the desired polynucleotide sequences of this disclosure. Thus, in one example to detect the presence of polynucleotide sequences of this disclosure in a cell sample, more than one probe complementary to a polynucleotide sequences is employed and in particular the number of different probes is alternatively 2, 3, or 5 different nucleic acid probe sequences.

The polynucleotide sequences described herein (preferably in the form of probes) may also be immobilized to a solid phase support for the detection of a *Pneumocystis* species, including but not limited to *P. jirovecii*. Alternatively the polynucleotide sequences described herein will form part of a library of DNA molecules that may be used to detect simultaneously a number of different genes from *Pneumocystis* species, such as *P. jirovecii*. In a further alternate form of the disclosure polynucleotide sequences described herein together with other polynucleotide sequences (such as from other bacteria or viruses) may be immobilized on a solid support in such a manner permitting identification of the presence of a *Pneumocystis* species, such as *P. jirovecii* and/or any of the other polynucleotide sequences bound onto the solid support.

Techniques for producing immobilized libraries of DNA molecules have been described in the art. Generally, most prior art methods describe the synthesis of single-stranded nucleic acid molecule libraries, using for example masking techniques to build up various permutations of sequences at the various discrete positions on the solid substrate. U.S. Pat. No. 5,837,832 describes an improved method for producing DNA arrays immobilized to silicon substrates based on very large scale integration technology. In particular, U.S. Pat. No. 5,837,832 describes a strategy called "tiling" to synthesize specific sets of probes at spatially defined locations on a substrate that may be used to produce the immobilized DNA libraries of the present disclosure. U.S. Pat. No. 5,837,832 also provides references for earlier techniques that may also be used. Thus polynucleotide sequence probes may be synthesized in situ on the surface of the substrate.

Alternatively, single-stranded molecules may be synthesized off the solid substrate and each pre-formed sequence applied to a discrete position on the solid substrate. For example, polynucleotide sequences may be printed directly onto the substrate using robotic devices equipped with either pins or pizo electric devices.

The library sequences are typically immobilized onto or in discrete regions of a solid substrate. The substrate may be porous to allow immobilization within the substrate or substantially non-porous, in which case the library sequences are typically immobilized on the surface of the substrate. The solid substrate may be made of any material to which polypeptides can bind, either directly or indirectly. Examples of suitable solid substrates include flat glass, silicon wafers, mica, ceramics and organic polymers such as plastics, including polystyrene and polymethacrylate. It may also be possible to use semi-permeable membranes such as nitrocellulose or nylon membranes, which are widely available. The semi-permeable membranes may be mounted on a more robust solid surface such as glass. The surfaces may optionally be coated with a layer of metal, such as gold, platinum or other transition metal.

Preferably, the solid substrate is generally a material having a rigid or semi-rigid surface. In preferred embodiments, at least one surface of the substrate will be substantially flat, although in some embodiments it may be desirable to physically separate synthesis regions for different polymers with, for example, raised regions or etched trenches. It is also preferred that the solid substrate is suitable for the high density application of DNA sequences in discrete areas of typically from 50 to 100 μm, giving a density of 10000 to 40000 dots/$cm^{-2}$.

The solid substrate is conveniently divided up into sections. This may be achieved by techniques such as photoetching, or by the application of hydrophobic inks, for example Teflon®-based inks (Cel-Line®, USA).

Discrete positions, in which each different member of the library is located may have any convenient shape, e.g., circular, rectangular, elliptical, wedge-shaped, etc.

Attachment of the polynucleotide sequences to the substrate may be by covalent or non-covalent means. The polynucleotide sequences may be attached to the substrate via a layer of molecules to which the library sequences bind. For example, the polynucleotide sequences may be labelled with biotin and the substrate coated with avidin and/or streptavidin. A convenient feature of using biotinylated polynucleotide sequences is that the efficiency of coupling to the solid substrate can be determined easily. Since the polynucleotide sequences may bind only poorly to some solid substrates, it is often necessary to provide a chemical interface between the solid substrate (such as in the case of glass) and the nucleic acid sequences. Examples of suitable chemical interfaces include hexaethylene glycol. Another example is the use of polylysine coated glass, the polylysine then being chemically modified using standard procedures to introduce an affinity ligand. Other methods for attaching molecules to the surfaces of solid substrate by the use of coupling agents are known in the art, see for example WO98/49557.

Binding of complementary polynucleotide sequences to the immobilized nucleic acid library may be determined by a variety of means such as changes in the optical characteristics of the bound polynucleotide sequence (i.e. by the use of ethidium bromide) or by the use of labelled nucleic acids, such as polypeptides labelled with fluorophores. Other detection techniques that do not require the use of labels include optical techniques such as optoacoustics, reflectometry, ellipsometry and surface plasmon resonance (see WO97/49989).

Thus, the present disclosure provides a solid substrate having immobilized thereon at least one polynucleotide of the present disclosure, preferably two or more different polynucleotide sequences of the present disclosure.

The present disclosure provides the amino acid sequences described herein or fragments thereof or antibodies that bind the amino acid sequences or the polynucleotide sequences described herein in a therapeutically effective amount admixed with a pharmaceutically acceptable carrier, diluent, or excipient.

The phrase "therapeutically effective amount" is used herein to mean an amount sufficient to reduce by at least about 15%, preferably by at least 50%, more preferably by at least 90%, and most preferably prevent, a clinically significant deficit in the activity, function and response of the animal host. Alternatively, a therapeutically effective amount is sufficient to cause an improvement in a clinically significant condition in the animal host.

The phrase "pharmaceutically acceptable" refers to molecular entities and compositions that are physiologically tolerable and do not typically produce an allergic or similarly untoward reaction, such as gastric upset and the like, when administered to an animal. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or saline solutions and aqueous dextrose and glycerol solutions are preferably employed as carriers, particularly for injectable solutions. Suitable pharmaceutical carriers are described in Martin, Remington's Pharmaceutical Sciences, 18th Ed., Mack Publishing Co., Easton, Pa., (1990).

The present disclosure, therefore, provides the surprising result that a surface protein of the murine fungal pathogen *P. murina* can be used to generate an immune response in a recipient animal or human that provides prophylactic anti-*Pneumocystis* protection and an anti-fungal activity in subjects already infected. Further, the disclosure provides novel polypeptides or peptides derived from the *P. murina* surface protein Surface Peptidase 1 (SPD-1) that are also useful, alone or in combination with the SPD-1 polypeptide, in compositions and methods for the generation of an anti-*Pneumocystis* immune reaction by a recipient subject. The compositions and methods of the disclosure, therefore, provide advantageous alternatives to currently available immunogenic determinants for the treatment or prevention of fungal pneumonia, most advantageously against the human pathogen *P. jirovecii*.

The disclosure provides for the identification of surface exposed immunogens of a surface protein of *P. murina* that can induce an immune response directed also against the most common human fungal pneumonia causative agents, *P. jirovecii*. In particular, the exposed immunogenic peptides were identified by in situ labeling of SPD-1, fragmenting the polypeptide, and sequencing the resulting labeled fragments by mass spectrometry. By this means two most advantageous peptide fragments, one consisting of the N-terminal 230 amino acid residues and the other of the C-terminal 450 residues proved able to induce a sustained immune response including the generation of anti-SPD-1-specific antibodies when administered to a recipient animal. The nucleotide sequences encoding these two immunogenic peptides were inserted into expression vectors and expressed in cultured cell lines to provide sufficient material to be administered as a therapeutic amount in an infected animal, thereby reducing the *Pneumocystis* load.

It is contemplated, therefore, that the immunogenic compositions of the disclosure can comprise a pharmaceutically acceptable composition including the isolated polypeptide according to the sequence SEQ ID NO: 1, either alone or in combination with isolated immunogenic peptides derived from the SPD-1 polypeptide of SEQ ID NO: 1. Thus, for example, the immunogenic composition can comprise the polypeptide SEQ ID NO: 1 with the peptides SEQ ID NO: 2 and SEQ ID NO: 4 alone or in combination. Additional compositions may be such as, but not intended to be limiting, SEQ ID NO: 1 with any combination of the peptides selected from the group according to SEQ ID NOs 2, 4, 6, 7, and 10-40.

In a more specific form of the disclosure there are provided pharmaceutical compositions comprising therapeutically effective amounts of the amino acid sequences described herein or an analogue, fragment or derivative product thereof or antibodies thereto together with pharmaceutically acceptable diluents, preservatives, solubilizes, emulsifiers, adjuvants and/or carriers. Such compositions include diluents of various buffer content (e.g., Tris-HCl, acetate, phosphate), pH and ionic strength and additives such as detergents and solubilizing agents (e.g., Tween® 80, Polysorbate 80), anti-oxidants (e.g., ascorbic acid, sodium metabisulfite), preservatives (e.g., Thimersol, benzyl alcohol) and bulking substances (e.g., lactose, mannitol). The material may be incorporated into particulate preparations of polymeric compounds such as polylactic acid, polyglycolic acid, etc. or into liposomes, Hylauronic acid may also be used. Such compositions may influence the physical state, stability, rate of in vivo release, and rate of in vivo clearance of the present proteins and derivatives. See, e.g., Martin, Remington's Pharmaceutical Sciences, 18th Ed. (1990, Mack Publishing Co., Easton, Pa. 18042) pages 1435-1712 that are herein incorporated by reference. The compositions may be prepared in liquid form, or may be in dried powder, such as lyophilized form.

While it is contemplated that the peptides according to the sequences of SEQ ID NOs: 2, 4, 6, 7, and 10-40 may be generated by well known chemical synthesis procedures, it can further be advantageous to generate such peptides by recombinant nucleic acid technologies whereby the nucleotide sequences encoding the peptides may be inserted into a suitable expression vector, transformed into a cell line such as a mammalian or insect cultured cell line, expressed therefrom and then subjected to isolation protocols well-known in the art. The expressed peptides may then by purified before inclusion in the immunogenic compositions of the disclosure. It is further understood that the nucleotide sequences encoding the SPD-1 polypeptide or fragments thereof may be codon-optimized for advantageous expression of the desired amino acid sequence by the host cell line It will be appreciated that pharmaceutical compositions provided accordingly to the disclosure may be administered by any means known in the art. Preferably, the pharmaceutical compositions for administration can be administered by injection, orally, or by the pulmonary, or nasal route. The amino acid sequences described herein or antibodies derived therefrom are more preferably delivered by intravenous, intraarterial, intraperitoneal, intramuscular, or subcutaneous routes of administration. Alternatively, the amino acid sequence described herein or antibodies derived therefrom, properly formulated, can be administered by nasal or oral administration.

The disclosure also includes kits for screening animals suspected of being infected with a *Pneumocystis* species. In accordance with the testing techniques discussed above, such kits can contain at least a labelled version of one of the amino acid sequences described herein or its binding partner, for instance an antibody specific thereto, and directions depending upon the method selected, e.g., "competitive," "sandwich," "DASP" and the like. Alternatively, such kits can contain at least a polynucleotide sequence complementary to a portion of one of the polynucleotide sequences described herein together with instructions for its use. The kits may also contain peripheral reagents such as buffers, stabilizers, etc.

Accordingly, a test kit for the demonstration of the presence of a *Pneumocystis* species or for the administration of the immunogen compositions of the disclosure to a recipient animal or human and may contain the following: (a) a predetermined amount of at least one labelled immunochemically reactive component obtained by the direct or indirect attachment of one of the amino acid sequences described herein or a specific binding partner thereto, to a detectable label; (b) other reagents; and (c) directions for use of said kit.

More specifically, the diagnostic test kit may contain: (a) a known amount of one of the amino acid sequences described herein as described above (or a binding partner) generally bound to a solid phase to form an immunosorbent, or in the alternative, bound to a suitable tag, or there are a plural of such end products, etc; (b) if necessary, other reagents; and (c) directions for use of said test kit.

In a further variation, the test kit may contain: (a) a labeled component which has been obtained by coupling one of the amino acid sequences described herein to a detectable label; (b) one or more additional immunochemical reagents of which at least one reagent is a ligand or an immobilized ligand, which ligand is selected from the group consisting of: (i) a ligand capable of binding with the labelled component (a); (ii) a ligand capable of binding with a binding partner of the labelled component (a); (iii) a ligand capable of binding with at least one of the component(s) to be determined; or (iv) a ligand capable of binding with at least one of the binding partners of at least one of the component(s) to be determined; and (c) directions for the performance of a protocol for the detection and/or determination of one or more components of an immunochemical reaction between one of the amino acid sequences described herein and a specific binding partner thereto.

One aspect of the disclosure, therefore, encompasses embodiments of an immunogenic composition comprising at least one immunogenic component selected from the group consisting of: (a) an isolated Surface Peptidase 1 (SPD-1) polypeptide of *Pneumocystis murina* and having an amino acid sequence having at least 90% similarity to the sequence according to SEQ ID NO: 1 and (b) at least one immunogenic fragment of an SPD-1 polypeptide of *Pneumocystis murina* wherein said at least one fragment has an amino acid sequence of at least 90% similarity to an amino acid sequence selected from the group consisting of: SEQ ID NOs: 2, 4, 6, 7, and 10-40, and wherein the composition further comprises a pharmaceutically acceptable carrier and is formulated to induce an anti-*Pneumocystis* immune response when administered to an animal or human recipient.

In some embodiments of this aspect of the disclosure, the pharmaceutically acceptable carrier can comprise an adjuvant.

In some embodiments of this aspect of the disclosure, the SPD-1 polypeptide can have an amino acid sequence according to SEQ ID NO: 1.

In some embodiments of this aspect of the disclosure, the at least one immunogenic fragment of the SPD-1 polypeptide can have an amino acid sequence selected from the group consisting of: SEQ ID NOs: 2, 4, 6, 7, and 10-40.

In some embodiments of this aspect of the disclosure, the at least one immunogenic fragment of the SPD-1 polypeptide can have an amino acid sequence selected from SEQ ID NO: 2 and SEQ ID NO: 4.

Another aspect of the disclosure encompasses embodiments of an antibody or fragment thereof that can selectively bind to an antigenic region of *Pneumocystis murina* Surface Peptidase 1 (SPD-1).

In some embodiments of this aspect of the disclosure, the antigenic region of the SPD-1 can have an amino acid sequence having at least 90% similarity to an amino acid sequence selected from the group consisting of: SEQ ID NOs: 1, 2, 4, 6, 7, and 10-40.

In some embodiments of this aspect of the disclosure, the antigenic region of the SPD-1 can have an amino acid sequence selected from the group consisting of: SEQ ID NOs: 1, 2, 4, 6, 7, and 10-40.

Yet another aspect of the disclosure encompasses embodiments of an isolated Surface Peptidase 1 (SPD-1) polypeptide of *Pneumocystis murina* having an amino acid sequence of at least 90% similarity to the sequence according to SEQ ID NO: 1, or an immunogenic fragment thereof.

In some embodiments of this aspect of the disclosure, the immunogenic fragment has an amino acid sequence having at least 90% similarity to an amino acid sequence selected from the group consisting of: SEQ ID NOs: 2, 4, 6, 7, and 10-40.

In some embodiments of this aspect of the disclosure, the at least one immunogenic fragment can have an amino acid sequence selected from the group consisting of: SEQ ID NOs: 2, 4, 6, 7, and 10-40.

In some embodiments of this aspect of the disclosure, the at least one immunogenic fragment can have an amino acid sequence selected from SEQ ID NO: 2 and SEQ ID NO: 4.

Still another aspect of the disclosure encompasses embodiments of an isolated nucleic acid having a nucleotide sequence encoding a Surface Peptidase 1 (SPD-1) polypeptide of *Pneumocystis murina*, or an immunogenic fragment thereof.

In some embodiments of this aspect of the disclosure, the nucleic acid can have a nucleotide sequence encoding an amino acid sequence having at least 90% similarity to an amino acid sequence selected from the group consisting of: SEQ ID NOs: 1, 2, 4, 6, 7, and 10-40.

In some embodiments of this aspect of the disclosure, the nucleic acid sequence can be hybridizable under high stringency conditions to a nucleotide sequence selected from the group consisting of: SEQ ID NOs: 3, 5, and 9.

In some embodiments of this aspect of the disclosure, the nucleic acid sequence can be operatively inserted into an expression vector.

In some embodiments of this aspect of the disclosure, the nucleic acid sequence can be an artificial nucleic acid comprising codons selected for optimal expression of the polypeptide by a eukaryotic cell.

Still yet another aspect of the disclosure encompasses embodiments of a method of generating an immune response to a *Pneumocystis* infection in an animal comprising administering to said animal an immunogenic composition comprising at least one immunogenic component selected from the group consisting of: (a) an isolated Surface Peptidase 1 (SPD-1) polypeptide of *Pneumocystis murina* and having an amino acid sequence having at least 90% similarity to the sequence according to SEQ ID NO: 1 and (b) at least one immunogenic fragment of an SPD-1 polypeptide of *Pneumocystis murina* wherein said at least one fragment has an amino acid sequence of at least 90% similarity to an amino acid sequence selected from the group consisting of: SEQ ID NOs: 2, 4, 6, 7, and 10-40, and wherein the composition further comprises a pharmaceutically acceptable carrier and is formulated to induce an anti-*Pneumocystis* immune response when administered to an animal or human recipient.

In some embodiments of this aspect of the disclosure, the *Pneumocystis* infection in a human and the infectious agent can be *P. jirovecii.*

Yet another aspect of the disclosure encompasses embodiments of a kit comprising a container containing a therapeutic amount of an immunogenic composition according to claim 1 and instructions directing the use of the composition in generating an immune response in a recipient animal or human.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

The following examples are further illustrative of the present disclosure. These examples are not intended to limit the scope of the present disclosure and provide further understanding of the disclosure.

Example 1

Exemplary embodiments of the present disclosure include the use of the *Pneumocystis murina* Surface Peptidase 1 (SPD-1) hypothetical protein PNEG_01848 of 1069 amino acids (SEQ ID NO: 1), or fragments thereof. For example, fragments include exposed portions of the protein. Additional embodiments of the compositions of the disclosure may include any number of other surface proteins, or fragments thereof. Such additional embodiments include proteins or fragments as listed in Table 1.

TABLE 1

| Polypeptide | SEQ ID NO: |
|---|---|
| SPD-1 | (SEQ ID NO: 1) |
| SPD-1 N230 | (SEQ ID NO: 2) |
| SPD-1 C450 | (SEQ ID NO: 4) |
| N-terminal peptide of SPD-1 | (SEQ ID NO: 6) |
| C-terminal of SPD-1 | (SEQ ID NO: 7) |
| mature SPD-1 | (SEQ ID NO: 8) |
| peptides induce a T-cell response | (SEQ ID NOs: 10-20) |
| peptides induce a B-cell response | (SEQ ID NOs: 21-25) |
| additional peptides | (SEQ ID NOs: 26-40) |
| Pneumocystis antigen A12 PNEG_02212 | (SEQ ID NO: 41) |
| *Pneumocystis murina* HSP60 PNEG_02587 | (SEQ ID NO: 42) |
| *Pneumocystis murina* major surface glycoprotein-like PNEG_00002 | (SEQ ID NO: 43) |
| *Pneumocystis murina* hypothetical protein PNEG_00502 | (SEQ ID NO: 44) |
| *Pneumocystis murina* major surface glycoprotein-RELATED PNEG_00831 | (SEQ ID NO: 46) |
| *Pneumocystis murina* hypothetical protein PNEG_01105 | (SEQ ID NO: 47) |
| *Pneumocystis murina* hypothetical protein PNEG_01231 | (SEQ ID NO: 49) |
| *Pneumocystis murina* major surface glycoprotein family PNEG_01377 | (SEQ ID NO: 50) |
| *Pneumocystis murina* hypothetical protein PNEG_01746 | (SEQ ID NO: 52) |
| *Pneumocystis murina* major surface glycoprotein PNEG_01847 | (SEQ ID NO: 53) |
| *Pneumocystis murina* hypothetical protein PNEG_03149 | (SEQ ID NO: 54) |
| *Pneumocystis murina* hypothetical protein PNEG_03306 | (SEQ ID NO: 56) |
| *Pneumocystis murina* hypothetical protein PNEG_03454 | (SEQ ID NO: 57) |
| *Pneumocystis murina* major surface glycoprotein PNEG_03599 | (SEQ ID NO: 59) |
| *Pneumocystis murina* major surface glycoprotein PNEG_00001 | (SEQ ID NO: 60) |
| *Pneumocystis murina* hypothetical protein PNEG_00053 | (SEQ ID NO: 61) |
| *Pneumocystis murina* major surface glycoprotein PNEG_00563 | (SEQ ID NO: 62) |
| *Pneumocystis murina* major surface glycoprotein family PNEG_00564 | (SEQ ID NO: 63) |
| *Pneumocystis murina* hypothetical protein PNEG_00674 | (SEQ ID NO: 64) |
| *Pneumocystis murina* major surface glycoprotein PNEG_00053 | (SEQ ID NO: 65) |
| *Pneumocystis murina* major surface glycoprotein-like PNEG_02613 | (SEQ ID NO: 66) |
| *Pneumocystis murina* major surface glycoprotein PNEG_02990 | (SEQ ID NO: 67) |
| *Pneumocystis murina* major surface glycoprotein PNEG_03598 | (SEQ ID NO: 68) |

Embodiments of the present disclosure may comprise oligonucleotides. For example, optimized oligonucleotides may be, but are not limited to a codon-optimized nucleotide sequence for SPD-1 N230 (SEQ ID NO: 3), a codon-optimized nucleotide sequence for SPD-1 C450 (SEQ ID NO: 5), a codon-optimized nucleotide sequence for matured SPD-1 (SEQ ID NO: 9), a codon-optimized nucleotide sequence for *Pneumocystis murina* hypothetical protein PNEG_00502 (SEQ ID NO: 45), a codon-optimized nucleotide sequence for *Pneumocystis murina* hypothetical protein PNEG_01105 (SEQ ID NO: 48), a codon-optimized nucleotide sequence for *Pneumocystis murina* hypothetical protein PNEG_01746 (SEQ ID NO: 52), a codon optimized nucleotide sequence for *pneumocystis murina* hypothetical protein PNEG_03149 (SEQ ID NO: 55), and a codon optimized nucleotide sequence for *pneumocystis murina* hypothetical protein PNEG_03454 (SEQ ID NO: 58).

Example 2

The disclosure provides the identification of antigen targets advantageous for use as novel *Pneumocystis* vaccines and therapeutics. To identify these antigens, live *Pneumocystis* organisms were isolated from lung lavage fluid of mice infected with *Pneumocystis*.

Surface components of the retrieved organisms were labelled with sulfo-NHS-LC-biotin, which is cell membrane impermeable and specifically labels primary amine groups such as unmodified N-termini and lysine side chains in proteins and peptides. Under the reaction conditions employed, the native structures of cell surface proteins were preserved. Trypsin was employed to cleave labeled cell surface proteins to generate labeled peptides that were isolated by biotin-avidin affinity purification before liquid chromatography-mass spectrometry (LC-MS) analysis.

Peptide sequences of the surface components were identified by mass spectroscopy. Tandem mass spectral of spectra of peptides were searched against a *Pneumocystis murina* protein database (Broad Institute) using the SEQUEST® algorithm. Peptides identified as being labeled by sulfo-NHS-LC-biotinylation of lysine residue(s) were used to determine cell surface localization of the proteins.

A BLASTp search of peptide sequences was performed to select a candidate surface protein and having low homology with the host proteins. Positive peptides within said surface protein were subsequently selected by binding to mouse immune serum

Example 3

Sodium Dodecyl Sulfate Polyacrylamide Gel Electrophoresis (SDS-Page)

SDS-PAGE analysis of protein was performed using a discontinuous Tris-glycine buffer system. Thirty μl of protein sample were mixed with 10 μl 4× sample treatment buffer (250 mM Tris-HCl (pH 6.0), 8% (w/v) SDS, 200 mM OTT, 40% (v/v) glycerol and 0.04% (w/v) bromophenol blue). Samples were boiled for 5 min immediately prior to loading 10 μl of the sample into wells in the gel. The gel comprised a stacking gel (125 mM Tris-HCl ph 6.8, 4% w/v acrylamide, 0.15% w/v bis-acrylamide and 0.1% w/v SDS) and a separating gel (375 mM Tris-HCl pH 8.8, 12% w/v acrylamide, 0.31% w/v bis-acrylamide and 0.1% SDS). These gels were polymerized by the addition of 0.1% (v/v) TEMED and 0.05% (w/v) freshly prepared ammonium sulfate solution and cast into the mini-Protean® dual slab cell (Bio-Rad, Hercules, Calif.). Samples were run at 150V at room temperature (RT) until the bromophenol blue dye reached the bottom of the gel. Pre-stained molecular weight standards were electrophoresed in parallel with the samples to allow molecular weight estimations. After electrophoresis, the gel was immediately stained using Coomassie Brilliant Blue G250 (Bio-Rad) or subjected to electro-transfer onto nitrocellulose membrane for Western blotting.

Example 4

Western Blot Analysis

Electrophoretic transfer of separated proteins from the SDS-PAGE gel to nitrocellulose membrane was performed using the Towbin transfer buffer system. After electrophoresis, the gel was equilibrated in transfer buffer (25 mM Tris, 192 m/M glycine, 20% v/v methanol, pH 8.3) for 15 min. The proteins in the gel were electro-transferred to nitrocellulose membrane (Protran, Schleicher and Schuell BioScience, Inc., Keene, N.H.) using the mini-Protean® transblot apparatus (Bio-Rad) at 30V overnight at 4° C. The freshly transferred nitrocellulose membrane containing the separated proteins was blocked with 10 ml of Tris-buffered saline (TBS) containing 5% (w/v) skim milk powder for 1 h at room temperature. The membrane was washed with TBS containing 0.1% (v/v) Tween® 20 (TBST) and then incubated with 10 mL mouse anti-his antibody (diluted 5,000-fold with TBST) for 1 h at room temperature. After washing three times for 5 min with TBST, the membrane was incubated with 10 mL goat anti-mouse IgG (whole molecule)-AP diluted 5,000-fold in TBST for 1 hour at room temperature. The membrane was developed using the Alkaline Phosphatase Substrate Kit (Bio-Rad). The development reaction was stopped by washing the membrane with distilled water. The membrane was then dried and scanned for presentation.

Example 5

The surface proteins of purified *P. murina* were biotin labeled and analyzed using LC-MS to determine peptide sequences. The tandem mass spectral data of peptides were then used to query against the NCBI RefSeq protein sequence for fungi and the *P. murina* draft genome database to identify peptides.

A novel vaccine candidate, designated SPD-1, was identified. SPD-1 is a surface protein derived from single suspended *P. murina* cysts that may serve as an antigenic target for vaccine development. The matured form of protein SPD-1 was identified along with several exposed peptide segments of this protein. The N-terminal region of the protein, SPD-1 (N230), and the C-terminal fragment (C450) were expressed in an insect cell line and the recombinant protein was tested as an antigenic target for vaccine development.

Example 6

BALB/c mice were boosted 3 times with 5 μg per mouse of either SPD-1 N230 or C450 plus adjuvant MF-59 by subcutaneous injection. Control mice received an equal volume of adjuvant alone or saline. Three weeks after the last immunization, $CD4^+$ cells were depleted with the intraperitoneally administered anti-CD4 antibody GK1.5. The mice were then challenged with $2\times10^5$ *Pneumocystis* organisms.

CD4 depletion continued as weekly intraperitoneal injections of GK1.5. Mice were sacrificed at indicated timepoints after *Pneumocystis* challenge. Spleen cells, lung cells and serum were harvested. Flow cytometric analysis of immune cells and specific *Pneumocystis* IgG antibody by ELISA performed. Infection burden was measured as real-time PCR for *P. murina* rRNA, expressed as copy number per right lung.

What is claimed:

1. An immunogenic composition comprising an isolated Surface Peptidase 1 (SPD-1) polypeptide of *Pneumocystis murina* and having the sequence according to SEQ ID NO: 1 or an immunogenic fragment thereof, wherein the fragment has an amino acid sequence of at least 90% similarity to an amino acid sequence selected from the group consisting of: SEQ ID NOs: 2 and 4, and wherein the composition further comprises a pharmaceutically acceptable carrier and an adjuvant, wherein the adjuvant is MF-59, and is formulated to induce an anti-*Pneumocystis* immune response when administered to an animal or human recipient.

2. The composition of claim 1, wherein the immunogenic fragment of the SPD-1 polypeptide has an amino acid sequence SEQ ID NOs: 1, 2 or 4.

3. The composition of claim 1, wherein the immunogenic fragment of the SPD-1 polypeptide has the amino acid sequence SEQ ID NO: 2 or SEQ ID NO: 4.

4. A method of generating an immune response to a *Pneumocystis* infection in an animal comprising administering to said animal the immunogenic composition of claim 1.

5. The method of claim 4, wherein the *Pneumocystis* infection is in a human and the infectious agent is *P. jirovecii.*

6. A kit comprising a container containing a therapeutic amount of an immunogenic composition according to claim 1 and instructions directing the use of the composition in generating an immune response in a recipient animal or human.

* * * * *

SEQUENCE LISTING

```
<160> NUMBER OF SEQ ID NOS: 68

<210> SEQ ID NO 1
<211> LENGTH: 1068
<212> TYPE: PRT
<213> ORGANISM: Pneumocystis murina
<220> FEATURE:
<221> NAME/KEY: MISC_FEATURE
<222> LOCATION: (1)..(1068)
<223> OTHER INFORMATION: Pneumocystis murina Surface Peptidase 1 (SPD-1)
      PNEG-01848
<220> FEATURE:
<221> NAME/KEY: MISC_FEATURE
<222> LOCATION: (34)..(60)
<223> OTHER INFORMATION: Putative surface domain
<220> FEATURE:
<221> NAME/KEY: MISC_FEATURE
<222> LOCATION: (34)..(55)
<223> OTHER INFORMATION: Detected peptide sequence
<220> FEATURE:
<221> NAME/KEY: MISC_FEATURE
<222> LOCATION: (141)..(196)
<223> OTHER INFORMATION: Putative surface domain
<220> FEATURE:
<221> NAME/KEY: MISC_FEATURE
<222> LOCATION: (151)..(167)
<223> OTHER INFORMATION: Detected peptide sequence
<220> FEATURE:
<221> NAME/KEY: MISC_FEATURE
<222> LOCATION: (171)..(190)
<223> OTHER INFORMATION: Detected peptide sequence
<220> FEATURE:
<221> NAME/KEY: MISC_FEATURE
<222> LOCATION: (211)..(233)
<223> OTHER INFORMATION: Putative surface domain
<220> FEATURE:
<221> NAME/KEY: MISC_FEATURE
<222> LOCATION: (223)..(233)
<223> OTHER INFORMATION: Detected peptide sequence
<220> FEATURE:
<221> NAME/KEY: MISC_FEATURE
<222> LOCATION: (241)..(263)
<223> OTHER INFORMATION: Putative surface domain
<220> FEATURE:
<221> NAME/KEY: MISC_FEATURE
<222> LOCATION: (246)..(263)
<223> OTHER INFORMATION: Detected peptide sequence
<220> FEATURE:
<221> NAME/KEY: MISC_FEATURE
<222> LOCATION: (403)..(420)
<223> OTHER INFORMATION: Putative surface domain
<220> FEATURE:
<221> NAME/KEY: MISC_FEATURE
<222> LOCATION: (403)..(413)
<223> OTHER INFORMATION: Detected peptide sequence
<220> FEATURE:
<221> NAME/KEY: MISC_FEATURE
<222> LOCATION: (441)..(453)
<223> OTHER INFORMATION: Putative surface domain
<220> FEATURE:
<221> NAME/KEY: MISC_FEATURE
<222> LOCATION: (451)..(457)
<223> OTHER INFORMATION: Detected peptide sequence
<220> FEATURE:
<221> NAME/KEY: MISC_FEATURE
<222> LOCATION: (546)..(590)
<223> OTHER INFORMATION: Putative surface domain
<220> FEATURE:
<221> NAME/KEY: MISC_FEATURE
<222> LOCATION: (551)..(562)
<223> OTHER INFORMATION: Detected peptide sequence
<220> FEATURE:
```

<221> NAME/KEY: MISC_FEATURE
<222> LOCATION: (569)..(585)
<223> OTHER INFORMATION: Detected peptide sequence
<220> FEATURE:
<221> NAME/KEY: MISC_FEATURE
<222> LOCATION: (627)..(646)
<223> OTHER INFORMATION: Putative surface domain
<220> FEATURE:
<221> NAME/KEY: MISC_FEATURE
<222> LOCATION: (629)..(641)
<223> OTHER INFORMATION: Detected peptide sequence
<220> FEATURE:
<221> NAME/KEY: MISC_FEATURE
<222> LOCATION: (743)..(760)
<223> OTHER INFORMATION: Putative surface domain
<220> FEATURE:
<221> NAME/KEY: MISC_FEATURE
<222> LOCATION: (743)..(753)
<223> OTHER INFORMATION: Detecetd peptide sequence

<400> SEQUENCE: 1

```
Met Trp Ser Tyr Phe Ile Phe Phe Ser Leu Ile Phe Leu Leu Lys Thr
1               5                   10                  15

Glu Ser His Ile Ile Gln His Asn Lys Thr Asp His Ile Leu Tyr Lys
            20                  25                  30

Arg Ala Thr Thr Ala Thr Leu Leu Thr Glu Asn Ile Lys Lys Pro Glu
        35                  40                  45

Gly Asp His Tyr Ser Tyr Arg Leu Ile Gln Leu Ser Asn Gly Leu Lys
    50                  55                  60

Thr Leu Leu Ile Ser Tyr Pro Asp Ser Leu Ser Ala Gly Ala Ala Leu
65                  70                  75                  80

Asp Val Lys Val Gly His Phe Ser Asp Pro Asp Asp Ile Pro Gly Val
                85                  90                  95

Ala His Phe Cys Glu His Leu Leu Phe Met Gly Thr Lys Lys Tyr Pro
            100                 105                 110

Gly Glu Asp Asp Phe Ser Glu Tyr Leu Leu Thr His Ala Gly Thr Tyr
        115                 120                 125

Asn Ala Tyr Thr Ser Thr Glu Asp Thr Asn Tyr Phe Phe Ser Val Glu
    130                 135                 140

Pro Lys Ser Phe Glu Lys Ala Leu Asp Met Phe Ser Gln Leu Phe Ile
145                 150                 155                 160

Ser Pro Leu Ile Leu Lys Arg Ser Val Glu Arg Glu Ala His Ala Val
                165                 170                 175

Asp Leu Glu His Lys Lys Asn Leu Gln Asn Asp Ala Trp Arg Leu Phe
            180                 185                 190

Gln Leu Glu Lys Ser Ile Ser Asn Pro Lys Ser Pro Tyr Ser Lys Phe
        195                 200                 205

Gly Thr Gly Asp Tyr Val Thr Leu Val Glu Asn Thr Arg Lys Lys Gly
    210                 215                 220

Ile Asp Ile Ala Ser Val Val Ser Lys Phe Phe Ser Thr Tyr Tyr Ser
225                 230                 235                 240

Ser Asn Leu Met Lys Leu Val Ile Phe Ser Ser Glu Ser Leu Asp Asn
                245                 250                 255

Leu Glu Lys Leu Ala Val Lys Tyr Phe Thr Asp Ile Pro Asn Lys Asn
            260                 265                 270

Leu Glu Val Pro Lys Phe Thr Glu Lys Pro Phe Gly Ala Asp Val Ile
        275                 280                 285

Gly Lys Gln Tyr Trp Tyr Lys Pro Ile Ala Asp Ser Asn Ser Ile Glu
    290                 295                 300
```

-continued

```
Leu Val Phe Pro Ile Asp Thr Gln Arg Met Phe Tyr Lys Ser Ser Pro
305                 310                 315                 320

Ser Asp Tyr Leu Arg His Phe Leu Asp His Arg Ser Tyr Gly Ser Val
                325                 330                 335

Phe Tyr Thr Leu Asn Gln Arg Gly Trp Ile Thr Asp Ile Ser Val Tyr
            340                 345                 350

Ser Glu Tyr Ile Val Ser Glu Thr Asp Ala Leu Arg Ile Asn Ile Gly
        355                 360                 365

Leu Thr Glu Ile Gly Leu Asp Asn Tyr Glu Asp Ile Leu Gly Leu Val
    370                 375                 380

Phe Gln Phe Leu Arg Met Leu Arg Asp Asn Thr Pro Asn Glu Asp Tyr
385                 390                 395                 400

Phe Lys Asp Leu Ile Lys Ile Asp Asp Val Ser Phe Arg Phe Lys Asp
                405                 410                 415

Gln Pro Lys Leu Met Ser Tyr Ala Ser His Leu Ala Ser Val Met Gln
            420                 425                 430

Leu Pro Tyr Ile Glu Asp Val Asp Leu Leu Arg Ser Ser Tyr Leu Ser
        435                 440                 445

Glu Tyr Asp His Lys Gln Phe Ala Lys Leu Leu Ser Val Leu Arg Asp
    450                 455                 460

Asp Asn Tyr Phe Leu Thr Ile Thr Ser Lys Thr Lys Pro Gly Tyr Trp
465                 470                 475                 480

Asp Leu Arg Glu Pro Trp Tyr Gly Ser Glu Tyr Lys Val Asp Val Phe
                485                 490                 495

Ser Gln Thr Leu Leu Glu Lys Thr Arg Lys Asp Asp Leu Asn Ile Ser
            500                 505                 510

Leu Lys Phe Pro Glu Lys Asn Ile Phe Ile Pro Glu Leu Phe Ile Arg
        515                 520                 525

Ala Asn Val Ser Thr His Lys Lys Thr Lys Pro Thr Leu Met Tyr Asn
    530                 535                 540

Asp Thr Arg Leu Arg Tyr Trp Tyr Lys Glu Asp Asp Thr Phe Ser Ile
545                 550                 555                 560

Pro Lys Thr Phe Ile Ser Ala Leu Ile Lys Ile Pro Asp Tyr Ser Ser
                565                 570                 575

Ser Pro Phe Glu Thr Ala His Ser Lys Ile Tyr Leu Asp Met Leu Ile
            580                 585                 590

Asn His Val Ser Thr Gln His Tyr Asn Ala Ile Val Ala Gly Tyr Ser
        595                 600                 605

Leu Thr Ile Ser Ala Ile Asp Ile Gly Ile Tyr Leu Ser Ile Tyr Gly
    610                 615                 620

Phe Ser Asp Lys Ile Leu Leu Leu Leu Asp Lys Val Ile Glu Ser Met
625                 630                 635                 640

Arg Leu Tyr Thr Pro Ser Leu Ala Ser Phe Met Ser Ser Arg Gln Lys
                645                 650                 655

Tyr Leu Tyr Met Tyr Glu Tyr Asp Lys Val Ser Met Pro Tyr Ser Lys
            660                 665                 670

Val Ser Gln Val Ser Leu Ala Phe His Asp Pro Leu Tyr Trp Pro Ser
        675                 680                 685

Ser Glu Met Leu Tyr Ala Ile Asn Ser Thr Thr Tyr Glu Asp Val Gln
    690                 695                 700

Val Phe His Ser Arg Arg Phe Ser Ser Val Phe Thr Glu Val Leu Ala
705                 710                 715                 720

Val Gly Leu Leu Ser Asn Ser Thr Lys Asp Leu Leu Glu Ile Tyr Phe
```

```
                725                 730                 735

Lys Ala Leu Ser Pro Lys Lys Gln Tyr Pro Tyr Gln Ile Leu Pro Ser
            740                 745                 750

Arg Ser Tyr Ile Phe Lys Glu Gly Ser Asn Tyr Ile Tyr Glu Met Ser
        755                 760                 765

Leu Leu Asn Pro Gln Glu Val Asn Ser Ala Ile Leu Tyr Ser Leu Gln
    770                 775                 780

Val Gly Ser Ser Lys Asp Ser Lys Leu Ile Ala Leu Leu Asn Val Leu
785                 790                 795                 800

Phe Ser Leu Ile Arg Ser Arg Val Phe Asn Gln Leu Arg Thr Glu Glu
                805                 810                 815

Gln Leu Ser Tyr Val Val Arg Val Ser Ser Tyr Thr Ser Thr Ala Leu
            820                 825                 830

Met Ser Phe Phe Phe Val Leu Gln Ser Leu Arg Asp Pro Phe Tyr Leu
        835                 840                 845

Glu Gln Arg Ile Asn Ala Phe Leu Tyr Arg Phe Ala Ala Phe Ile Asp
    850                 855                 860

Thr Ile Thr Asp Glu Gln Leu Lys Ser Val Val Asn Thr Leu Leu Pro
865                 870                 875                 880

Leu Phe Ser Gly Arg Tyr Thr Ser Leu Pro Lys Glu Ser Gly Val Tyr
                885                 890                 895

Leu Ala Ser Ile Val Ser Gly Phe Tyr Asp Phe Asp Ile Arg Lys Lys
            900                 905                 910

Ile Tyr Arg Ser Leu Lys Gly Leu Thr Lys Glu Asp Leu Lys Asp Tyr
        915                 920                 925

Phe Tyr Asn Tyr Phe Tyr Pro Asp Ser Ala Thr Arg Lys Lys Leu Ser
    930                 935                 940

Ile His Leu Lys Ser Gln Thr Leu Glu Ser Val Ser Val Arg Asp Phe
945                 950                 955                 960

Ser Pro Arg Arg Leu Gln Tyr Tyr Phe Lys Cys Asn Gly Leu Asp Ile
                965                 970                 975

Ser Leu Glu Asp Leu Ser Asp Leu Ile Glu Ser Ser His Leu Leu Val
            980                 985                 990

Asp Phe Glu Lys Ala Leu Lys Lys  Phe Phe Thr Asn Lys  Tyr Pro His
        995                 1000                1005

Lys Asp  Val Ser Glu Ile Val  Ser Gln Ala Phe Lys  Tyr Leu Lys
    1010                1015                1020

Glu Leu  Tyr Thr Lys Leu Lys  Lys Asp Ala Ile Lys  Asn Tyr Asp
    1025                1030                1035

Ala Gln  His Phe Thr Asp Leu  Thr Thr Phe Lys Asn  Ser Leu Lys
    1040                1045                1050

Leu Ser  Pro Val Pro Leu Pro  Val Met Lys Trp Ser  Ser Tyr Tyr
    1055                1060                1065
```

<210> SEQ ID NO 2
<211> LENGTH: 229
<212> TYPE: PRT
<213> ORGANISM: Artificial sequence
<220> FEATURE:
<223> OTHER INFORMATION: P. murina SPD-1 N230 N-terminal peptide
<220> FEATURE:
<221> NAME/KEY: MISC_FEATURE
<222> LOCATION: (1)..(27)
<223> OTHER INFORMATION: Putative surface domain
<220> FEATURE:
<221> NAME/KEY: MISC_FEATURE
<222> LOCATION: (1)..(22)

<223> OTHER INFORMATION: Detected peptide sequence
<220> FEATURE:
<221> NAME/KEY: MISC_FEATURE
<222> LOCATION: (108)..(163)
<223> OTHER INFORMATION: Putative surface domain
<220> FEATURE:
<221> NAME/KEY: MISC_FEATURE
<222> LOCATION: (118)..(134)
<223> OTHER INFORMATION: Detected peptide sequence
<220> FEATURE:
<221> NAME/KEY: MISC_FEATURE
<222> LOCATION: (138)..(157)
<223> OTHER INFORMATION: Detected peptide sequence
<220> FEATURE:
<221> NAME/KEY: MISC_FEATURE
<222> LOCATION: (178)..(200)
<223> OTHER INFORMATION: Putative surface domain
<220> FEATURE:
<221> NAME/KEY: MISC_FEATURE
<222> LOCATION: (199)..(200)
<223> OTHER INFORMATION: Detected peptide sequence
<220> FEATURE:
<221> NAME/KEY: MISC_FEATURE
<222> LOCATION: (208)..(229)
<223> OTHER INFORMATION: Putative surface domain
<220> FEATURE:
<221> NAME/KEY: MISC_FEATURE
<222> LOCATION: (213)..(229)
<223> OTHER INFORMATION: Detected peptide sequence

<400> SEQUENCE: 2

```
Ala Thr Thr Ala Thr Leu Leu Thr Glu Asn Ile Lys Lys Pro Glu Gly
1               5                   10                  15

Asp His Tyr Ser Tyr Arg Leu Ile Gln Leu Ser Asn Gly Leu Lys Thr
            20                  25                  30

Leu Leu Ile Ser Tyr Pro Asp Ser Leu Ser Ala Gly Ala Ala Leu Asp
        35                  40                  45

Val Lys Val Gly His Phe Ser Asp Pro Asp Asp Ile Pro Gly Val Ala
    50                  55                  60

His Phe Cys Glu His Leu Leu Phe Met Gly Thr Lys Lys Tyr Pro Gly
65                  70                  75                  80

Glu Asp Asp Phe Ser Glu Tyr Leu Leu Thr His Ala Gly Thr Tyr Asn
                85                  90                  95

Ala Tyr Thr Ser Thr Glu Asp Thr Asn Tyr Phe Phe Ser Val Glu Pro
            100                 105                 110

Lys Ser Phe Glu Lys Ala Leu Asp Met Phe Ser Gln Leu Phe Ile Ser
        115                 120                 125

Pro Leu Ile Leu Lys Arg Ser Val Glu Arg Glu Ala His Ala Val Asp
    130                 135                 140

Leu Glu His Lys Lys Asn Leu Gln Asn Asp Ala Trp Arg Leu Phe Gln
145                 150                 155                 160

Leu Glu Lys Ser Ile Ser Asn Pro Lys Ser Pro Tyr Ser Lys Phe Gly
                165                 170                 175

Thr Gly Asp Tyr Val Thr Leu Val Glu Asn Thr Arg Lys Lys Gly Ile
            180                 185                 190

Asp Ile Ala Ser Val Val Ser Lys Phe Phe Ser Thr Tyr Tyr Ser Ser
        195                 200                 205

Asn Leu Met Lys Leu Val Ile Phe Ser Ser Glu Ser Leu Asp Asn Leu
    210                 215                 220

Glu Lys Leu Ala Val
225
```

<210> SEQ ID NO 3

<211> LENGTH: 693
<212> TYPE: DNA
<213> ORGANISM: Artificial sequence
<220> FEATURE:
<223> OTHER INFORMATION: Codon optimized nucleotide sequence encoding P. murina SPD-1 N230 peptide

<400> SEQUENCE: 3

```
gctaccactg ccacactgct caccgagaac atcaagaagc ctgaaggtga ccactactcc     60

tacaggctca tccagttgtc taacggcctg aagaccttgc tgatctcata cccagactca    120

ctctcggctg gcgctgcctt ggatgtgaag gtcggacact tctccgaccc agacgatatc    180

ccaggagtgg ctcacttctg cgagcacctc ttgttcatgg gtactaagaa gtaccccggc    240

gaggacgatt tctctgaata cctgctcacc cacgctggaa cttacaacgc ctacaccagc    300

actgaggata ccaactactt cttctcagtc gagcccaagt cgttcgaaaa ggctctggac    360

atgttctccc agctcttcat ctctcctctg atcctcaaga ggtccgttga gagagaagct    420

cacgccgtgg atttggagca caagaagaac ctgcagaacg acgcctggcg tctgttccaa    480

ctcgaaaagt ccatctctaa ccccaagtcc ccttactcta agttcggtac aggcgattac    540

gttaccctgg tggagaacac tcgcaagaag ggtatcgaca tcgctagcgt ggtctcaaag    600

ttcttctcaa cttactactc ctctaacttg atgaagctgg tcatcttctc ctcagagtcc    660

ctcgataact tggaaaagct ggccgtctaa tga                                 693
```

<210> SEQ ID NO 4
<211> LENGTH: 442
<212> TYPE: PRT
<213> ORGANISM: Artificial sequence
<220> FEATURE:
<223> OTHER INFORMATION: P.murina SPD-1 C450 peptide
<220> FEATURE:
<221> NAME/KEY: MISC_FEATURE
<222> LOCATION: (1)..(20)
<223> OTHER INFORMATION: Putative surface domain
<220> FEATURE:
<221> NAME/KEY: MISC_FEATURE
<222> LOCATION: (3)..(15)
<223> OTHER INFORMATION: Detected peptide sequence
<220> FEATURE:
<221> NAME/KEY: MISC_FEATURE
<222> LOCATION: (117)..(134)
<223> OTHER INFORMATION: Putative surface domain
<220> FEATURE:
<221> NAME/KEY: MISC_FEATURE
<222> LOCATION: (117)..(127)
<223> OTHER INFORMATION: Detected peptide sequence
<220> FEATURE:
<221> NAME/KEY: MISC_FEATURE
<222> LOCATION: (155)..(174)
<223> OTHER INFORMATION: Putative surface domain
<220> FEATURE:
<221> NAME/KEY: MISC_FEATURE
<222> LOCATION: (156)..(166)
<223> OTHER INFORMATION: Detected peptide sequence
<220> FEATURE:
<221> NAME/KEY: MISC_FEATURE
<222> LOCATION: (288)..(314)
<223> OTHER INFORMATION: Putative surface domain
<220> FEATURE:
<221> NAME/KEY: MISC_FEATURE
<222> LOCATION: (297)..(314)
<223> OTHER INFORMATION: Detected peptide sequence
<220> FEATURE:
<221> NAME/KEY: MISC_FEATURE
<222> LOCATION: (379)..(404)
<223> OTHER INFORMATION: Putative surface domain
<220> FEATURE:
<221> NAME/KEY: MISC_FEATURE
<222> LOCATION: (380)..(394)

<223> OTHER INFORMATION: Detected peptide sequence
<220> FEATURE:
<221> NAME/KEY: MISC_FEATURE
<222> LOCATION: (424)..(442)
<223> OTHER INFORMATION: Putative surface domain
<220> FEATURE:
<221> NAME/KEY: MISC_FEATURE
<222> LOCATION: (424)..(442)
<223> OTHER INFORMATION: Detected peptide sequence

<400> SEQUENCE: 4

```
Asp Lys Ile Leu Leu Leu Leu Asp Lys Val Ile Glu Ser Met Arg Leu
1               5                   10                  15

Tyr Thr Pro Ser Leu Ala Ser Phe Met Ser Ser Arg Gln Lys Tyr Leu
            20                  25                  30

Tyr Met Tyr Glu Tyr Asp Lys Val Ser Met Pro Tyr Ser Lys Val Ser
        35                  40                  45

Gln Val Ser Leu Ala Phe His Asp Pro Leu Tyr Trp Pro Ser Ser Glu
    50                  55                  60

Met Leu Tyr Ala Ile Asn Ser Thr Thr Tyr Glu Asp Val Gln Val Phe
65                  70                  75                  80

His Ser Arg Arg Phe Ser Ser Val Phe Thr Glu Val Leu Ala Val Gly
                85                  90                  95

Leu Leu Ser Asn Ser Thr Lys Asp Leu Leu Glu Ile Tyr Phe Lys Ala
            100                 105                 110

Leu Ser Pro Lys Lys Gln Tyr Pro Tyr Gln Ile Leu Pro Ser Arg Ser
        115                 120                 125

Tyr Ile Phe Lys Glu Gly Ser Asn Tyr Ile Tyr Glu Met Ser Leu Leu
    130                 135                 140

Asn Pro Gln Glu Val Asn Ser Ala Ile Leu Tyr Ser Leu Gln Val Gly
145                 150                 155                 160

Ser Ser Lys Asp Ser Lys Leu Ile Ala Leu Leu Asn Val Leu Phe Ser
                165                 170                 175

Leu Ile Arg Ser Arg Val Phe Asn Gln Leu Arg Thr Glu Glu Gln Leu
            180                 185                 190

Ser Tyr Val Val Arg Val Ser Ser Tyr Thr Ser Thr Ala Leu Met Ser
        195                 200                 205

Phe Phe Phe Val Leu Gln Ser Leu Arg Asp Pro Phe Tyr Leu Glu Gln
    210                 215                 220

Arg Ile Asn Ala Phe Leu Tyr Arg Phe Ala Ala Phe Ile Asp Thr Ile
225                 230                 235                 240

Thr Asp Glu Gln Leu Lys Ser Val Val Asn Thr Leu Leu Pro Leu Phe
                245                 250                 255

Ser Gly Arg Tyr Thr Ser Leu Pro Lys Glu Ser Gly Val Tyr Leu Ala
            260                 265                 270

Ser Ile Val Ser Gly Phe Tyr Asp Phe Asp Ile Arg Lys Lys Ile Tyr
        275                 280                 285

Arg Ser Leu Lys Gly Leu Thr Lys Glu Asp Leu Lys Asp Tyr Phe Tyr
    290                 295                 300

Asn Tyr Phe Tyr Pro Asp Ser Ala Thr Arg Lys Lys Leu Ser Ile His
305                 310                 315                 320

Leu Lys Ser Gln Thr Leu Glu Ser Val Ser Val Arg Asp Phe Ser Pro
                325                 330                 335

Arg Arg Leu Gln Tyr Tyr Phe Lys Cys Asn Gly Leu Asp Ile Ser Leu
            340                 345                 350

Glu Asp Leu Ser Asp Leu Ile Glu Ser Ser His Leu Leu Val Asp Phe
```

```
        355                 360                 365

Glu Lys Ala Leu Lys Lys Phe Phe Thr Asn Lys Tyr Pro His Lys Asp
    370                 375                 380

Val Ser Glu Ile Val Ser Gln Ala Phe Lys Tyr Leu Lys Glu Leu Tyr
385                 390                 395                 400

Thr Lys Leu Lys Lys Asp Ala Ile Lys Asn Tyr Asp Ala Gln His Phe
                405                 410                 415

Thr Asp Leu Thr Thr Phe Lys Asn Ser Leu Lys Leu Ser Pro Val Pro
            420                 425                 430

Leu Pro Val Met Lys Trp Ser Ser Tyr Tyr
        435                 440


<210> SEQ ID NO 5
<211> LENGTH: 1338
<212> TYPE: DNA
<213> ORGANISM: Artificial sequence
<220> FEATURE:
<223> OTHER INFORMATION: Codon optimized nucleotide sequence encoding P.
      murina SPD-1 C450 peptide

<400> SEQUENCE: 5

gataagatct tgctgctctt ggacaaggtc atcgagtcta tgcgtttgta cacccccctcc     60

ctggcctctt tcatgtctag ccgccagaag tacctgtaca tgtacgaata cgacaaggtc    120

agcatgcctt acagcaaggt ctcacaagtt tcgctggctt tccacgaccc cctctactgg    180

ccttcatcgg agatgctcta cgccatcaac tcaacaacct acgaagacgt ccaggttttc    240

cactcccgtc gcttctcctc tgtgttcacc gaggtgctgg ctgtcggcct gctctcgaac    300

tccactaagg acttgctgga aatctacttc aaggccttgt ccccaaagaa gcagtacccg    360

taccaaatcc tgccctctcg cagctacatc ttcaaggagg gatcgaacta catctacgaa    420

atgtccctct tgaaccctca ggaggtcaac tcggctatct tgtactccct gcaagttggt    480

agctcaaagg actccaagct gatcgccctg ctcaacgttc tcttctcgtt gatcaggtcc    540

agagtgttca accagttgag gaccgaggaa caactgagct acgttgtgag agtttcgtcc    600

tacacttcta cagctctgat gtccttcttc ttcgtcctgc agtccctcag ggacccattc    660

tacttggagc aacgtatcaa cgccttcctg taccgcttcg ctgccttcat cgacaccatc    720

actgatgaac agctgaagtc cgtcgttaac actttgctgc ctctcttctc aggtcgttac    780

acatcgttgc caaaggagtc cggtgtgtac ctggcttcca tcgtctctgg cttctacgac    840

ttcgatatcc gtaagaagat ctaccgctca ttgaagggcc tgaccaagga ggacctcaag    900

gattacttct acaactactt ctacccagac tctgccacaa ggaagaagct ctctatccac    960

ttgaagagcc agaccctgga atcagtgtcg gtcagagatt tctcccccag gagactccaa   1020

tactacttca agtgtaacgg tttggacatc tcactcgagg acttgtcgga tctgatcgaa   1080

tctagccacc tcttggtgga cttcgagaag gctctgaaga agttcttcac caacaagtac   1140

cctcacaagg acgtttctga gatcgtgagc caggccttca agtacctcaa ggaattgtac   1200

actaagctca agaaggacgc tatcaagaac tacgatgccc aacacttcac agacctgact   1260

acattcaaga actcgttgaa gctctccccc gtgcccttgc ccgtgatgaa gtggtcgtcc   1320

tactactgat aaaagctt                                                 1338


<210> SEQ ID NO 6
<211> LENGTH: 27
<212> TYPE: PRT
<213> ORGANISM: Artificial sequence
```

<220> FEATURE:
<223> OTHER INFORMATION: N-terminal peptide of P. murina SPD-1
(PNEG_01848)

<400> SEQUENCE: 6

```
Ala Thr Thr Ala Thr Leu Leu Thr Glu Asn Ile Lys Lys Pro Glu Gly
1               5                   10                  15

Asp His Tyr Ser Tyr Arg Leu Ile Gln Leu Ser
            20                  25
```

<210> SEQ ID NO 7
<211> LENGTH: 19
<212> TYPE: PRT
<213> ORGANISM: Artificial sequence
<220> FEATURE:
<223> OTHER INFORMATION: C-terminal peptide of P. murina SPD-1
(PNEG_01848)

<400> SEQUENCE: 7

```
Asn Ser Leu Lys Leu Ser Pro Val Pro Leu Pro Val Met Lys Trp Ser
1               5                   10                  15

Ser Tyr Tyr
```

<210> SEQ ID NO 8
<211> LENGTH: 1035
<212> TYPE: PRT
<213> ORGANISM: Artificial sequence
<220> FEATURE:
<223> OTHER INFORMATION: P. murina SPD-1 mature polypeptide sequemce

<400> SEQUENCE: 8

```
Ala Thr Thr Ala Thr Leu Leu Thr Glu Asn Ile Lys Lys Pro Glu Gly
1               5                   10                  15

Asp His Tyr Ser Tyr Arg Leu Ile Gln Leu Ser Asn Gly Leu Lys Thr
            20                  25                  30

Leu Leu Ile Ser Tyr Pro Asp Ser Leu Ser Ala Gly Ala Ala Leu Asp
        35                  40                  45

Val Lys Val Gly His Phe Ser Asp Pro Asp Asp Ile Pro Gly Val Ala
    50                  55                  60

His Phe Cys Glu His Leu Leu Phe Met Gly Thr Lys Lys Tyr Pro Gly
65                  70                  75                  80

Glu Asp Asp Phe Ser Glu Tyr Leu Leu Thr His Ala Gly Thr Tyr Asn
                85                  90                  95

Ala Tyr Thr Ser Thr Glu Asp Thr Asn Tyr Phe Phe Ser Val Glu Pro
            100                 105                 110

Lys Ser Phe Glu Lys Ala Leu Asp Met Phe Ser Gln Leu Phe Ile Ser
        115                 120                 125

Pro Leu Ile Leu Lys Arg Ser Val Glu Arg Glu Ala His Ala Val Asp
    130                 135                 140

Leu Glu His Lys Lys Asn Leu Gln Asn Asp Ala Trp Arg Leu Phe Gln
145                 150                 155                 160

Leu Glu Lys Ser Ile Ser Asn Pro Lys Ser Pro Tyr Ser Lys Phe Gly
                165                 170                 175

Thr Gly Asp Tyr Val Thr Leu Val Glu Asn Thr Arg Lys Lys Gly Ile
            180                 185                 190

Asp Ile Ala Ser Val Val Ser Lys Phe Phe Ser Thr Tyr Tyr Ser Ser
        195                 200                 205

Asn Leu Met Lys Leu Val Ile Phe Ser Ser Glu Ser Leu Asp Asn Leu
    210                 215                 220
```

```
Glu Lys Leu Ala Val Lys Tyr Phe Thr Asp Ile Pro Asn Lys Asn Leu
225                 230                 235                 240

Glu Val Pro Lys Phe Thr Glu Lys Pro Phe Gly Ala Asp Val Ile Gly
                245                 250                 255

Lys Gln Tyr Trp Tyr Lys Pro Ile Ala Asp Ser Asn Ser Ile Glu Leu
            260                 265                 270

Val Phe Pro Ile Asp Thr Gln Arg Met Phe Tyr Lys Ser Ser Pro Ser
        275                 280                 285

Asp Tyr Leu Arg His Phe Leu Asp His Arg Ser Tyr Gly Ser Val Phe
    290                 295                 300

Tyr Thr Leu Asn Gln Arg Gly Trp Ile Thr Asp Ile Ser Val Tyr Ser
305                 310                 315                 320

Glu Tyr Ile Val Ser Glu Thr Asp Ala Leu Arg Ile Asn Ile Gly Leu
                325                 330                 335

Thr Glu Ile Gly Leu Asp Asn Tyr Glu Asp Ile Leu Gly Leu Val Phe
            340                 345                 350

Gln Phe Leu Arg Met Leu Arg Asp Asn Thr Pro Asn Glu Asp Tyr Phe
        355                 360                 365

Lys Asp Leu Ile Lys Ile Asp Asp Val Ser Phe Arg Phe Lys Asp Gln
    370                 375                 380

Pro Lys Leu Met Ser Tyr Ala Ser His Leu Ala Ser Val Met Gln Leu
385                 390                 395                 400

Pro Tyr Ile Glu Asp Val Asp Leu Leu Arg Ser Ser Tyr Leu Ser Glu
                405                 410                 415

Tyr Asp His Lys Gln Phe Ala Lys Leu Leu Ser Val Leu Arg Asp Asp
            420                 425                 430

Asn Tyr Phe Leu Thr Ile Thr Ser Lys Thr Lys Pro Gly Tyr Trp Asp
        435                 440                 445

Leu Arg Glu Pro Trp Tyr Gly Ser Glu Tyr Lys Val Asp Val Phe Ser
    450                 455                 460

Gln Thr Leu Leu Glu Lys Thr Arg Lys Asp Asp Leu Asn Ile Ser Leu
465                 470                 475                 480

Lys Phe Pro Glu Lys Asn Ile Phe Ile Pro Glu Leu Phe Ile Arg Ala
                485                 490                 495

Asn Val Ser Thr His Lys Lys Thr Lys Pro Thr Leu Met Tyr Asn Asp
            500                 505                 510

Thr Arg Leu Arg Tyr Trp Tyr Lys Glu Asp Asp Thr Phe Ser Ile Pro
        515                 520                 525

Lys Thr Phe Ile Ser Ala Leu Ile Lys Ile Pro Asp Tyr Ser Ser Ser
    530                 535                 540

Pro Phe Glu Thr Ala His Ser Lys Ile Tyr Leu Asp Met Leu Ile Asn
545                 550                 555                 560

His Val Ser Thr Gln His Tyr Asn Ala Ile Val Ala Gly Tyr Ser Leu
                565                 570                 575

Thr Ile Ser Ala Ile Asp Ile Gly Ile Tyr Leu Ser Ile Tyr Gly Phe
            580                 585                 590

Ser Asp Lys Ile Leu Leu Leu Leu Asp Lys Val Ile Glu Ser Met Arg
        595                 600                 605

Leu Tyr Thr Pro Ser Leu Ala Ser Phe Met Ser Ser Arg Gln Lys Tyr
    610                 615                 620

Leu Tyr Met Tyr Glu Tyr Asp Lys Val Ser Met Pro Tyr Ser Lys Val
625                 630                 635                 640
```

```
Ser Gln Val Ser Leu Ala Phe His Asp Pro Leu Tyr Trp Pro Ser Ser
                645                 650                 655

Glu Met Leu Tyr Ala Ile Asn Ser Thr Thr Tyr Glu Asp Val Gln Val
            660                 665                 670

Phe His Ser Arg Arg Phe Ser Ser Val Phe Thr Glu Val Leu Ala Val
        675                 680                 685

Gly Leu Leu Ser Asn Ser Thr Lys Asp Leu Leu Glu Ile Tyr Phe Lys
    690                 695                 700

Ala Leu Ser Pro Lys Lys Gln Tyr Pro Tyr Gln Ile Leu Pro Ser Arg
705                 710                 715                 720

Ser Tyr Ile Phe Lys Glu Gly Ser Asn Tyr Ile Tyr Glu Met Ser Leu
                725                 730                 735

Leu Asn Pro Gln Glu Val Asn Ser Ala Ile Leu Tyr Ser Leu Gln Val
            740                 745                 750

Gly Ser Ser Lys Asp Ser Lys Leu Ile Ala Leu Leu Asn Val Leu Phe
        755                 760                 765

Ser Leu Ile Arg Ser Arg Val Phe Asn Gln Leu Arg Thr Glu Glu Gln
    770                 775                 780

Leu Ser Tyr Val Val Arg Val Ser Ser Tyr Thr Ser Thr Ala Leu Met
785                 790                 795                 800

Ser Phe Phe Phe Val Leu Gln Ser Leu Arg Asp Pro Phe Tyr Leu Glu
                805                 810                 815

Gln Arg Ile Asn Ala Phe Leu Tyr Arg Phe Ala Ala Phe Ile Asp Thr
            820                 825                 830

Ile Thr Asp Glu Gln Leu Lys Ser Val Val Asn Thr Leu Leu Pro Leu
        835                 840                 845

Phe Ser Gly Arg Tyr Thr Ser Leu Pro Lys Glu Ser Gly Val Tyr Leu
    850                 855                 860

Ala Ser Ile Val Ser Gly Phe Tyr Asp Phe Asp Ile Arg Lys Lys Ile
865                 870                 875                 880

Tyr Arg Ser Leu Lys Gly Leu Thr Lys Glu Asp Leu Lys Asp Tyr Phe
                885                 890                 895

Tyr Asn Tyr Phe Tyr Pro Asp Ser Ala Thr Arg Lys Lys Leu Ser Ile
            900                 905                 910

His Leu Lys Ser Gln Thr Leu Glu Ser Val Ser Val Arg Asp Phe Ser
        915                 920                 925

Pro Arg Arg Leu Gln Tyr Tyr Phe Lys Cys Asn Gly Leu Asp Ile Ser
    930                 935                 940

Leu Glu Asp Leu Ser Asp Leu Ile Glu Ser Ser His Leu Leu Val Asp
945                 950                 955                 960

Phe Glu Lys Ala Leu Lys Lys Phe Phe Thr Asn Lys Tyr Pro His Lys
                965                 970                 975

Asp Val Ser Glu Ile Val Ser Gln Ala Phe Lys Tyr Leu Lys Glu Leu
            980                 985                 990

Tyr Thr Lys Leu Lys Lys Asp Ala  Ile Lys Asn Tyr Asp  Ala Gln His
        995                 1000                1005

Phe Thr  Asp Leu Thr Thr Phe  Lys Asn Ser Leu Lys  Leu Ser Pro
    1010                1015                1020

Val Pro  Leu Pro Val Met Lys  Trp Ser Ser Tyr Tyr
    1025                1030                1035
```

<210> SEQ ID NO 9
<211> LENGTH: 3105
<212> TYPE: DNA

```
<213> ORGANISM: Artificial sequence
<220> FEATURE:
<223> OTHER INFORMATION: Codon-optimized nucleotide sequence encoding P.
      murina SPD-1 mature polypeptide

<400> SEQUENCE: 9

gctaccactg ccacactgct caccgagaac atcaagaagc ctgaaggtga ccactactcc     60

tacaggctca tccagttgtc taacggcctg aagaccttgc tgatctcata cccagactca    120

ctctcggctg gcgctgcctt ggatgtgaag gtcggacact tctccgaccc agacgatatc    180

ccaggagtgg ctcacttctg cgagcacctc ttgttcatgg gtactaagaa gtaccccggc    240

gaggacgatt tctctgaata cctgctcacc cacgctggaa cttacaacgc ctacaccagc    300

actgaggata ccaactactt cttctcagtc gagcccaagt cgttcgaaaa ggctctggac    360

atgttctccc agctcttcat ctctcctctg atcctcaaga ggtccgttga gagagaagct    420

cacgccgtgg atttggagca caagaagaac ctgcagaacg acgcctggcg tctgttccaa    480

ctcgaaaagt ccatctctaa ccccaagtcc ccttactcta agttcggtac aggcgattac    540

gttaccctgg tggagaacac tcgcaagaag ggtatcgaca tcgctagcgt ggtctcaaag    600

ttcttctcaa cttactactc ctctaacttg atgaagctgg tcatcttctc ctcagagtcc    660

ctcgataact tggaaaagct ggccgtcaag tacttcactg acatccccaa caagaacctg    720

gaggtgccta agttcacaga aaagccattc ggagctgacg tcatcggcaa gcagtactgg    780

tacaagccga tcgccgatag caactcaatc gagctggtgt tccccatcga cacccaacgc    840

atgttctaca agtcgtcccc ttctgattac ctgaggcact tcctcgacca cagatcgtac    900

ggatccgtct tctacaccct caaccagaga ggttggatca ctgatatctc tgtctacagc    960

gagtacatcg tttccgaaac agacgctctg cgtatcaaca tcggcctgac cgagatcgga   1020

ctcgacaact acgaagatat cttgggcctg gtgttccaat tcctccgtat gttgcgcgac   1080

aacactccta acgaggacta cttcaaggat ctcatcaaga tcgacgatgt ctctttccgt   1140

ttcaaggacc agccaaagtt gatgtcatac gcttcgcacc tcgccagcgt catgcaattg   1200

ccgtacatcg aggacgttga tttgctgcgt tctagctacc tgtctgaata cgaccacaag   1260

cagttcgcta agctcttgag cgtgctccgc gacgataact acttcttgac aatcacctcc   1320

aagaccaagc cgggctactg ggatctgagg gagccctggt acggatctga atacaaggtt   1380

gacgtgttca gccaaacact gctcgagaag accagaaagg acgatttgaa catctctctg   1440

aagttccctg agaagaacat cttcatccca gaactgttca tcagggctaa cgtgagcacc   1500

cacaagaaga ctaagccaac actgatgtac aacgacactc gtctccgcta ctggtacaag   1560

gaggacgata ctttcagcat cccgaagaca ttcatctcag ctctgatcaa gatcccggat   1620

tactcatcgt ccccccttcga aactgcccac tcaaagatct acctggacat gctcatcaac   1680

cacgtgtcca cacagcacta caacgctatc gtcgccggat acagcctgac catctcagct   1740

atcgacatcg gaatctacct cagcatctac ggtttctcag ataagatctt gctgctcttg   1800

gacaaggtca tcgagtctat gcgtttgtac acccccctccc tggcctcttt catgtctagc  1860

cgccagaagt acctgtacat gtacgaatac gacaaggtca gcatgcctta cagcaaggtc   1920

tcacaagttt cgctggcttt ccacgacccc ctctactggc cttcatcgga gatgctctac   1980

gccatcaact caacaaccta cgaagacgtc caggttttcc actcccgtcg cttctcctct   2040

gtgttcaccg aggtgctggc tgtcggcctg ctctcgaact ccactaagga cttgctggaa   2100

atctacttca aggccttgtc cccaaagaag cagtacccgt accaaatcct gccctctcgc   2160
```

-continued

| | |
|---|---|
| agctacatct tcaaggaggg atcgaactac atctacgaaa tgtccctctt gaaccctcag | 2220 |
| gaggtcaact cggctatctt gtactccctg caagttggta gctcaaagga ctccaagctg | 2280 |
| atcgccctgc tcaacgttct cttctcgttg atcaggtcca gagtgttcaa ccagttgagg | 2340 |
| accgaggaac aactgagcta cgttgtgaga gtttcgtcct acacttctac agctctgatg | 2400 |
| tccttcttct tcgtcctgca gtccctcagg gacccattct acttggagca acgtatcaac | 2460 |
| gccttcctgt accgcttcgc tgccttcatc gacaccatca ctgatgaaca gctgaagtcc | 2520 |
| gtcgttaaca ctttgctgcc tctcttctca ggtcgttaca catcgttgcc aaaggagtcc | 2580 |
| ggtgtgtacc tggcttccat cgtctctggc ttctacgact tcgatatccg taagaagatc | 2640 |
| taccgctcat tgaagggcct gaccaaggag gacctcaagg attacttcta caactacttc | 2700 |
| tacccagact ctgccacaag gaagaagctc tctatccact tgaagagcca gaccctggaa | 2760 |
| tcagtgtcgg tcagagattt ctcccccagg agactccaat actacttcaa gtgtaacggt | 2820 |
| ttggacatct cactcgagga cttgtcggat ctgatcgaat ctagccacct cttggtggac | 2880 |
| ttcgagaagg ctctgaagaa gttcttcacc aacaagtacc ctcacaagga cgtttctgag | 2940 |
| atcgtgagcc aggccttcaa gtacctcaag gaattgtaca ctaagctcaa gaaggacgct | 3000 |
| atcaagaact acgatgccca acacttcaca gacctgacta cattcaagaa ctcgttgaag | 3060 |
| ctctcccccg tgcccttgcc cgtgatgaag tggtcgtcct actac | 3105 |

```
<210> SEQ ID NO 10
<211> LENGTH: 18
<212> TYPE: PRT
<213> ORGANISM: Artificial sequence
<220> FEATURE:
<223> OTHER INFORMATION: Peptide PCD4-1

<400> SEQUENCE: 10

Gly Asp His Tyr Ser Tyr Arg Leu Ile Gln Leu Ser Asn Gly Leu Lys
1               5                   10                  15

Thr Leu

<210> SEQ ID NO 11
<211> LENGTH: 12
<212> TYPE: PRT
<213> ORGANISM: Artificial sequence
<220> FEATURE:
<223> OTHER INFORMATION: Peptide PCD4-2

<400> SEQUENCE: 11

Pro Asp Ser Leu Ser Ala Gly Ala Ala Leu Asp Val
1               5                   10

<210> SEQ ID NO 12
<211> LENGTH: 15
<212> TYPE: PRT
<213> ORGANISM: Artificial sequence
<220> FEATURE:
<223> OTHER INFORMATION: Peptide PCD4-3

<400> SEQUENCE: 12

Ser Gln Leu Phe Ile Ser Pro Leu Ile Leu Lys Arg Ser Val Glu
1               5                   10                  15

<210> SEQ ID NO 13
<211> LENGTH: 17
<212> TYPE: PRT
<213> ORGANISM: Artificial sequence
<220> FEATURE:
```

<223> OTHER INFORMATION: Peptide PCD4-4

<400> SEQUENCE: 13

Tyr Ser Ser Asn Leu Met Lys Leu Val Ile Phe Ser Ser Glu Ser Leu
1 5 10 15

Asp

<210> SEQ ID NO 14
<211> LENGTH: 15
<212> TYPE: PRT
<213> ORGANISM: Artificial sequence
<220> FEATURE:
<223> OTHER INFORMATION: Peptide PCD4-5

<400> SEQUENCE: 14

Thr Gln His Tyr Asn Ala Ile Val Ala Gly Tyr Ser Leu Thr Ile
1 5 10 15

<210> SEQ ID NO 15
<211> LENGTH: 15
<212> TYPE: PRT
<213> ORGANISM: Artificial sequence
<220> FEATURE:
<223> OTHER INFORMATION: Peptide PCD4-6

<400> SEQUENCE: 15

Trp Pro Ser Ser Glu Met Leu Tyr Ala Ile Asn Ser Thr Thr Tyr
1 5 10 15

<210> SEQ ID NO 16
<211> LENGTH: 14
<212> TYPE: PRT
<213> ORGANISM: Artificial sequence
<220> FEATURE:
<223> OTHER INFORMATION: Peptide PCD4-7

<400> SEQUENCE: 16

Thr Thr Tyr Glu Asp Val Gln Val Phe His Ser Arg Arg Phe
1 5 10

<210> SEQ ID NO 17
<211> LENGTH: 18
<212> TYPE: PRT
<213> ORGANISM: Artificial sequence
<220> FEATURE:
<223> OTHER INFORMATION: Peptide PCD4-8

<400> SEQUENCE: 17

Ser Ile Val Ser Gly Phe Tyr Asp Phe Asp Ile Arg Lys Lys Ile Tyr
1 5 10 15

Arg Ser

<210> SEQ ID NO 18
<211> LENGTH: 18
<212> TYPE: PRT
<213> ORGANISM: Artificial sequence
<220> FEATURE:
<223> OTHER INFORMATION: Peptide PCD4-9

<400> SEQUENCE: 18

Ile His Leu Lys Ser Gln Thr Leu Glu Ser Val Ser Val Arg Asp Phe
1 5 10 15

Ser Pro

<210> SEQ ID NO 19
<211> LENGTH: 15
<212> TYPE: PRT
<213> ORGANISM: Artificial sequence
<220> FEATURE:
<223> OTHER INFORMATION: Peptide PCD4-10

<400> SEQUENCE: 19

Arg Leu Gln Tyr Tyr Phe Lys Cys Asn Gly Leu Asp Ile Ser Leu
1 5 10 15

<210> SEQ ID NO 20
<211> LENGTH: 15
<212> TYPE: PRT
<213> ORGANISM: Artificial sequence
<220> FEATURE:
<223> OTHER INFORMATION: Peptide PCD4-11

<400> SEQUENCE: 20

Ala Phe Lys Tyr Leu Lys Glu Leu Tyr Thr Lys Leu Lys Lys Asp
1 5 10 15

<210> SEQ ID NO 21
<211> LENGTH: 10
<212> TYPE: PRT
<213> ORGANISM: Artificial sequence
<220> FEATURE:
<223> OTHER INFORMATION: Peptide PCD8-1

<400> SEQUENCE: 21

Thr Thr Ala Thr Leu Leu Thr Glu Asn Ile
1 5 10

<210> SEQ ID NO 22
<211> LENGTH: 10
<212> TYPE: PRT
<213> ORGANISM: Artificial sequence
<220> FEATURE:
<223> OTHER INFORMATION: Peptide PCD8-2

<400> SEQUENCE: 22

Ala Leu Asp Met Phe Ser Gln Leu Phe Ile
1 5 10

<210> SEQ ID NO 23
<211> LENGTH: 9
<212> TYPE: PRT
<213> ORGANISM: Artificial sequence
<220> FEATURE:
<223> OTHER INFORMATION: Peptide PCD8-3

<400> SEQUENCE: 23

Leu Pro Lys Glu Ser Gly Val Tyr Leu
1 5

<210> SEQ ID NO 24
<211> LENGTH: 10
<212> TYPE: PRT
<213> ORGANISM: Artificial sequence
<220> FEATURE:
<223> OTHER INFORMATION: Peptide PCD8-4

<400> SEQUENCE: 24

Tyr Pro His Lys Asp Val Ser Glu Ile Val
1 5 10

<210> SEQ ID NO 25

<211> LENGTH: 10
<212> TYPE: PRT
<213> ORGANISM: Artificial sequence
<220> FEATURE:
<223> OTHER INFORMATION: Peptide PCD8-5

<400> SEQUENCE: 25

Lys Tyr Leu Lys Glu Leu Tyr Thr Lys Leu
1 5 10

<210> SEQ ID NO 26
<211> LENGTH: 22
<212> TYPE: PRT
<213> ORGANISM: Artificial sequence
<220> FEATURE:
<223> OTHER INFORMATION: Peptide PC-S24

<400> SEQUENCE: 26

Ala Thr Thr Ala Thr Leu Leu Thr Glu Asn Ile Lys Lys Pro Glu Gly
1 5 10 15

Asp His Tyr Ser Tyr Arg
20

<210> SEQ ID NO 27
<211> LENGTH: 17
<212> TYPE: PRT
<213> ORGANISM: Artificial sequence
<220> FEATURE:
<223> OTHER INFORMATION: Peptide PC-S25

<400> SEQUENCE: 27

Ala Leu Asp Met Phe Ser Gln Leu Phe Ile Ser Pro Leu Ile Leu Lys
1 5 10 15

Arg

<210> SEQ ID NO 28
<211> LENGTH: 19
<212> TYPE: PRT
<213> ORGANISM: Artificial sequence
<220> FEATURE:
<223> OTHER INFORMATION: Peptide PC-S26

<400> SEQUENCE: 28

Glu Ala His Ala Val Asp Leu Glu His Lys Lys Asn Leu Gln Asn Asp
1 5 10 15

Ala Trp Arg

<210> SEQ ID NO 29
<211> LENGTH: 12
<212> TYPE: PRT
<213> ORGANISM: Artificial sequence
<220> FEATURE:
<223> OTHER INFORMATION: Peptide PC-S27

<400> SEQUENCE: 29

Lys Lys Gly Ile Asp Ile Ala Ser Val Val Ser Lys
1 5 10

<210> SEQ ID NO 30
<211> LENGTH: 18
<212> TYPE: PRT
<213> ORGANISM: Artificial sequence
<220> FEATURE:
<223> OTHER INFORMATION: Peptide PC-S28

<400> SEQUENCE: 30

Leu Val Ile Phe Ser Ser Glu Ser Leu Asp Asn Leu Glu Lys Leu Ala
1 5 10 15

Val Lys

<210> SEQ ID NO 31
<211> LENGTH: 14
<212> TYPE: PRT
<213> ORGANISM: Artificial sequence
<220> FEATURE:
<223> OTHER INFORMATION: Peptide PC-S29

<400> SEQUENCE: 31

Asp Leu Ile Lys Ile Asp Asp Val Ser Phe Arg Phe Lys Asp
1 5 10

<210> SEQ ID NO 32
<211> LENGTH: 12
<212> TYPE: PRT
<213> ORGANISM: Artificial sequence
<220> FEATURE:
<223> OTHER INFORMATION: Peptide PC-S30

<400> SEQUENCE: 32

Tyr Leu Ser Glu Tyr Asp His Lys Gln Phe Ala Lys
1 5 10

<210> SEQ ID NO 33
<211> LENGTH: 12
<212> TYPE: PRT
<213> ORGANISM: Artificial sequence
<220> FEATURE:
<223> OTHER INFORMATION: Peptide PC-S31

<400> SEQUENCE: 33

Trp Tyr Lys Glu Asp Asp Thr Phe Ser Ile Pro Lys
1 5 10

<210> SEQ ID NO 34
<211> LENGTH: 17
<212> TYPE: PRT
<213> ORGANISM: Artificial sequence
<220> FEATURE:
<223> OTHER INFORMATION: Peptide PC-S32

<400> SEQUENCE: 34

Ile Lys Ile Pro Asp Tyr Ser Ser Ser Pro Phe Glu Thr Ala His Ser
1 5 10 15

Lys

<210> SEQ ID NO 35
<211> LENGTH: 13
<212> TYPE: PRT
<213> ORGANISM: Artificial sequence
<220> FEATURE:
<223> OTHER INFORMATION: Peptide PC-S33

<400> SEQUENCE: 35

Ile Leu Leu Leu Leu Asp Lys Val Ile Glu Ser Met Arg
1 5 10

<210> SEQ ID NO 36
<211> LENGTH: 11
<212> TYPE: PRT
<213> ORGANISM: Artificial sequence
<220> FEATURE:

<223> OTHER INFORMATION: Peptide PC-S34

<400> SEQUENCE: 36

Lys Gln Tyr Pro Tyr Gln Ile Leu Pro Ser Arg
1 5 10

<210> SEQ ID NO 37
<211> LENGTH: 11
<212> TYPE: PRT
<213> ORGANISM: Artificial sequence
<220> FEATURE:
<223> OTHER INFORMATION: Peptide PC-S35

<400> SEQUENCE: 37

Ser Leu Gln Val Gly Ser Ser Lys Asp Ser Lys
1 5 10

<210> SEQ ID NO 38
<211> LENGTH: 18
<212> TYPE: PRT
<213> ORGANISM: Artificial sequence
<220> FEATURE:
<223> OTHER INFORMATION: Peptide PC-S36

<400> SEQUENCE: 38

Glu Asp Leu Lys Asp Tyr Phe Tyr Asn Tyr Phe Tyr Pro Asp Ser Ala
1 5 10 15

Thr Arg

<210> SEQ ID NO 39
<211> LENGTH: 15
<212> TYPE: PRT
<213> ORGANISM: Artificial sequence
<220> FEATURE:
<223> OTHER INFORMATION: Peptide PC-S37

<400> SEQUENCE: 39

Tyr Pro His Lys Asp Val Ser Glu Ile Val Ser Gln Ala Phe Lys
1 5 10 15

<210> SEQ ID NO 40
<211> LENGTH: 19
<212> TYPE: PRT
<213> ORGANISM: Artificial sequence
<220> FEATURE:
<223> OTHER INFORMATION: Peptide PC-S38

<400> SEQUENCE: 40

Asn Ser Leu Lys Leu Ser Pro Val Pro Leu Pro Val Met Lys Trp Ser
1 5 10 15

Ser Tyr Tyr

<210> SEQ ID NO 41
<211> LENGTH: 1099
<212> TYPE: PRT
<213> ORGANISM: Pneumocystis murina
<220> FEATURE:
<221> NAME/KEY: MISC_FEATURE
<222> LOCATION: (1)..(1099)
<223> OTHER INFORMATION: P. murina antigen A12 PNEG_02212

<400> SEQUENCE: 41

Met Phe Phe Leu Arg Ile Ile Phe Ile Phe Ile Phe Leu Lys Ile Ser
1 5 10 15

Tyr Ala Glu Asn Thr Asp Lys Leu Ser Asp Phe Glu Lys Lys Tyr Pro

```
            20                  25                  30

Glu Leu Tyr Gln Ala Asn Pro His Ala Leu Lys Leu Glu Ala Leu Lys
        35                  40                  45

Ser Gly Phe Ser Gly Lys Ser Val Lys Lys Gly Leu Gly Val Phe His
    50                  55                  60

Ile Gly Asn Leu Gly His Tyr Arg Asp His Lys Pro Val Ile Leu His
65                  70                  75                  80

Val Ile Met Gly Leu Thr Val Gly Leu Ala Glu Cys Arg Gly Thr Leu
                85                  90                  95

Ala Glu Arg Cys Lys Val Ile Lys Ala Leu Gly Asn Pro Ile Thr Gln
            100                 105                 110

Tyr Cys Asn Lys Pro Tyr Asp Thr Cys Gln Asp Tyr Phe Asp Ala Arg
        115                 120                 125

Asn Tyr Leu Leu Pro Met Lys Asp Gln Leu Lys Asn Pro His Ala His
    130                 135                 140

His Asp Ala Cys Arg Thr Ile Leu Leu Asn Cys Leu Phe Phe Lys His
145                 150                 155                 160

Arg Asn Tyr Ile Thr Ser Asp Cys Val Pro Leu Val Ala Leu Cys Tyr
                165                 170                 175

Leu Arg Val Arg Gln Asn Phe Val Glu Ala Ile Met Thr Glu Ala Leu
            180                 185                 190

Arg Gly Glu Ile Asn Thr Lys Gly Ala Ala Ala Ala Met Lys Lys Val
        195                 200                 205

Cys Glu Lys Ile Gly His Glu Ser Pro Asp Leu Leu His Leu Cys Phe
    210                 215                 220

Lys Thr Thr Val Leu Glu Lys Leu Lys Arg Ser Asn Lys Gln Tyr Ile
225                 230                 235                 240

Glu Asp Val Lys Ser Arg Ile Arg Thr Val Ser Thr Gly Asn Cys Arg
                245                 250                 255

Gln Val Leu Glu Glu Cys Tyr Phe Asn Val Leu Asp Tyr Pro Asp Ile
            260                 265                 270

Tyr Gln Ser Cys Arg Asn Phe Arg Arg Phe Cys Ser Glu Ile Gly Val
        275                 280                 285

Val Tyr Thr Pro Val Asp Ser Thr Phe Asp Leu Phe Gln Lys Pro Leu
    290                 295                 300

Ser Ala Glu Lys Leu Leu Ile Asp Thr Ser Ser Lys Ile Ser Glu Asp
305                 310                 315                 320

Leu Gly Leu Gly Phe Ser Lys Tyr Val Gln Lys Lys Ser Ser Asn Leu
                325                 330                 335

Glu Ile Ala Ala Tyr Leu Val Asn Lys Thr Trp Val Tyr Asp Asn Asp
            340                 345                 350

Cys Arg Asn Lys Leu Lys Glu Leu Cys Leu His Ile Ala Ser Leu Pro
        355                 360                 365

Leu Thr Lys Gln Leu Cys Thr Leu Ala His Asp Arg Asn Ser Lys Leu
    370                 375                 380

Cys Arg Asp Phe Tyr Asn Ser Ile Gly Thr Glu Cys Tyr Ser Leu Tyr
385                 390                 395                 400

Tyr Glu Phe Lys Asn Val Gly Leu Leu Tyr Asn Tyr Thr Tyr Arg Leu
                405                 410                 415

Ser Arg Asp Gln Cys Ser Lys Tyr Val Glu Arg Cys Leu Phe Leu Arg
            420                 425                 430

Glu Gln Tyr Ala Tyr Trp Asn Ser Leu Asp Thr Cys Ala Asn Val Phe
        435                 440                 445
```

```
Ser Ser Cys Tyr Lys Glu Asp Met Asp Phe Ser Ala Lys Leu Asp Leu
    450                 455                 460

Leu Asn Arg Ile Lys Asp Lys Ile Val Val Pro Lys Gly Asn Thr Arg
465                 470                 475                 480

Tyr Phe Val Glu Leu Leu Cys Lys Ser Tyr Ile Val Ala Glu Cys Ser
                485                 490                 495

Ala Ser Asp Leu Met Phe Lys Ser Tyr Ala Leu Met Glu Ala Cys Leu
            500                 505                 510

His Pro Glu Arg Ile Cys Arg Glu Leu Lys Asn His Phe Ser Glu Glu
        515                 520                 525

Ser Arg Lys Leu Glu Asn Lys Leu Arg Ser Ile Leu Lys Pro Thr Tyr
    530                 535                 540

Tyr Glu Cys Lys Asp Leu Gly Gln Lys Cys Asn Ser Gly Phe Tyr Phe
545                 550                 555                 560

Asp Gly Asp Ile Glu Ala Gln Cys Asn His Phe Lys Lys Arg Cys Gln
                565                 570                 575

Asp Lys Gln Glu Arg Leu Lys Leu Ile Asn His Ile Val Asn Ser Ser
            580                 585                 590

Ala Leu Tyr Leu Ala Asn Glu Val Gln Cys Arg Thr Tyr Phe Asp Ser
        595                 600                 605

Phe Cys Gly Ala Asn Val Lys Gln Glu Phe Lys Gln Ile Cys Asn Lys
    610                 615                 620

Gly Ala Asn Gly Ile Cys Pro Asp Met Ile Asp Asp Ser Lys Glu His
625                 630                 635                 640

Cys Ala His Leu Ile Asn His Leu Thr Ser Leu Gly Ile Ser Ser Ser
                645                 650                 655

Ser Ala Ser Leu Pro Leu Asp Tyr Cys Asp Ser Ala Ile Asn Tyr Cys
            660                 665                 670

Asn Ser Leu Ser Lys Phe Cys Thr Glu Ser Lys Arg Gln Cys Asp Ser
        675                 680                 685

Val Ile Ser Phe Cys Thr Ser Glu Ser Lys Lys Thr Asp Glu Tyr Gly
    690                 695                 700

Ser Phe Ile Asp Gln Tyr Pro Ala Ala Ala Ala Asn Ala Thr Lys Cys
705                 710                 715                 720

Lys Val Thr Leu Lys Glu Leu Cys Gln Asp Ser Ser Lys Lys Asp Ser
                725                 730                 735

Tyr Ser Thr Leu Cys Ala Tyr Asn Lys Asp Gly Tyr Thr Glu Ile Cys
            740                 745                 750

Lys Asn Leu Arg Asn Phe Ile Glu Lys Ala Cys Glu Asn Leu Arg Ile
        755                 760                 765

His Leu His Thr Tyr Asp Thr Asn Ser Leu Asn Thr Asn Lys Gly Ser
    770                 775                 780

Ala Gln Asp Arg Cys Thr Tyr Ile Arg Asn Leu Tyr Phe Lys Phe Lys
785                 790                 795                 800

Asn Ile Cys Leu Leu Val Asp Pro Phe Tyr Asp Leu Ser Pro Ile Ile
                805                 810                 815

Thr Gln Glu Cys Lys Thr Asn Ile Ser Glu Pro Ala Leu Pro Asp Lys
            820                 825                 830

Asp Pro Gln Pro Thr Ser Ser Pro Gln Pro Lys Pro Arg Pro Arg Pro
        835                 840                 845

Arg Pro Gln Pro Gln Pro His Pro His Pro Lys Pro Gln Pro Gln Pro
    850                 855                 860
```

```
Thr Pro Glu Pro Gln Pro Gln Pro Ala Pro Glu Pro Arg Pro Gln Pro
865                 870                 875                 880

Thr Ser Lys Pro Arg Pro Gln Pro Thr Ser Lys Pro Arg Pro Gln Pro
                885                 890                 895

Thr Pro Glu Pro Arg Pro Leu Pro Val Pro Gly Pro Gly Pro Leu Pro
            900                 905                 910

Val Pro Gly Pro Arg Pro Gln Pro Gln Pro Gln Pro Gln Pro Gln Pro
        915                 920                 925

Gln Pro Gln Pro Gln Pro Gln Pro Gln Pro Gln Pro Gln Pro Gln Pro
    930                 935                 940

Gln Pro Gln Pro Gln Pro Gln Pro Lys Pro Gln Pro Pro Ser Gln Ser
945                 950                 955                 960

Thr Ser Glu Ser Ala Ser Gln Ser Lys Pro Lys Pro Thr Thr Gln Thr
                965                 970                 975

Lys Pro Ser Pro Arg Pro His Pro Arg Pro Val Pro Lys Pro Ser Ser
            980                 985                 990

Ile Asp Thr Gly Pro Ser Lys Ser  Asp Ser Ser Phe Ile  Phe Thr Val
        995                 1000                1005

Thr Lys  Thr Ile Thr Lys Ile  Ser Glu Thr Glu Lys  Pro Ser Thr
    1010                1015                1020

Lys Pro  Ser Val Lys Pro Thr  Ser Thr Lys Thr Thr  Ser Lys Pro
    1025                1030                1035

Ser Thr  Lys Pro Ser Thr Lys  Pro Ser Val Lys Pro  Ala Ser Thr
    1040                1045                1050

Lys Thr  Thr Ser Glu Ser Glu  Lys Pro Thr Leu Glu  Glu Val Pro
    1055                1060                1065

Glu Thr  Lys Gly Asn Gly Val  Arg Val Ile Gly Phe  Glu Gly Leu
    1070                1075                1080

Gln Leu  Leu Ser Met Ile Val  Ala Ile Ile Ile Gly  Ile Trp Ile
    1085                1090                1095

Met


<210> SEQ ID NO 42
<211> LENGTH: 645
<212> TYPE: PRT
<213> ORGANISM: Pneumocystis murina
<220> FEATURE:
<221> NAME/KEY: MISC_FEATURE
<222> LOCATION: (1)..(645)
<223> OTHER INFORMATION: P. murina HSP60 PNEG_02587

<400> SEQUENCE: 42

Met Ala Phe Glu Lys Ala Ile Gly Ile Asp Leu Gly Thr Thr Phe Ser
1               5                   10                  15

Cys Val Gly Val Trp Gln Asn Asp Arg Val Glu Ile Ile Ala Asn Asp
            20                  25                  30

Gln Gly Asn Arg Thr Thr Pro Ser Tyr Val Ala Phe Ser Asp Thr Glu
        35                  40                  45

Arg Leu Ile Gly Asp Ser Ala Lys Asn Gln Val Ala Met Asn Pro Ser
    50                  55                  60

Asn Thr Val Phe Asp Ala Lys Arg Leu Ile Gly Arg Lys Phe Gly Glu
65                  70                  75                  80

Pro Glu Val Gln Ala Asp Met Lys His Trp Pro Phe Lys Val Ile Asp
                85                  90                  95

Arg Gly Gly Lys Pro Tyr Ile Gln Val Glu Phe Lys Gly Glu Ser Lys
            100                 105                 110
```

-continued

```
Thr Phe Thr Pro Glu Glu Ile Ser Ser Met Val Leu Ile Lys Met Lys
        115                 120                 125

Glu Val Ala Glu Ser Tyr Leu Gly Lys Thr Ile Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Leu Ile Ala Gly Leu Asn Val Leu Arg Ile Ile Asn Glu Pro
                165                 170                 175

Thr Ala Ala Ala Ile Ala Tyr Gly Leu Asp Lys Lys Thr Glu Gly Glu
            180                 185                 190

Arg Asn Val Leu Ile Phe Asp Leu Gly Gly Gly Thr Phe Asp Val Ser
        195                 200                 205

Leu Leu Thr Ile Glu Glu Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Gln Glu Phe Lys Arg Lys His Lys Lys Asp Ile Ser Gly Asn
                245                 250                 255

Pro Arg Ala Leu Arg Arg Leu Arg Thr Ala Cys Glu Arg Ala Lys Arg
            260                 265                 270

Ser Leu Ser Ser Ser Thr Gln Thr Ser Ile Glu Ile Asp Ser Leu Tyr
        275                 280                 285

Glu Gly Ile Asp Leu Tyr Thr Ser Ile Thr Arg Ala Arg Phe Glu Glu
    290                 295                 300

Leu Cys Gln Asp Leu Phe Arg Gly Thr Met Glu Pro Val Glu Lys Val
305                 310                 315                 320

Leu Arg Asp Ala Lys Ile Asp Lys Ser Ser Val His Glu Ile Val Leu
                325                 330                 335

Val Gly Gly Ser Thr Arg Ile Pro Arg Ile Gln Lys Leu Val Ser Asp
            340                 345                 350

Phe Phe Asn Gly Lys Glu Pro Asn Lys Ser Ile Asn Pro Asp Glu Ala
        355                 360                 365

Val Ala Tyr Gly Ala Ala Val Gln Ala Ala Ile Leu Ser Gly Asp Thr
    370                 375                 380

Ser Glu Lys Thr Gln Asp Leu Leu Leu Leu Asp Val Ala Pro Leu Ser
385                 390                 395                 400

Met Gly Ile Glu Thr Ala Gly Gly Val Met Thr Pro Leu Ile Lys Arg
                405                 410                 415

Asn Thr Thr Val Pro Thr Lys Lys Ser Glu Val Phe Ser Thr Tyr Ser
            420                 425                 430

Asp Asn Gln Pro Gly Val Leu Ile Gln Val Phe Glu Gly Glu Arg Pro
        435                 440                 445

Arg Thr Arg Asp Cys His Leu Leu Gly Cys Phe Asp Leu Thr Gly Ile
    450                 455                 460

Pro Pro Ala Pro Arg Gly Val Pro Gln Ile Glu Val Thr Phe Asp Val
465                 470                 475                 480

Asp Ala Asn Ser Ile Leu Asn Val Ser Ala Val Glu Lys Gly Thr Gly
                485                 490                 495

Lys Thr Asn Lys Ile Glu Ile Lys Asn Glu Lys Gly Arg Leu Thr Lys
            500                 505                 510

Glu Glu Ile Glu Arg Met Ile Gln Glu Ala Glu Lys Tyr Lys Ala Glu
        515                 520                 525
```

Asp Glu Glu Glu Ala Gln Arg Val Ser Ala Lys Asn Gly Leu Glu Ser
530 535 540

Tyr Ala Tyr Ser Leu Lys Asn Thr Leu Ser Asp Ser Lys Val Gly Asp
545 550 555 560

Lys Ile Gly Glu Ala Glu Lys Thr Lys Leu Glu Lys Ala Val Ala Asp
565 570 575

Val Thr Ser Trp Leu Glu Thr Asn Gln Thr Ala Thr Lys Asp Glu Tyr
580 585 590

Ser Ser Arg Gln Lys Glu Leu Glu Ala Ile Ala Gly Pro Ile Met Met
595 600 605

Lys Phe Tyr Gln Ser Gly Asp Gly Val Pro Gly Met Gly Gly Ala Tyr
610 615 620

Gly Gln Pro Gly Gly Phe Pro Gly Ala Thr Asp Asp His Gly Pro Ser
625 630 635 640

Val Glu Glu Val Asp
645

<210> SEQ ID NO 43
<211> LENGTH: 1075
<212> TYPE: PRT
<213> ORGANISM: Pneumocystis murina
<220> FEATURE:
<221> NAME/KEY: MISC_FEATURE
<222> LOCATION: (1)..(1075)
<223> OTHER INFORMATION: P. murina major surface glycoprotein-like PNEG_00002

<400> SEQUENCE: 43

Met Lys Ser Ile Ser Phe Thr Phe Phe Ile Tyr Leu Ser Cys Ile Leu
1 5 10 15

Val Ala Ala Leu Glu Asn Ala Ile Ser Tyr Ile Asn Glu Gln Asp Phe
20 25 30

Gln Val Ile Glu Leu Phe Glu Asn Glu Lys Leu Leu Leu Leu Glu Lys
35 40 45

Ile Lys Gly Ser Lys Gly Thr Trp Asn Arg Arg Ile Asn Lys Asp Ser
50 55 60

Asn Met Asn Tyr Phe Glu Thr His Pro Gly Val Asp Tyr Phe Arg Lys
65 70 75 80

Asp Asp Tyr Glu Asn Phe Phe Pro Glu Gly Tyr Pro Gln Asp Asn Gln
85 90 95

Trp Val Glu Glu Ile Ser Gln Lys Arg Ala Val Met Ala Gln Leu Val
100 105 110

Lys Arg Gln Ala Ala Gly Gln Ala Ala Gly Asn Asp Glu Ile Lys Glu
115 120 125

Glu Gln Val Leu Gly Leu Ile Val Lys Lys Glu Tyr Glu Asp Asp Ala
130 135 140

Asn Cys Lys Lys Lys Leu Glu Glu Tyr Cys Ala Glu Leu Lys Lys Ile
145 150 155 160

Asp Gly Lys Leu Glu Asn Val Asp Ala Lys Val Lys Gly Leu Cys Glu
165 170 175

Asp Gly Lys Gln Gly Glu Lys Cys Lys Ser Leu Lys Glu Arg Val Lys
180 185 190

Lys Glu Leu Asp Ser Phe Lys Thr Glu Val Glu Glu Ala Leu Asn Asn
195 200 205

Leu Thr Asp Gly Lys Cys Arg Lys Cys Glu Glu Lys Cys Val Leu Leu
210 215 220

-continued

```
Glu Glu Ala Asp Pro Ser Asn Leu Ile Glu Lys Cys Val Arg Leu Arg
225                 230                 235                 240

Asp Arg Cys Tyr Gly Arg Arg His Gln Glu Val Thr Lys Glu Ile Phe
                245                 250                 255

Phe Arg Ala Leu Glu Gly Lys Val Asp Asp Thr Asn Glu Cys Lys Arg
            260                 265                 270

Lys Met Lys Gly Ile Cys Gln Arg Leu Ser Gly Tyr Asn Asp Lys Leu
        275                 280                 285

Met Phe Leu Cys Leu Asn Ser Asp Glu Arg Cys Glu Gln Leu Lys Lys
    290                 295                 300

Ser Tyr Gly Asp Ile Cys Lys Pro Leu Gly Arg Glu Leu Glu Asp Asn
305                 310                 315                 320

Glu Leu Val Glu Lys Cys Gln Glu Tyr Leu Glu Lys Cys Tyr Phe Tyr
                325                 330                 335

Gly Ser Ser Cys Lys Asp Thr Lys Cys Asp Lys Val Lys Asn Lys Cys
            340                 345                 350

Lys Gly Lys Gly Ile Glu Tyr Glu Gly Pro Lys Leu Asp Phe Ser Pro
        355                 360                 365

Val Glu Glu Lys Pro Gly Phe Leu Gln Lys Ile Glu Ile Glu Asn Leu
    370                 375                 380

Tyr Lys Arg Leu Glu Ala Lys Gly Ile Ile Asp Gly Glu Ser Lys Asp
385                 390                 395                 400

Lys Thr Leu Gln Asp Leu Ile Leu Leu Leu Ile Lys Gly Arg Asn Glu
                405                 410                 415

Asn Thr Pro Lys Glu Lys Cys Lys Gly Ala Leu Lys Gly Cys Glu Ser
            420                 425                 430

Phe Lys His Leu Asp Tyr Glu Leu Glu Glu Leu Cys Gly Asp Lys Asn
        435                 440                 445

Lys Asn Asn Lys Cys Lys Glu Leu Val Asn Val Asp Val Arg Cys Met
    450                 455                 460

Asn Phe Lys Leu Glu Leu Tyr Leu Lys Gly Leu Ser Thr Glu Phe Glu
465                 470                 475                 480

Lys Asn Lys Glu Ser Asp Tyr Phe Ser Trp Gly Gln Val Ser Lys Leu
                485                 490                 495

Val Ser Arg Lys Asp Cys Gly Lys Phe Glu Ser Glu Cys Phe His Leu
            500                 505                 510

Glu Gly Val Cys Thr Asn Gly Ile Gly Lys Ala Cys Glu Asn Val Arg
        515                 520                 525

Val Ala Cys Tyr Lys Lys Gly Gln Asp Arg Met Leu Asn Arg Tyr Phe
    530                 535                 540

Gln Glu Gly Leu Lys Gly Leu Ile Gly Asn Phe Gly Phe Ile Thr Ser
545                 550                 555                 560

Asn Leu Glu Lys Cys Gln Lys Ser Val Val Gly Asn Tyr Arg Lys Leu
                565                 570                 575

Lys Glu Asp Lys Arg Tyr Phe Ala Lys Cys His Gln Pro Asn Glu Leu
            580                 585                 590

Cys Leu Glu Leu Leu Asp Asp Ile Ser Ala Gln Ser Glu Glu Leu Glu
        595                 600                 605

Val Val Leu Asn Ser Arg Arg Asp Phe Pro Ser Lys Glu Asp Cys Val
    610                 615                 620

Glu Leu Lys Lys Lys Cys Asp Asp Leu Lys Ser Tyr Ser Tyr Leu Asn
625                 630                 635                 640

His Lys Lys Cys Asp Thr Leu Asn Arg Arg Cys Glu Tyr Leu Lys Val
```

```
                645                 650                 655

Thr Glu Glu Leu Arg Lys Arg Leu Leu Lys Arg Gly Asp Asp Ala Leu
            660                 665                 670

Arg Thr Gln Gly Asn Cys Thr Ala Val Leu Lys Lys Glu Cys Glu Glu
        675                 680                 685

Leu Ser Arg Arg Gly Lys Glu Asp Phe Ser Val Ser Cys Ala Leu Arg
    690                 695                 700

Glu Glu Thr Cys Ser Phe Met Val Lys Gln Thr Gly Asn Glu Cys Leu
705                 710                 715                 720

Phe Leu Lys Asn Asn Met Asp Asn Glu Lys Ile Leu Ser Lys Ile Glu
                725                 730                 735

Lys Glu Lys Ser Asn Glu Arg Leu Val Glu Lys Ile Cys Thr Leu Phe
            740                 745                 750

Asp Gln Tyr Cys His Gln Tyr Met Glu Asn Cys Pro Asn Arg Leu Lys
        755                 760                 765

Lys Gly Asp Thr Gly Asn Glu Lys Gly Val Cys Leu Gln Val Lys Glu
    770                 775                 780

Lys Cys Lys Pro Phe Leu Glu Lys Leu Lys Leu Glu Asp Glu Leu Thr
785                 790                 795                 800

His Glu Leu Lys Gly Asn Leu Gly Lys Asp Asp Glu Cys Arg Lys Ala
                805                 810                 815

Leu Gly Asn Tyr Cys Thr Lys Val Glu Lys Ala Arg Asn Gln Thr Leu
            820                 825                 830

Asn Thr Leu Cys Lys Asn Thr Lys Lys Glu Glu Leu Cys Lys Lys Leu
        835                 840                 845

Val Glu Lys Val Lys Gly Lys Cys Pro Thr Leu Lys Asn Glu Leu Asn
    850                 855                 860

Lys Glu Lys Asp Glu Leu Lys Lys Lys Lys Asp Glu Tyr Glu Lys Ala
865                 870                 875                 880

Lys Gln Glu Ala Glu Lys Phe Ala Lys Glu Ala Lys Leu Pro Leu Arg
                885                 890                 895

Pro Glu Gln Ala Asn Val Arg Leu Val Arg Lys Thr Phe Val Asn Gly
            900                 905                 910

Gly Val Ser Glu Ala Glu Lys Lys Ala Phe Asp Arg Met Ala Arg Ala
        915                 920                 925

Leu Glu Leu Tyr Leu Glu Leu Lys Glu Lys Cys Lys Ala Leu Lys Val
    930                 935                 940

Asp Cys Gly Phe Arg Lys Asp Cys Pro Glu Gly Glu Pro Ile Cys Lys
945                 950                 955                 960

Glu Ile Asp Lys Leu Cys Glu Gly Ile Gln Ala Leu Lys Val Thr Pro
                965                 970                 975

Gln His Thr Val Thr Leu Thr Thr Thr Lys Leu Ile Asn Gly Gly Asn
            980                 985                 990

Val Ile Glu Gln Cys Thr Phe Ser  Gln Thr Thr Gly Met  Leu Thr Ser
        995                 1000                 1005

Thr Phe  Thr Leu Thr Ser Thr  Val Thr Leu Thr Ser  Thr Gln Lys
    1010                 1015                 1020

Cys Lys  Pro Met Arg Cys Thr  Thr Asp Ser Asn Lys  Glu Thr Glu
    1025                 1030                 1035

Thr Gln  Lys Glu Glu Glu Glu  Glu Glu Val Lys Pro  Asn Glu Gly
    1040                 1045                 1050

Met Lys  Ile Ile Val Pro Glu  Met Ile Lys Ile Met  Leu Leu Gly
    1055                 1060                 1065
```

Val Ile Val Met Gly Met Leu
1070 1075

<210> SEQ ID NO 44
<211> LENGTH: 299
<212> TYPE: PRT
<213> ORGANISM: Pneumocystis murina
<220> FEATURE:
<221> NAME/KEY: MISC_FEATURE
<222> LOCATION: (1)..(299)
<223> OTHER INFORMATION: P. murina hypothetical protein PNEG_00502

<400> SEQUENCE: 44

Met Gly Phe Leu Phe Val Thr Phe Leu Phe Ala Ile Leu Thr Leu Ile
1 5 10 15

Asn Ala Tyr Lys Val Leu Leu Pro Lys Pro Gly Asp Lys Trp Glu Pro
20 25 30

Gly Leu His Gln Val Thr Trp Glu Ala Val Asp Asp Thr Ser Thr Val
35 40 45

Asn Val Tyr Leu His Arg Asn Asn Asp Asn Pro Pro Phe Tyr Leu Leu
50 55 60

Leu Ala Ala Lys Val Pro Leu Lys Asp Gly Lys Ala Asp Val Pro Ile
65 70 75 80

Pro Tyr Asn Val Ile Pro Gly Ser Glu Tyr Thr Ile Leu Leu Thr Ser
85 90 95

Leu Asn Pro Tyr Asp Val Tyr Thr Ser Ser Gly Gly Phe Glu Ile Thr
100 105 110

Glu Ala Lys Asp Gly Leu Lys Gly Val Cys Val Asp Tyr Leu Lys Asp
115 120 125

Asp Gly Ser Ser Thr Ile Gly Pro Ile Pro Gly Asp Thr Arg Pro Val
130 135 140

Thr Thr Ser Leu Leu Pro Pro Ser Pro Thr Pro Pro Ser Pro Ala Pro
145 150 155 160

Pro Ala Pro Thr Pro Ala Pro Pro Ala Pro Thr Pro Pro Ser Pro Glu
165 170 175

Pro Pro Ala Pro Ala Pro Pro Glu Gly Glu Val Glu Asn Cys Asp Glu
180 185 190

Cys Asp Glu Cys Glu Glu Cys Gly Glu Cys Glu Pro Gly Glu Gly Cys
195 200 205

Asp Cys Asp Ala Asp Asp His Gly Asp Asp Asp Tyr Asp Lys Asp Glu
210 215 220

Asp His Gly His Ser His Asp Asp Asp Asp Asp Asp Asp Asp Asp His
225 230 235 240

Glu Asn Asp His Asp Asp Asp Asp Asp Asp Asp Asp His Gly His Ser
245 250 255

His Asp Asp Asp Asp Asp Gly His Asp His Gly Glu Asp Lys Asn Lys
260 265 270

Leu Ala Asn Ile Gly Ser Thr Asn Ile Val Thr Arg Phe Trp Leu Thr
275 280 285

Met Met Ala Thr Ile Ser Thr Ile Leu Phe Leu
290 295

<210> SEQ ID NO 45
<211> LENGTH: 980
<212> TYPE: DNA
<213> ORGANISM: Artificial sequence
<220> FEATURE:

<223> OTHER INFORMATION: Codon-optimized nucleotide sequence

<400> SEQUENCE: 45

```
gtcgacatgt actccatgca gctcgcttct tgcgttacct tgactctggt gctgctcgtc     60

aacagcatgg ggttcctctt cgtgaccttc ctcttcgcta ttctgactct gattaatgcc    120

tataaagtgc tcctgcctaa gcctggggat aaatgggaac caggcctgca ccaggtgaca    180

tgggaggctg tggacgatac tagtaccgtg aacgtctacc tgcataggaa caatgacaat    240

ccccctttct atctgctcct ggccgctaag gtgcccctga aggacggcaa agcagatgtg    300

cctatcccat acaacgtcat tcccggatct gagtatacca tcctcctgac aagtctgaat    360

ccttacgacg tctataccag ctccggcgga tttgaaatta cagaggccaa ggacggcctc    420

aaaggagtgt gtgtcgatta cctgaaagac gatggatcta gtactatcgg gcccattcct    480

ggtgacacca gacctgtgac cacatcactc ctgccaccca gccctactcc tccatcccca    540

gctccacctg caccaacacc agcaccaccc gctcccactc ctccatctcc tgaaccacct    600

gcaccagcac caccagaggg agaagtggag aactgcgacg aatgtgatga gtgcgaggaa    660

tgtggtgaat gcgagccagg ggagggttgc gattgtgacg ctgacgatca cggggacgat    720

gactatgata aggacgaaga tcacggtcat tcccacgatg atgacgacga tgacgatgac    780

gatcacgaga acgaccatga tgatgatgat gacgatgacg atcatggaca ctctcatgac    840

gatgacgatg acggccacga ccatggagag gataagaaca aactcgcaaa tatcgggtca    900

actaatattg tgacccggtt ctggctgacc atgatggcca caatcagcac tattctcttt    960

ctgtgaggat ccgcggccgc                                                980
```

<210> SEQ ID NO 46
<211> LENGTH: 1092
<212> TYPE: PRT
<213> ORGANISM: Pneumocystis murina
<220> FEATURE:
<221> NAME/KEY: MISC_FEATURE
<222> LOCATION: (1)..(1092)
<223> OTHER INFORMATION: P. murina major surface glycoprotein-related
      PNEG_00831

<400> SEQUENCE: 46

```
Met Ile Asn Lys Ile Ile Leu Ile Ala Ile Leu Asn Leu Ile Ala Leu
1               5                   10                  15

Thr Tyr Gly Asn Gln Asn Val Asp Leu Ser Ile Arg Ser Ser Gln Lys
            20                  25                  30

Asn Ala Val Asn Pro Leu Phe Lys Asp Phe Ile Val Lys Glu Asp Ile
        35                  40                  45

Tyr Ala Phe Ile Leu Lys Glu Asp Tyr Asn Asp Glu Asn Lys Cys Lys
    50                  55                  60

Ala Lys Leu Glu Glu Tyr Cys Glu Glu Leu Lys Asp Ile Asp Pro Glu
65                  70                  75                  80

Leu Asn Lys Val Asp Thr Asn Ile Lys Glu Ile Cys Asn Asn Asn Asn
                85                  90                  95

Lys Gly Gln Lys Cys Lys Asp Leu Lys Pro Asn Ile Glu Lys Asn Leu
            100                 105                 110

Asn Gln Val Ser Asn Asp Leu Ser Thr Lys Ile Pro Gly Ser Ile Asp
        115                 120                 125

Tyr Met Asp Val Asp Lys Ala Phe Leu Lys Cys Leu Phe Leu His Asp
    130                 135                 140

Leu Thr Arg Asn Ile Leu Ala Tyr Cys Asn Leu Leu Glu Tyr Tyr Tyr
```

-continued

```
145                 150                 155                 160

Gln Lys Arg Glu His Leu Arg Leu Met Tyr Gly Val Ile Leu Arg Ala
                165                 170                 175

Val Gly Asp Ser Ile Ala Asn Tyr Asp Asp Phe Lys Glu Lys Met Lys
            180                 185                 190

Glu Ile Cys Pro Ile Leu Val Gln Gln Gly Ile Asn Phe Ile Ser Glu
        195                 200                 205

Cys Phe Glu Ile Glu Glu Ser Phe Arg Glu Leu Asn Lys Tyr Ile Asn
    210                 215                 220

Tyr Ser Cys Asn Ser Leu Asn Val Asn Leu Asn Asp Asn Lys Leu Gln
225                 230                 235                 240

Glu Gln Cys Tyr Glu Lys Leu Lys Ser Cys Tyr Phe Leu Lys Asn Lys
                245                 250                 255

Cys Glu Lys Lys Cys Asp Glu Leu Lys Val Leu Cys Glu Lys Lys Asn
            260                 265                 270

Ile Thr Tyr Lys Leu Pro Gly Lys Asp Tyr Asn Pro Ile Lys Pro Glu
        275                 280                 285

Thr Thr Leu Leu Lys Ile Glu Leu Glu Asp Phe Tyr Lys Lys Ile Lys
    290                 295                 300

Asp Lys Lys Ile Tyr Ile Glu Asn Leu Glu Thr Thr Ser Asp Asp Ile
305                 310                 315                 320

Ile Leu Tyr Leu Ser Asn Ala Tyr Thr Gly Phe Ser Glu Asn Ile Cys
                325                 330                 335

Lys Asn Lys Leu Asn Lys Asn Cys Asp Phe Phe Lys Phe Leu Ser Pro
            340                 345                 350

Glu Phe Lys Glu Leu Cys Gln Asp Asn Ile Lys Lys Arg Cys Lys Asp
        355                 360                 365

Ala Ser Lys Ile Ile Asp Arg Cys Arg Lys Leu Lys Met Thr Leu Tyr
    370                 375                 380

Leu Ala Gly Phe Ser Ser His Phe Glu Asp Asn Val Ile Gly Lys Glu
385                 390                 395                 400

Ile Ser Arg Asp Arg Leu Ser Thr Ser Phe Asn Ser Arg Glu Phe Ser
                405                 410                 415

Asn Phe Asn Thr Asn Cys Phe Phe Ile Arg Lys Ser Cys Val Asn Asn
            420                 425                 430

Phe Phe Glu Gly Cys Arg Ala Ala Tyr Tyr Ala Asn Asn Lys Lys Leu
        435                 440                 445

Gln Glu Arg Ser Phe Ile Lys Leu Ile Glu Ser Lys Leu Ile Glu Glu
    450                 455                 460

Gln Tyr Asn Leu Lys Ser Lys Asp Glu Lys Leu Lys Ile Cys Gln Lys
465                 470                 475                 480

Thr Ile Ile Glu Lys Cys Val Ala Leu Ala Asn Ser Asp Ile Arg Asn
                485                 490                 495

Phe Leu Ile Cys Leu Arg Pro Lys Glu Ile Cys Leu Arg Leu Glu Glu
            500                 505                 510

Ile Ile Phe Thr Leu Ser Lys Asp Leu Glu Gln Ala Leu Asp Gln Ala
        515                 520                 525

Arg Asp Phe Pro Lys Glu Glu Asp Cys Val Glu Leu Lys Lys Glu Cys
    530                 535                 540

Glu Gly Ile Leu Lys Asp Leu Gly Ser Asn Asn Val Lys Cys Val Thr
545                 550                 555                 560

Leu Lys Lys Arg Cys Lys Tyr Leu Glu Val Thr Lys Glu Leu Lys Tyr
                565                 570                 575
```

-continued

```
Asp Phe Leu Lys Asp Lys Ser Asp Ser Leu Ala Asn Ile Gln Asn Cys
            580                 585                 590

Met Lys Ala Leu Lys Glu Lys Cys Asp Arg Leu Phe Lys Arg Gly Thr
        595                 600                 605

Asn Ala Phe Gly Val Ser Cys Ala Leu Pro Glu Glu Thr Cys Lys Phe
    610                 615                 620

Met Val Ser Glu Val Glu Asn His Cys Asn Ala Phe Lys Asn Asn Ile
625                 630                 635                 640

Glu Lys His Asp Ile Val Asn Lys Ser Lys Asn Gly Asn Glu Thr Leu
                645                 650                 655

Val Glu Glu Ile Cys Ile Leu Trp Asp Pro Tyr Cys Asp Glu Leu Met
            660                 665                 670

Glu Asn Cys Pro Asp Lys Leu Lys Lys Gly Asp Asn Gly Asn Glu Lys
        675                 680                 685

Gly Val Cys Leu Gln Leu Lys Glu Asn Cys Arg Pro Phe Phe Glu Lys
    690                 695                 700

Leu Lys Leu Glu Asp Glu Leu Thr His Glu Leu Lys Gly Ser Leu Ser
705                 710                 715                 720

Asn Glu Thr Glu Cys Lys Lys Ala Leu Gly Lys His Cys Ser Glu Gln
                725                 730                 735

Lys Asn Ser Gly Asn Gln Lys Phe Asn Ser Phe Cys Asn Thr Asp Lys
            740                 745                 750

Asp Lys Asp Val Glu Glu Lys Val Cys Lys Lys Leu Val Glu Lys Val
        755                 760                 765

Lys Glu Lys Cys Pro Thr Leu Glu Ser Glu Leu Ser Lys Glu Lys Asp
    770                 775                 780

Glu Leu Lys Lys Lys Lys Asp Glu Tyr Glu Lys Val Lys Gln Glu Ser
785                 790                 795                 800

Glu Lys Phe Ser Glu Glu Val Lys Leu Leu Leu Ser Arg Leu Gly Lys
                805                 810                 815

Asp Gly Gln Asp Ala Gly Ser Lys Val Gln Asn Thr Ser Ala Ala Glu
            820                 825                 830

Pro Ala Ala Pro Pro Gly Gly Ala Pro Ala Pro Ala Val Pro Gly Gly
        835                 840                 845

Ser Thr Pro Ser Gly Gly Ala Asn Thr Asn Asn Val Ile Leu Val Arg
    850                 855                 860

Arg Thr Phe Val Ser Gly Glu Val Ser Glu Ala Glu Lys Lys Ala Phe
865                 870                 875                 880

Val Ala Thr Ala Arg Ala Leu Glu Leu Tyr Leu Glu Leu Lys Glu Lys
                885                 890                 895

Cys Lys Gly Leu Gln Gly Asp Cys Gly Phe Arg Lys Asp Cys Pro Lys
            900                 905                 910

Cys Asp Ala Val Cys Thr Glu Ile Asp Lys Leu Cys Glu Gly Ile Glu
        915                 920                 925

Gly Leu Lys Val Thr Pro Tyr Tyr Thr Val Thr Ser Thr Ala Thr Gln
    930                 935                 940

Thr Thr Thr Thr Thr Ala Thr Thr Thr Thr Ile Thr Thr Thr Thr Thr
945                 950                 955                 960

Thr Thr Thr Thr Thr Thr Thr Ala Thr Thr Thr Glu Ser Val Asp Gly
                965                 970                 975

Gly Lys Val Thr Asp Glu Cys Thr Leu Val Gln Thr Thr Asp Thr Trp
            980                 985                 990
```

```
Val Thr Ser Thr Ser Leu His Thr  Ser Thr Met Thr Ser  Thr Ser Thr
        995                 1000                 1005

Leu Thr  Ser Thr Val Thr Leu  Thr Ser Met Arg Lys  Cys Lys Pro
    1010                 1015                 1020

Thr Arg  Cys Thr Ser Asp Ser  Asn Lys Glu Thr Glu  Thr Gln Lys
    1025                 1030                 1035

Glu Glu  Glu Lys Glu Glu Glu  Val Lys Pro Asn Glu  Gly Met Lys
    1040                 1045                 1050

Met Arg  Val Pro Glu Ile Val  Lys Ile Ile Leu Leu  Gly Val Met
    1055                 1060                 1065

Ser Tyr  Ala Thr Gln Gly Gln  Ala Met Gly Arg Gly  Ser Arg Pro
    1070                 1075                 1080

Glu Arg  Gly Gly Asp Gly Thr  Ala Gly
    1085                 1090


<210> SEQ ID NO 47
<211> LENGTH: 1066
<212> TYPE: PRT
<213> ORGANISM: Pneumocystis murina
<220> FEATURE:
<221> NAME/KEY: MISC_FEATURE
<222> LOCATION: (1)..(1066)
<223> OTHER INFORMATION: P. murina hypothetical protein PNEG_01105

<400> SEQUENCE: 47

Met Lys Leu Thr Ser Leu Leu Leu Leu Ser Leu Thr Leu Ile Thr Lys
1               5                   10                  15

Tyr Thr Lys Ser Asn Glu Phe Arg Asp Leu Asn Asn Ala Ala Lys Asp
            20                  25                  30

Pro Asn Ser Asn Tyr Asn Pro Ser His Val Glu Ile Ile Glu Lys Asp
        35                  40                  45

Phe Glu Lys Ser Thr Leu Asp Asp Ser Glu Tyr Arg Val Val Lys Leu
    50                  55                  60

Gln Asn Gly Ile Glu Val Ala Leu Val Ser Asp Pro Ser Val Arg Leu
65                  70                  75                  80

Ala Ala Thr Ser Val Ala Val Arg Val Gly Ser Lys Asp Asp Pro Lys
                85                  90                  95

Gly Phe Pro Gly Leu Ala His Leu Cys Glu Tyr Leu Leu Phe Met Gly
            100                 105                 110

Thr Glu Lys Tyr Pro Leu Glu Asn Glu Tyr Thr Ser Phe Val Leu Asn
        115                 120                 125

His Gly Gly Ser Phe Asp Ser Tyr Arg Gly Leu Glu Arg Thr Val Phe
    130                 135                 140

Ile Ser Glu Ile Asn Pro Lys Tyr His Tyr Glu Gln Leu Asp Arg Met
145                 150                 155                 160

Ala Asn Phe Phe Ile Lys Pro Leu Phe Arg Glu Asp Leu Ile Glu Arg
                165                 170                 175

Glu Thr His Phe Ile Asn Ser Glu Phe Glu Glu Tyr Arg Ser Ser Phe
            180                 185                 190

Ser Lys Ala Arg Phe His Phe Leu Asn Tyr Ile Leu Lys Asp Thr Gly
        195                 200                 205

Leu Phe Pro Glu Phe Thr Thr Gly Asn Arg Gln Thr Leu Phe Ser Glu
    210                 215                 220

Pro Arg Ala Lys Asn Met Ser Val Lys Lys Ala Leu Glu Asp Phe Phe
225                 230                 235                 240

Asp Asn Tyr Tyr His Ser Arg Asp Ile Lys Val Ala Val Cys Gly Asn
```

-continued

```
                245                 250                 255

Glu Ser Leu Asp Thr Leu Gln Glu Leu Val Gln Lys Thr Phe Gly Gln
            260                 265                 270

Ile Pro Asp Lys Lys Glu Arg Ala Ile Asp Asp Val Asn Pro Phe Ser
        275                 280                 285

Ser Ile Thr Lys Tyr His Tyr Trp Tyr Asn Phe Ser Gly Ala Pro Tyr
    290                 295                 300

Thr Ala Asp Ile Ala Phe Ile Val Pro Ser Ser Arg Val His Tyr Lys
305                 310                 315                 320

Ser Val Pro Phe His Tyr Leu Asn Tyr Ile Phe Ser Tyr Ser Gly Pro
                325                 330                 335

Asp Ser Pro Ile Asp Tyr Phe Ser Lys Lys Ser Leu Ala Ser Arg Ile
            340                 345                 350

Arg Phe Ser Asn Ile Glu Tyr Ser Ser Lys Tyr Asp Leu Leu Phe Val
        355                 360                 365

Ser Leu Lys Pro Leu Tyr Val Gly Arg Leu Phe Tyr Glu Glu Leu Ile
    370                 375                 380

Leu Glu Phe Phe Lys Cys Ile Gln Phe Phe Lys Glu Asn Gly Pro Asn
385                 390                 395                 400

Lys Ala Val Phe Glu Asp Ile Met Lys Ala Gln Asn Thr Asn Phe Lys
                405                 410                 415

Tyr Ser Phe Lys Glu Ser Val Ser Gln Leu Val Asp Lys Leu Ser Thr
            420                 425                 430

Ser Leu Leu Ala Asp Ser Phe Pro Arg Lys Tyr Leu Leu Lys Gln Asp
        435                 440                 445

Ile Ile Lys Glu Tyr Asn Lys Glu Glu Phe Asp Glu Phe Phe Ser Ala
    450                 455                 460

Leu Asn Tyr Glu Asn Phe Ile Ser Phe Ser Asn Thr Ile Arg Lys Gly
465                 470                 475                 480

Tyr Asn Glu Thr Asp Pro Tyr Tyr Asn Ile Thr Tyr Leu Lys Gln Ser
                485                 490                 495

His Lys Lys Arg Phe Ile Glu Lys Leu Lys Asn Ile Ser Ser Pro Asn
            500                 505                 510

Leu Lys Tyr Pro Pro Lys Asn Ile Tyr Leu Asp Glu Ser Asp Ile Thr
        515                 520                 525

Met Glu Lys Leu Asn Glu Thr Leu Thr Lys Pro Asp Leu Leu Lys Asp
    530                 535                 540

Thr Tyr Val Ser Thr Leu Trp His Lys His Ala Ser Phe Phe Tyr Cys
545                 550                 555                 560

Pro Tyr Gly Val Ile Arg Ile Leu Leu Lys Asn Pro Phe Val Ser Ser
                565                 570                 575

Thr Pro Ser Asn Met Leu Lys Ile Arg Phe Leu Gln Ile Tyr Ile Tyr
            580                 585                 590

Ser Ser Leu Pro Phe Asp Phe Leu Leu Leu Ser Thr Ala Asn Val Asn
        595                 600                 605

Phe Tyr Ile Thr Pro Thr Leu His Gly Leu Ile Ile Met Phe Tyr Gly
    610                 615                 620

Tyr Thr Asn Lys Met Met Glu Leu Val Thr Arg Val Ile Asn Thr Leu
625                 630                 635                 640

Lys Glu Thr Ser Leu Asp His Arg Leu Phe Asn Pro Leu Arg Ser Thr
                645                 650                 655

Leu Ile Tyr Ser Tyr Ile Gln Arg Ile Ser Ala Glu Pro Ser Thr Phe
            660                 665                 670
```

```
Leu Glu Ile Asp Ile Asp Asp Ile Leu Phe Ser Glu Arg Gln Pro Phe
        675                 680                 685

Lys Asn Met Leu Phe Val Leu Asp Gln Phe Gln His Ser Asp Val Asn
    690                 695                 700

Ala Phe Phe Tyr Asn Leu Leu Asn Asn Phe His Phe Asp Val Leu Ile
705                 710                 715                 720

Thr Gly Asn Ile Pro Lys Glu Asp Ala Leu His Ile His Asn Met Leu
                725                 730                 735

Glu Thr Thr Phe Ser Pro His Pro Leu Thr Ser Ser Gln Arg His Tyr
            740                 745                 750

Ile Asn Thr Arg Ala Ile Thr Leu Glu Asp Gly Ser Asp Tyr Phe Arg
        755                 760                 765

Val His Glu Leu Ser Lys Ser Gly Pro Lys Ser Ala Leu Phe Met Tyr
    770                 775                 780

Phe Glu Ala Ala Glu Met Glu Asp Ser Arg Arg Val Met Leu Phe Leu
785                 790                 795                 800

Ile Leu Tyr Leu Ile Leu Arg Glu Pro Ile Tyr His Glu Leu Lys Thr
                805                 810                 815

Lys Glu Gln Leu Gly His Ile Ile Lys Ser Asp Ile Lys Val Ser Arg
            820                 825                 830

Asn Ile Leu Gly Tyr Tyr Ile Leu Val Gln Ser Glu Arg Gln Pro His
        835                 840                 845

Val Leu His Ser Arg Ile Asp Ala Phe Leu Asn Arg Met Leu Asp Arg
    850                 855                 860

Ile Leu Asn Leu Thr Ser Lys Glu Leu Asn Tyr His Leu Glu Ser Leu
865                 870                 875                 880

Gln Tyr Phe Leu Lys Lys Asp Pro Ser Asn Ile Leu Ser Glu Asn Leu
                885                 890                 895

Asn Val Trp Ser Ser Val Val Asn Ala Pro Tyr Thr Ser Asn Ser Asp
            900                 905                 910

Phe Glu Pro Gln Lys Ala Asp Pro Ile Glu Pro His Glu Leu Val Asn
        915                 920                 925

Leu Phe Lys Glu Val Phe Tyr Ser Lys Arg Lys Arg Phe Ser Tyr Thr
    930                 935                 940

Val Thr Ser Thr Val Thr Ser Asp Ile Tyr Asn Leu Tyr Asp Leu Pro
945                 950                 955                 960

Leu Asp Lys Leu Ser Glu Tyr Leu Ser Ser Lys Gly Glu Asn Val Ser
                965                 970                 975

Lys Glu Glu Leu Tyr Asn Tyr Val Leu Leu Ser His Asp Phe Pro Ser
            980                 985                 990

Phe Arg Ile Lys Leu Ser Glu His  Leu Ser Lys Asn Arg  Asn Gln Ser
        995                 1000                1005

Asp Val  Lys Ser Ile Leu Asp  Glu Thr Ile Lys Tyr  Leu Lys Arg
    1010                1015                1020

Leu Tyr  Leu Leu Glu Lys Tyr  Arg Ile Leu Lys Pro  Leu Ser Leu
    1025                1030                1035

Val Asp  Asn Ile Ala Tyr Phe  Lys Ala Ser Leu Glu  Leu Ser Pro
    1040                1045                1050

Ala Phe  Val Tyr Asn Ser Leu  Ser Ser Glu Tyr His  Lys
    1055                1060                1065
```

<210> SEQ ID NO 48
<211> LENGTH: 3281

<212> TYPE: DNA
<213> ORGANISM: Artificial sequence
<220> FEATURE:
<223> OTHER INFORMATION: Codon-optimized sequence

<400> SEQUENCE: 48

```
gtcgacatgt actccatgca gctcgcttct tgcgttacct tgactctggt gctgctcgtc     60
aacagcatga aactcacttc tctcctcctc ctctctctga cactcatcac taaatacact    120
aaatctaatg aattccggga cctcaataat gctgccaagg accctaacag taattacaac    180
ccatcacacg tggagatcat tgaaaaggat ttcgaaaaaa gcactctgga cgattccgag    240
tatagagtgg tcaagctcca gaacgggatc gaggtcgcac tggtgtcaga ccctagcgtg    300
cgactggcag ctaccagcgt ggccgtcagg gtggggtcca aggacgatcc aaaagggttt    360
cccggtctgg ctcacctctg cgaatacctg ctcttcatgg gtaccgagaa gtacccactg    420
gagaacgaat atacatcctt tgtgctgaat cacggcggca gcttcgattc ttatagaggc    480
ctggaacgga cagtcttcat ctctgagatt aacccaaaat accattatga gcagctggac    540
cggatggcca atttctttat caagcccctc tttagggagg atctgatcga gagagaaact    600
cacttcatta acagcgaatt tgaggaatac agaagctcct tctccaaagc tcggttccat    660
tttctcaatt atatcctgaa ggacactggg ctgttccccg agtttaccac aggtaaccgc    720
cagaccctgt tctctgaacc tcgagcaaag aatatgagtg tgaagaaagc cctggaggac    780
ttctttgata actactatca ctcaagggac atcaaagtcg ccgtgtgcgg caatgaaagc    840
ctggatactc tccaggagct ggtgcagaag acctttggac agatccctga caagaaggag    900
agagctattg acgatgtgaa cccattctct agtatcacaa agtaccatta ctggtacaac    960
ttttccgggg caccttacac tgctgatatc gcattcattg tcccatcaag ccgggtgcac   1020
tataagtccg tccccttca ttatctgaac tacatcttct cttacagtgg tcctgactct   1080
ccaatcgatt acttcagtaa gaaatcactg gctagcagga tcaggttcag caacattgag   1140
tattcctcta aatacgacct gctctttgtg tctctcaagc cactgtacgt cggccgcctg   1200
ttctatgagg aactcatcct ggagttcttt aagtgtatcc agttctttaa ggagaacgga   1260
cccaacaagg ctgtgttcga agatatcatg aaagcacaga acactaactt caagtactct   1320
tttaaagagt cagtcagcca gctcgtggac aagctgtcca cctctctgct cgctgatagc   1380
tttccacgga agtacctgct caaacaggac atcattaagg aatacaacaa agaggaattc   1440
gatgagttct ttagcgcact gaattacgaa aacttcatca gtttttcaaa caccatccgg   1500
aaaggataca acgagaccga cccctactat aatatcacat atctgaagca gtcccacaag   1560
aaacgcttca tcgaaaagct gaaaaacatc agttcaccta acctgaagta ccccccctaaa   1620
aacatctatc tggacgagag cgatattaca atggagaagc tcaatgaaac actgactaag   1680
cctgacctgc tcaaagatac ctacgtgtca acactgtggc acaagcatgc aagcttcttt   1740
tattgtccat acggcgtgat ccgcattctg ctcaaaaacc cctttgtcag ctccacccct   1800
tccaatatgc tcaagatccg attcctgcag atctatatct actctagtct gcctttcgac   1860
tttctgctcc tgtctacagc taatgtgaac ttttacatta ccccaacact ccacggcctg   1920
atcatcatgt tctacggata cacaaacaaa atgatggagc tggtcactag agtgatcaac   1980
actctgaagg aaacctccct cgaccatcgg ctgttcaacc ccctccgctc taccctgatc   2040
tacagttaca tccagaggat ttccgccgaa ccttctacat ttctggagat cgatattgac   2100
gatatcctgt tcagcgagag acagccattc aagaacatgc tctttgtgct ggaccagttc   2160
```

-continued

```
cagcactccg atgtcaatgc attcttttac aacctcctga acaatttcca ttttgacgtg   2220

ctgatcacag gcaacattcc caaggaggat gccctccaca tccataatat gctggaaact   2280

accttttctc cacacccct gacttcaagc cagcgacatt acatcaacac aagggccatt   2340

actctggagg acggcagcga ttatttcaga gtgcacgaac tgagcaagtc cggacccaaa   2400

agtgctctgt tcatgtactt tgaggcagcc gagatggaag acagcaggag agtgatgctc   2460

ttcctgatcc tctacctgat tctccgagag cctatctatc acgaactcaa gaccaaagag   2520

cagctggggc atatcattaa gtcagatatc aaggtgagcc gcaacatcct cggttactat   2580

attctggtgc agtccgagag gcagccccac gtcctgcatt ctagaatcga cgcctttctc   2640

aatcgcatgc tggatcgaat tctgaacctc accagtaagg aactgaatta ccacctcgag   2700

tcactgcagt atttcctgaa gaaagaccct agtaacatcc tctcagagaa tctgaacgtg   2760

tggtcctctg tggtcaatgc cccatacaca tctaacagtg acttcgagcc ccagaaagct   2820

gatcccatcg agcctcatga actcgtgaac ctgttcaagg aagtctttta cagtaagcga   2880

aaaaggttct catatactgt caccagcaca gtgacttccg acatctataa tctgtacgac   2940

ctgcctctcg ataagctctc tgaatacctg agttcaaaag gagagaacgt cagtaaggag   3000

gaactgtata attacgtcct cctgtcccac gatttcccat cttttagaat caaactctct   3060

gagcatctga gtaagaatcg gaaccagtca gacgtgaaga gcatcctgga tgagaccatt   3120

aagtatctca aacggctgta cctcctggaa aagtatcgca tcctgaaacc actgagcctc   3180

gtggacaaca ttgcctactt taaggcttcc ctggagctct ctcccgcctt cgtctacaat   3240

tccctgagct ccgaatatca caagtgagga tccgcggccg c                       3281
```

<210> SEQ ID NO 49
<211> LENGTH: 311
<212> TYPE: PRT
<213> ORGANISM: Pneumocystis murina
<220> FEATURE:
<221> NAME/KEY: MISC_FEATURE
<222> LOCATION: (1)..(311)
<223> OTHER INFORMATION: P. murina hypothetical protein PNEG_01231

<400> SEQUENCE: 49

```
Met Ala Asn Lys Thr Asp Pro Gln Ser Asn Phe Phe Ile Asp Phe Met
1               5                   10                  15

Met Gly Gly Val Ser Ala Ala Val Ala Lys Thr Ser Ala Ala Pro Ile
            20                  25                  30

Glu Arg Val Lys Leu Leu Ile Gln Asn Gln Asp Glu Met Ile Lys Ser
        35                  40                  45

Gly Arg Leu Ser Gln Arg Tyr Thr Gly Ile Ile Asn Cys Phe Ser Arg
    50                  55                  60

Thr Val Lys Asp Glu Gly Ile Ile Ser Leu Trp Arg Gly Asn Thr Ala
65                  70                  75                  80

Asn Val Leu Arg Tyr Phe Pro Thr Gln Ala Leu Asn Phe Ala Phe Lys
                85                  90                  95

Asp Lys Phe Lys Lys Met Phe Gly Phe Lys Lys Asp Arg Asp Gly Tyr
            100                 105                 110

Trp Pro Trp Phe Phe Gly Asn Leu Ala Ser Gly Gly Cys Ala Gly Ala
        115                 120                 125

Ala Ser Leu Leu Phe Val Tyr Ser Leu Asp Tyr Ala Arg Thr Arg Leu
    130                 135                 140

Ala Asn Asp Ala Lys Ser Ala Lys Lys Gly Gly Glu Arg Gln Phe Asn
145                 150                 155                 160
```

Gly Leu Ile Asp Val Tyr Lys Lys Thr Leu Ala Ser Asp Gly Ile Arg
165 170 175

Gly Leu Tyr Arg Gly Phe Gly Pro Ser Val Ala Gly Ile Ile Val Tyr
180 185 190

Arg Gly Leu Tyr Phe Gly Leu Tyr Asp Ser Val Lys Pro Val Val Leu
195 200 205

Thr Gly Pro Leu Glu Gly Ser Phe Ile Ala Ser Phe Val Leu Gly Trp
210 215 220

Ile Val Thr Thr Thr Ser Gly Leu Ala Ser Tyr Pro Ile Asp Thr Val
225 230 235 240

Arg Arg Arg Met Met Met Thr Ser Gly Glu Ala Val Lys Tyr Ser Ser
245 250 255

Ser Phe Gln Ala Phe Ser Gln Ile Ile Ala Lys Glu Gly Ser Arg Ser
260 265 270

Leu Phe Lys Gly Ala Gly Ala Asn Ile Leu Arg Gly Val Ala Ala Ala
275 280 285

Gly Val Ile Ser Met Tyr Asp Gln Leu Gln Met Ile Val Phe Gly Lys
290 295 300

Lys Tyr Ser Gly Gly Ser Gly
305 310

<210> SEQ ID NO 50
<211> LENGTH: 603
<212> TYPE: PRT
<213> ORGANISM: Pneumocystis murina
<220> FEATURE:
<221> NAME/KEY: MISC_FEATURE
<222> LOCATION: (1)..(603)
<223> OTHER INFORMATION: P. murina major surface glycoprotein family
PNEG_01377

<400> SEQUENCE: 50

Met Ala Gln Pro Val Lys Arg Gln Ala Ala Gly Gln Ala Ala Gly Asn
1 5 10 15

Asp Glu Ile Lys Glu Glu Gln Val Leu Gly Leu Ile Val Lys Ser Tyr
20 25 30

Tyr Ser Asp Asp Asn Lys Cys Lys Ala Asn Leu Lys Gln Tyr Cys Glu
35 40 45

Glu Leu Lys Lys Ile Asp Gly Lys Leu Glu Ser Val Asp Val Lys Val
50 55 60

Lys Gly Leu Cys Glu Asn Gly Lys Glu Gly Glu Lys Cys Lys Glu Leu
65 70 75 80

Lys Lys Lys Leu Glu Thr Glu Leu Gly Ala Phe Lys Thr Glu Val Glu
85 90 95

Asn Ala Leu Asn Asn Leu Thr Asp Glu Lys Cys Arg Lys Tyr Glu Glu
100 105 110

Lys Cys Leu Leu Leu Glu Glu Ala Asp Pro Asn Asn Leu Glu Glu Lys
115 120 125

Cys Val Lys Leu Arg Asp Arg Cys Tyr Arg Gln Arg Arg Gln Gly Val
130 135 140

Ala Lys Glu Ile Leu Leu Arg Ala Leu Glu Gly Lys Val Asn Asn Lys
145 150 155 160

Asp Glu Cys Lys Lys Arg Met Lys Glu Ile Cys Gln Gly Leu Ser Glu
165 170 175

Tyr Ser Asp Glu Leu Val Phe Ser Cys Phe Asn Ser Asp Lys Thr Cys
180 185 190

```
Glu Tyr Leu Gln Lys Asn His Gly Asp Ser Cys Lys Pro Leu Glu Lys
        195                 200                 205

Glu Leu Glu Asp Lys Glu Leu Val Glu Lys Cys Gln Glu Tyr Leu Glu
    210                 215                 220

Lys Cys Tyr Phe Tyr Gly Ser Ser Cys Lys Asp Thr Lys Cys Asp Lys
225                 230                 235                 240

Val Lys Asn Lys Cys Lys Gly Lys Gly Ile Glu Tyr Glu Gly Pro Lys
                245                 250                 255

Leu Asp Phe Ser Pro Val Arg Glu Lys Pro Arg Phe Pro Glu Lys Ile
            260                 265                 270

Glu Val Glu Asn Leu Tyr Lys Lys Glu Glu Ala Lys Gly Ile Ile Val
        275                 280                 285

Gly Lys Pro Lys Tyr Lys Thr Leu Arg Asp Leu Ala Leu Leu Leu Ile
    290                 295                 300

Lys Glu Arg Asn Gly Lys Asp Glu Gly Glu Lys Cys Lys Lys Ala Leu
305                 310                 315                 320

Glu Asp Cys Glu Ser Phe Lys His Leu Asp Tyr Gly Leu Glu Glu Leu
                325                 330                 335

Cys Gly Asp Lys Asp Lys Asp Asn Lys Cys Lys Glu Leu Val Glu Val
            340                 345                 350

Glu Asp Arg Cys Thr Asn Phe Lys Leu Glu Leu Tyr Ile Lys Gly Leu
        355                 360                 365

Ser Thr Lys Phe Glu Asp Ile Glu Ser Asp Tyr Phe Ser Trp Gly Gln
    370                 375                 380

Val Ser Lys Ser Val Ser Arg Glu Asp Cys Ile Lys Phe Glu Ser Glu
385                 390                 395                 400

Cys Phe His Leu Glu Gly Val Cys Thr Asn Lys Ile Gly Lys Ala Cys
                405                 410                 415

Glu Asn Val Arg Val Ala Cys Tyr Lys Lys Gly Gln Asp Arg Val Leu
            420                 425                 430

Asn Arg Tyr Phe Gln Glu Gly Leu Lys Gly Leu Ile Gly Asp Leu Glu
        435                 440                 445

Leu Val Thr Glu Asn Leu Glu Lys Cys Gln Lys Ser Val Val Gly Asn
    450                 455                 460

Tyr Thr Lys Leu Lys Glu Asp Arg Arg Tyr Phe Thr Lys Cys His Arg
465                 470                 475                 480

Pro Thr Glu Leu Cys Tyr Glu Leu Leu Asp Asp Val Ile Leu Gln Ser
                485                 490                 495

Glu Glu Leu Glu Val Val Leu Asn Leu Arg Arg Asp Phe Pro Arg Lys
            500                 505                 510

Glu Asp Cys Val Glu Leu Lys Lys Lys Cys Lys Asp Leu Glu Ser Asp
        515                 520                 525

Ser Tyr Leu Asn His Glu Lys Cys Asn Thr Leu Asn Arg Arg Cys Glu
    530                 535                 540

Tyr Leu Lys Val Thr Glu Glu Leu Arg Lys Arg Leu Leu Lys Arg Gly
545                 550                 555                 560

Asp Asp Ala Leu Arg Thr Gln Gly Asn Cys Thr Ala Val Leu Lys Lys
                565                 570                 575

Glu Cys Glu Glu Leu Ser Arg Arg Gly Lys Glu Asp Phe Ser Val Ser
            580                 585                 590

Cys Ala Leu Arg Glu Glu Thr Cys Ser Phe Met
        595                 600
```

<210> SEQ ID NO 51
<211> LENGTH: 183
<212> TYPE: PRT
<213> ORGANISM: Pneumocystis murina
<220> FEATURE:
<221> NAME/KEY: MISC_FEATURE
<222> LOCATION: (1)..(183)
<223> OTHER INFORMATION: P. murina hypothetical protein (HSP30-like protein) PNEG_01746

<400> SEQUENCE: 51

```
Met Ile Phe Pro Arg Met Leu Glu Thr Thr Phe Phe Pro Thr Asp Leu
1               5                   10                  15

Gly Arg Phe Ile His Ser Thr Phe Asp Glu Pro Leu Phe Tyr Phe Lys
            20                  25                  30

Glu Asn Leu Ala Asp Arg Thr Leu Ser Pro Arg Ile Asp Met Ser Glu
        35                  40                  45

Ser Ala Lys Glu Tyr Cys Val Glu Val Glu Leu Pro Gly Leu Lys Lys
    50                  55                  60

Glu Glu Ile Ile Ile Glu Phe Val Asp Gln Lys Thr Ile Val Val Gln
65                  70                  75                  80

Gly His Ile Glu Arg Leu Asn Cys Asn Lys Ser Asn Gly Asp Gly Pro
                85                  90                  95

Ile Val Glu Glu Ile Val Asp Glu Glu Pro Lys Ser Lys Ser Lys Ser
            100                 105                 110

Thr Ser Leu Lys Val Cys Glu Lys Asn Val Leu Lys Lys Ser Pro Arg
        115                 120                 125

Val Thr Tyr Trp Tyr Lys Glu Arg Ala Phe Gly Glu Phe Ser Arg Lys
    130                 135                 140

Ile Cys Phe Pro Thr Asn Val Asp Arg Asp His Val Lys Ala Thr Leu
145                 150                 155                 160

Glu Asn Gly Ile Leu Lys Ile Thr Val Pro Lys Ser Ala Cys Ser Val
                165                 170                 175

Thr Arg Arg Ile Ala Ile Asp
            180
```

<210> SEQ ID NO 52
<211> LENGTH: 632
<212> TYPE: DNA
<213> ORGANISM: Artificial sequence
<220> FEATURE:
<223> OTHER INFORMATION: Codon-optimized sequence

<400> SEQUENCE: 52

```
gtcgacatgt actccatgca gctcgcttct tgcgttacct tgactctggt gctgctcgtc     60

aacagcatga tttttcctcg gatgctcgaa acaaccttct tccctactga cctcggccgc    120

tttattcact caacttttga tgaacccctc ttttacttca aggagaacct ggcagaccgg    180

actctcagcc cacgcattga tatgagcgag tccgccaagg aatattgtgt ggaggtcgaa    240

ctgcccgggc tcaagaaaga ggaaatcatt atcgagtttg tggaccagaa aaccattgtg    300

gtccagggtc acatcgaaag gctgaactgc aataagtcta acggcgacgg acccattgtg    360

gaggaaatcg tcgatgagga acctaagtct aagagtaagt caaccagcct gaaagtgtgc    420

gagaagaatg tcctcaagaa aagtcctaga gtgacatact ggtataaaga gcgagctttc    480

ggcgaatttt ccaggaagat ctgtttccca acaaacgtgg accgggatca tgtcaaggcc    540

accctggaga atggaattct caaaatcaca gtgcccaagt ccgcctgctc tgtgactagg    600
```

agaattgcta tcgattgagg atccgcggcc gc 632

<210> SEQ ID NO 53
<211> LENGTH: 1159
<212> TYPE: PRT
<213> ORGANISM: Pneumocystis murina
<220> FEATURE:
<221> NAME/KEY: MISC_FEATURE
<222> LOCATION: (1)..(1159)
<223> OTHER INFORMATION: P. murina major surface glycoprotein_01847

<400> SEQUENCE: 53

Met Tyr Gly Tyr Phe Glu Arg Ile Ile Ser Arg Ser Thr Phe Asp Leu
1 5 10 15

Pro Ser His Met Leu Leu Arg Asp Lys Arg Trp Val Glu Glu Val Ala
20 25 30

Gln Lys Glu Ala Ala Met Ala Gln Pro Val Lys Arg Gln Ala Ala Gly
35 40 45

Gln Ala Ala Gly Asn Asp Glu Ile Lys Glu Glu Gln Val Leu Gly Leu
50 55 60

Ile Val Lys Ser Gly Tyr Asn Asn Asp Asn Lys Cys Lys Ala Asp Leu
65 70 75 80

Lys Gln Tyr Cys Glu Glu Leu Lys Lys Ile Asp Gly Lys Leu Glu Ser
85 90 95

Val Asp Val Lys Val Lys Gly Leu Cys Glu Asn Ile Asp Lys Lys Cys
100 105 110

Gly Asp Leu Lys Asp Lys Val Lys Thr Glu Leu Asp Ala Phe Lys Thr
115 120 125

Glu Leu Glu Lys Glu Leu Asn Asn Leu Thr Asp Glu Lys Cys Arg Lys
130 135 140

Tyr Glu Glu Lys Cys Leu Leu Leu Glu Glu Ala Asp Pro Ser Asn Leu
145 150 155 160

Glu Glu Lys Cys Val Lys Leu Arg Asp Arg Cys Tyr Gly Arg Arg Arg
165 170 175

Gln Gly Val Thr Lys Glu Ile Leu Phe Arg Ala Leu Glu Gly Lys Val
180 185 190

Asn Asp Thr Asp Glu Cys Lys Lys Arg Met Lys Glu Ile Cys Gln Gly
195 200 205

Leu Ser Glu Tyr Ser Asp Glu Leu Ile Phe Ser Cys Phe Asn Ser Asp
210 215 220

Lys Thr Cys Asn Gly Leu Lys Gly Ser His Gln Asp Ser Cys Lys Ser
225 230 235 240

Leu Glu Thr Glu Leu Lys Asp Asn Glu Leu Met Glu Lys Cys Gln Glu
245 250 255

Tyr Leu Glu Lys Cys Tyr Phe Tyr Gly Ser Ser Cys Lys Asp Thr Lys
260 265 270

Cys Asp Lys Val Lys Asn Lys Cys Lys Gly Lys Gly Ile Glu Tyr Glu
275 280 285

Gly Pro Lys Leu Asp Phe Ser Pro Val Lys Glu Lys Pro Arg Phe Pro
290 295 300

Glu Lys Ile Glu Val Glu Asn Leu Tyr Lys Lys Glu Glu Ala Lys Gly
305 310 315 320

Ile Ile Val Gly Lys Pro Lys Tyr Lys Thr Leu Arg Asp Leu Ala Leu
325 330 335

Leu Leu Ile Lys Glu Arg Asn Gly Lys Asp Glu Gly Glu Lys Cys Lys
340 345 350

```
Lys Ala Leu Glu Asp Cys Glu Ser Phe Lys His Leu Asp Tyr Gly Leu
        355                 360                 365

Glu Glu Leu Cys Gly Asp Lys Asp Lys Glu Asp Arg Cys Lys Glu Leu
    370                 375                 380

Val Glu Val Glu Asp Arg Cys Thr Asn Phe Lys Leu Glu Leu Tyr Leu
385                 390                 395                 400

Lys Gly Leu Ser Thr Glu Phe Glu Lys Asp Lys Glu Ser Asp Tyr Phe
                405                 410                 415

Ser Trp Gly Gln Val Ser Lys Leu Val Ser Arg Glu Asp Cys Ile Lys
            420                 425                 430

Phe Glu Ser Glu Cys Phe His Leu Glu Gly Val Cys Thr Asn Lys Ile
        435                 440                 445

Gly Lys Ala Cys Glu Asn Val Arg Val Ala Cys Tyr Lys Lys Gly Gln
    450                 455                 460

Asp Arg Val Leu Asn Arg Tyr Phe Gln Glu Gly Leu Lys Gly Leu Ile
465                 470                 475                 480

Gly Asp Leu Glu Leu Val Thr Glu Asn Leu Glu Lys Cys Gln Lys Ser
                485                 490                 495

Val Val Gly Asn Tyr Thr Lys Leu Lys Glu Asp Arg Arg Tyr Phe Thr
            500                 505                 510

Lys Cys His Leu Pro Thr Lys Leu Cys Tyr Glu Leu Leu Asp Asp Val
        515                 520                 525

Ile Leu Gln Ser Glu Glu Leu Glu Val Val Leu Asn Leu Arg Arg Asp
    530                 535                 540

Phe Pro Arg Lys Glu Asp Cys Val Glu Leu Lys Lys Lys Cys Lys Asp
545                 550                 555                 560

Leu Glu Ser Asp Ser Tyr Leu Asn His Glu Lys Cys Asp Thr Leu Asn
                565                 570                 575

Arg Arg Cys Glu Tyr Leu Lys Val Thr Glu Glu Leu Arg Lys Arg Leu
            580                 585                 590

Leu Lys Arg Gly Asp Asp Ala Leu Arg Thr Gln Gly Asn Cys Thr Ala
        595                 600                 605

Val Leu Lys Lys Glu Cys Glu Glu Leu Ser Arg Arg Gly Lys Glu Asp
    610                 615                 620

Phe Ser Val Ser Cys Ala Leu Arg Glu Glu Thr Cys Ser Phe Met Val
625                 630                 635                 640

Glu Gln Thr Glu Asn Glu Cys Leu Phe Leu Lys Asn Asn Met Asp Ile
                645                 650                 655

Gly Lys Ile Ile Glu Lys Ile Glu Asn Gly Lys Arg Asn Glu Thr Leu
            660                 665                 670

Val Glu Glu Leu Cys Thr Leu Phe Asp Pro Tyr Cys His Gln Tyr Ile
        675                 680                 685

Glu Asn Cys Pro Asp Arg Leu Lys Lys Thr Asn Asn Ala Gly Arg Lys
    690                 695                 700

Gly Val Cys Leu Glu Leu Glu Glu Lys Cys Lys Pro Phe Phe Glu Lys
705                 710                 715                 720

Leu Lys Leu Glu Asn Glu Leu Thr His Lys Leu Lys Gly Ser Leu Ser
                725                 730                 735

Asp Glu Thr Lys Cys Lys Glu Thr Leu Gly Lys His Cys Thr Glu Trp
            740                 745                 750

Lys Lys Glu Gly Asn Gln Thr Leu Asn Ser Leu Cys Glu Asp Ala Lys
        755                 760                 765
```

```
Lys Glu Glu Leu Cys Lys Lys Leu Val Lys Lys Val Lys Glu Lys Cys
    770                 775                 780

Pro Thr Leu Lys Asn Lys Leu Asp Asn Glu Lys Asp Glu Leu Glu Lys
785                 790                 795                 800

Lys Lys Asp Glu Tyr Glu Lys Val Lys Gln Glu Ser Glu Lys Phe Ala
                805                 810                 815

Lys Glu Ala Lys Leu Val Leu Ser Arg Pro Glu Gln Asn Gly Gln Gly
            820                 825                 830

Gly Gly Ser Lys Ala Gln Asp Gly Ser Val Pro Lys Pro Val Gly Pro
        835                 840                 845

Pro Val Gln Pro Pro Ala Pro Ala Gln Pro Thr Pro Gly Gly Val Pro
    850                 855                 860

Val Pro Ala Pro Thr Leu Ala Pro Pro Ala Gln Pro Thr Ser Gly Gly
865                 870                 875                 880

Ala Pro Leu Pro Val Pro Pro Ala Ala Pro Gly Gly Thr Pro Gly Gly
                885                 890                 895

Ala Pro Val Pro Val Pro Pro Pro Ala Pro Gly Thr Pro Pro Ala Gly
            900                 905                 910

Pro Ala Gly Pro Ser Gly Pro Ser Gly Gly Thr Pro Ala Gly Pro Pro
        915                 920                 925

Ala Pro Gly Gly Ser Thr Pro Ser Gly Thr Thr Asn Thr Ser Asn Val
    930                 935                 940

Ile Leu Val Arg Arg Thr Phe Val Ser Gly Glu Val Ser Glu Pro Glu
945                 950                 955                 960

Lys Lys Ala Phe Val Ala Thr Ala Arg Ala Leu Glu Leu Tyr Leu Glu
                965                 970                 975

Leu Lys Glu Lys Cys Lys Gly Leu Gln Gly Asp Cys Gly Phe Arg Lys
            980                 985                 990

Asp Cys Pro Gly Cys Glu Ala Ala  Cys Lys Glu Ile Asp  Lys Leu Cys
        995                 1000                1005

Glu Gly  Ile Glu Gly Leu Lys  Val Thr Pro His His  Thr Val Ile
    1010                1015                1020

Ser Thr  Ala Thr Gln Thr Thr  Thr Thr Thr Ala Thr  Thr Thr Thr
    1025                1030                1035

Thr Thr  Thr Thr Thr Thr Thr  Thr Thr Thr Thr Thr  Thr Thr Thr
    1040                1045                1050

Ala Thr  Thr Thr Glu Ser Val  Asp Gly Gly Lys Val  Thr Glu Glu
    1055                1060                1065

Cys Thr  Leu Val Gln Thr Thr  Asp Thr Trp Val Thr  Ser Thr Ser
    1070                1075                1080

Leu His  Thr Ser Thr Leu Thr  Ser Thr Ser Thr Val  Thr Ser Thr
    1085                1090                1095

Val Thr  Leu Thr Ser Met Arg  Lys Cys Lys Pro Thr  Arg Cys Thr
    1100                1105                1110

Ser Asp  Ser Ser Lys Glu Thr  Glu Thr Gln Lys Glu  Glu Glu Lys
    1115                1120                1125

Glu Glu  Glu Val Lys Pro Asn  Glu Gly Met Lys Ile  Arg Val Pro
    1130                1135                1140

Glu Met  Ile Lys Ile Met Leu  Leu Gly Val Ile Val  Met Glu Leu
    1145                1150                1155

Leu
```

<210> SEQ ID NO 54

<211> LENGTH: 500
<212> TYPE: PRT
<213> ORGANISM: Pneumocystis murina
<220> FEATURE:
<221> NAME/KEY: MISC_FEATURE
<222> LOCATION: (1)..(500)
<223> OTHER INFORMATION: P. murina hypothetical protein (thioredoxin-
like) PNEG_03149

<400> SEQUENCE: 54

```
Met Ala Tyr Phe Thr Phe Phe Pro Tyr Leu Phe Ile Phe Phe Cys Phe
1               5                   10                  15

Phe Phe Val Ser Gln His Phe Ile Lys Ala Ser Asp Val Leu Asn Leu
            20                  25                  30

Asn Glu Val Ala Phe Lys Gln Thr Ile Gln Lys Pro Gly Ile Phe Leu
        35                  40                  45

Val Glu Phe Phe Ala Pro Trp Cys Gly His Cys Lys Ala Leu Ala Pro
    50                  55                  60

Glu Tyr Glu Thr Ala Ala Thr Leu Leu Lys Glu Lys Gly Ile Thr Leu
65                  70                  75                  80

Ile Gln Val Asp Cys Thr Ile Glu Thr His Leu Cys Glu Glu Tyr Asp
                85                  90                  95

Ile Ser Gly Tyr Pro Thr Leu Lys Ile Phe Arg Asp Gly Lys His Glu
            100                 105                 110

Pro Tyr Asp Gly Pro Arg Lys Ser Ser Ser Ile Val Ser Phe Met Ile
        115                 120                 125

Lys Gln Thr Leu Pro Leu Ile Thr Glu Val Asp Arg Glu Asn Phe Asp
    130                 135                 140

Phe Phe Lys Thr Ser Asp Glu Ile Val Ile Leu Ala Phe Leu Asp Lys
145                 150                 155                 160

Glu Asp Lys Ala Asn Asp Ile Tyr Thr Lys Leu Ala Thr Thr Tyr Arg
                165                 170                 175

Asn Lys Tyr Val Phe Gly Ile Thr Ser Asp Val Ser Leu Ala Lys Glu
            180                 185                 190

Phe Asn Leu Ser Leu Pro Gly Leu Ala Ile Phe Lys Thr Phe Asp Asp
        195                 200                 205

Pro Val Ser Val Phe Lys Lys Asp Phe Glu Tyr Asp Ser Leu Glu Leu
    210                 215                 220

Phe Leu Leu Ser Glu Ser Ile Pro Leu Phe Gly Glu Leu Gly Pro Asp
225                 230                 235                 240

Thr Tyr Gln Leu Tyr Ile Ser Ser Lys Ser Pro Leu Gly Cys Val Phe
                245                 250                 255

Val Ser Ser Asp Gln Glu Lys Glu Val Met Lys Asp Leu Phe Val His
            260                 265                 270

Phe Ala Lys Lys Tyr Lys Gly Lys Leu Asn Phe Ala Thr Ile Asp Gly
        275                 280                 285

Asn Leu Tyr Gly Gly His Ala Asp Asn Leu Asn Leu Lys Gln Lys Trp
    290                 295                 300

Pro Ala Phe Ala Ile Gln Glu Val Asn Ser Asn Lys Lys Phe Pro Phe
305                 310                 315                 320

Asp Gln Glu Lys Leu Leu Thr Lys Glu Asn Ile Gln Gln Phe Leu Glu
                325                 330                 335

Asp Tyr Phe Ser Gln Arg Leu Val Pro Ser Ile Lys Ser Glu Pro Ile
            340                 345                 350

Pro Glu Thr Gln Glu Gly Pro Val Thr Val Val Val Ala Lys Asn Phe
        355                 360                 365
```

```
Arg Glu Val Val Ile Glu Ser Ser Lys Asp Val Leu Val Glu Phe Tyr
    370                 375                 380

Ala Pro Trp Cys Gly His Cys Lys Asn Leu Ala Pro Lys Tyr Glu Glu
385                 390                 395                 400

Leu Ala Lys Ile Phe Ser Ser Asn Ser Glu Leu Ser Ser Lys Val Leu
                405                 410                 415

Ile Ala Lys Phe Asp Ala Thr Ala Asn Asp Val Glu Asp Asn Leu Asp
            420                 425                 430

Ile Arg Gly Phe Pro Thr Ile Leu Leu Phe Pro Ala Tyr Asp Lys Gly
        435                 440                 445

Asn Pro Val Glu Tyr Asn Gly Pro Arg Thr Val Asn Asp Met Ile Asn
    450                 455                 460

Phe Ile Phe Gln Lys Gly Thr His Lys Val Asp Ala Ser Lys Ser Val
465                 470                 475                 480

Asp Asp Lys Met Asp Glu Lys Leu Arg Asp Ser Leu Pro Ile Phe Asp
                485                 490                 495

His Asp Glu Leu
            500
```

<210> SEQ ID NO 55
<211> LENGTH: 1583
<212> TYPE: DNA
<213> ORGANISM: Artificial sequence
<220> FEATURE:
<223> OTHER INFORMATION: Codon-optimized sequence

<400> SEQUENCE: 55

```
gtcgacatgt actccatgca gctcgcttct tgcgttacct tgactctggt gctgctcgtc      60

aacagcatgg cttattttac tttcttcccc tacctcttca ttttcttctg tttcttcttc     120

gtctctcagc actttatcaa ggcttcagat gtgctgaacc tcaatgaggt cgcattcaag     180

cagaccatcc agaaacctgg gatttttctg gtggaattct ttgccccatg gtgcggtcac     240

tgtaaggcac tggcccccga gtacgaaact gccgctaccc tgctcaagga gaaagggatc     300

acactgattc aggtggattg cacaatcgaa actcacctgt gtgaggaata cgacatctcc     360

ggttatccca ctctgaagat tttcagggat ggcaaacatg agccatatga cggacccaga     420

aagagctcct ctatcgtgag ttttatgatc aagcagaccc tgcctctcat tacagaggtg     480

gatagagaaa acttcgactt ctttaagacc tcagatgaga tcgtgattct ggcttttctc     540

gacaaggaag ataaagcaaa cgacatctac accaagctgg ccaccacata ccggaacaag     600

tatgtcttcg gcattacatc tgacgtcagt ctggccaagg agtttaacct gagtctcccc     660

ggactggcta tcttcaagac ctttgacgat cctgtctccg tgttcaagaa agattttgag     720

tatgactctc tggaactctt cctgctcagt gagtcaatcc cactgtttgg ggaactcggt     780

cccgacacat accagctgta tattagttca aagtccccac tcggctgcgt cttcgtgagc     840

tccgatcagg agaaggaagt catgaaagac ctgttcgtgc actttgctaa gaaatacaag     900

ggcaaactga acttcgcaac tatcgatgga aatctgtatg gcggacatgc tgacaacctg     960

aatctcaagc agaaatggcc agctttcgca atccaggagg tgaactccaa taagaaattc    1020

ccctttgatc aggagaagct gctcacaaaa gaaaacattc agcagttcct ggaggactac    1080

ttttctcagc gactcgtgcc ttcaatcaag agcgaaccca ttcctgagac tcaggaagga    1140

ccagtgaccg tggtcgtggc taagaatttc agggaggtcg tgatcgaatc tagtaaagac    1200

gtcctggtgg agttttacgc accttggtgc gggcattgta agaacctggc accaaaatat    1260
```

-continued

```
gaggaactcg ccaagatctt ctcaagcaat tctgagctgt cctctaaggt cctcattgct   1320

aaatttgatg ccactgctaa cgacgtggag gataatctgg acatccgggg cttccctacc   1380

attctgctct ttccagccta cgacaagggg aaccccgtcg agtataatgg tcctcgcaca   1440

gtgaacgata tgatcaactt catcttccag aagggaactc acaaagtgga cgccagcaag   1500

tccgtggacg ataagatgga tgagaaactg agggacagcc tccccatctt cgaccatgat   1560

gaactgtgag gatccgcggc cgc                                            1583
```

<210> SEQ ID NO 56
<211> LENGTH: 1945
<212> TYPE: PRT
<213> ORGANISM: Pneumocystis murina
<220> FEATURE:
<221> NAME/KEY: MISC_FEATURE
<222> LOCATION: (1)..(1945)
<223> OTHER INFORMATION: P. murina hypothetical protein PNEG_03306

<400> SEQUENCE: 56

```
Met Ser Phe Phe Val Leu Lys Lys Ser Leu Asp Thr Leu Leu Tyr Lys
1               5                   10                  15

Phe Ser Ser Leu Glu Thr Cys Ser Pro Ala Thr Leu Gln Glu Ile Thr
            20                  25                  30

Lys Ile Leu Thr Glu Asp Ser Val Leu Arg Pro Ile Ser Glu Asn Ser
        35                  40                  45

Arg Gly Gly Leu Met Ser Ser Gly Lys Ser Asp Arg Asn Phe Ser Lys
    50                  55                  60

Val Lys Lys Glu Asn Lys Val Phe Thr Leu Lys Asn Asp Ile Val Asp
65                  70                  75                  80

Arg Pro Glu Phe Ala Ile Lys Val Phe Asn Glu Cys Leu Lys Val Leu
                85                  90                  95

Ser Gln Ile Val Lys Lys Ser Val Asp Cys Arg Lys Asp Phe Arg Gly
            100                 105                 110

Leu Glu Ser Lys Lys Asn Ile His Tyr Ser Asn Gly Ser Asn Tyr Ile
        115                 120                 125

Gly Leu Ala Lys Gln Ile Val Asn Cys Leu Leu Leu Ser Phe Lys Ile
    130                 135                 140

Ile Arg Glu Asn Ser Ser Lys Leu Asn Ile Lys Gln Leu Gly Val Cys
145                 150                 155                 160

Lys Ala His Ala Asn Ile Ile Asn Arg Leu Ile Asp Leu Glu Met Ile
                165                 170                 175

Ser Met Ala Phe Glu Glu Leu Ile Ser Leu Arg Asn Asp Leu Glu Cys
            180                 185                 190

Tyr Ile Arg Leu Ile Val Glu Gln Gly Phe Trp Ala Lys Ser Ser Lys
        195                 200                 205

Gln Asn Lys Leu Lys Ile Asn Glu Thr Asn Lys Ala Ile His Glu Ile
    210                 215                 220

Val Ala Trp Leu Ile Asn Ile Glu Ser Pro Val Asp Ser Leu Glu Glu
225                 230                 235                 240

Asp Val Val Asn Phe Ile Val Gly Phe Gln Leu Met Ala Leu Arg Phe
                245                 250                 255

Ala Ser Arg His Gln Asp Met Thr Leu Asp Glu Ser Leu Leu Asn Ser
            260                 265                 270

Phe Lys Ser Cys Phe Gly Pro Met Ala Phe Phe Arg Arg Leu Asn Gln
        275                 280                 285
```

-continued

```
Leu Asn Pro Lys Leu Gly Lys Asn Gln Ala Asn Leu Leu Tyr Arg Val
    290                 295                 300

Val Leu Lys Leu Cys Ser Ser His Phe Ser Tyr Ile Ser Phe Gln Phe
305                 310                 315                 320

Gln Leu Cys Thr Ile Glu Cys Leu Asp Glu Glu Asn Ile Ser Asn Asn
                325                 330                 335

Asp Asn Ile Met Asp Gly Ile Leu Arg Val Ile Ile His Leu Ser Lys
            340                 345                 350

Ile Asn Asp Ser Leu Val Ser Tyr Ser Phe Cys Lys Glu Ala Val Glu
        355                 360                 365

Asp Phe Leu Asn Phe Thr Cys Ser Gly Ile Leu Ser Arg Thr Ala Phe
    370                 375                 380

Ile Asn Leu Ile Phe Tyr Met Ser Phe Tyr Ala Glu Gln Ile Arg Asn
385                 390                 395                 400

Tyr Ser Asp Val Leu Asn Trp Asn Met Leu Leu Ile Asn Lys Phe Gly
                405                 410                 415

Gln Asn Asp Ile Ile Ser Ile Ser Leu Ser Phe His Asn Ala Phe Phe
            420                 425                 430

Glu Leu Ser Gly Leu Phe Ser Ile Glu Asn Gly Ser Tyr Leu Lys Thr
        435                 440                 445

Ala Lys Glu Asn Leu Ser Lys Leu Leu Ser Met Asp Glu Asp Ile Gln
    450                 455                 460

Asn Ala Ser Glu Gly Glu Leu Ile Lys Leu Val Lys Ser Leu Asp Arg
465                 470                 475                 480

Leu Arg Arg Ser Cys Ile Ser Ile Ile Asp Asn Ser Thr Ser His Ser
                485                 490                 495

Gln Phe Cys Arg Ser Cys Leu Glu Ile Met Leu Glu Phe Val Arg Lys
            500                 505                 510

Tyr Asn Val Asn Asn Ile Gly Glu Lys Glu Cys Phe Lys Val Leu Gly
        515                 520                 525

Phe Asn Ile Leu Thr Ser Ile Ile Ser Phe Val Lys Thr Asp Leu Thr
    530                 535                 540

Cys Ser Pro Pro Asp Lys Val Asp His Leu Ile His Leu Leu Gly Ile
545                 550                 555                 560

Ser Leu Glu Phe Ala Lys Ser Val Asn Asp Ile Ser Ala Ile Ile Ser
                565                 570                 575

Ile Ser Asn Val Phe Trp Asn Phe Gly Ile Thr Leu His Gln Asn Gly
            580                 585                 590

Asp Asn Ala Ile Asp Pro Ile Gln Arg Ser Ile Leu Ala Leu Glu Ser
        595                 600                 605

Ile Asn Phe Ser Asn Leu Asp Met Asp His Tyr Ile Gly Arg Tyr Glu
    610                 615                 620

Leu Leu Ile Lys Cys Tyr Ser Leu Ile Lys Asp Tyr Glu Asn Ser Ile
625                 630                 635                 640

Asn Tyr Cys Phe Lys Ala Met Asp Ile Leu Phe Lys Ser Gly Ile Ile
                645                 650                 655

Ser Gln Ile Ala Ser Glu Cys Asn Ser Ala Met Leu Ser Asp Val Phe
            660                 665                 670

Lys Glu His Arg His Val Ala Arg Ile Ile Thr Ser Ile Val Gln Asn
        675                 680                 685

Ala Ile Val Gly Glu Cys Trp Ser Glu Arg Cys Leu Leu Lys Tyr Leu
    690                 695                 700

Asn Ile Tyr Glu Arg Gly Pro Leu Leu Glu Trp Gln Leu Gln Val Val
```

-continued

```
705                 710                 715                 720

Leu Gly Leu Gln Tyr Lys Tyr Asp Ile Ser Lys Gln Leu Tyr Ile Leu
                725                 730                 735

Gln Asn Asn Leu Met Asp Ile Tyr Asn Glu Asn Phe Pro Val Arg Arg
            740                 745                 750

Thr Arg Val Leu Leu Gln Ile Tyr Gln Cys Leu Glu Asn Ile Thr Ser
        755                 760                 765

Glu Met Asn Asp Ala Phe Glu Glu Leu Phe Arg Lys Gly Ile Ser Asp
    770                 775                 780

Leu Met Asp Asn Asn Leu Leu Glu Asp Ile Ser Phe Glu Ser Phe Arg
785                 790                 795                 800

Tyr Asn Tyr Ile Ala Leu Ser Arg Ser Phe Leu Ala Leu Lys Leu Phe
                805                 810                 815

Leu Asn Gln Lys Gln Trp Gln Asp Asp Met Lys Ala Ala Phe Lys Ile
            820                 825                 830

Trp Lys Met Leu Phe Asp Asp Ile Glu His Ser Lys Thr Gln Lys Thr
        835                 840                 845

Leu Gly Ile Cys Ile Asp Asn Pro Leu Asn Leu Leu Cys His Phe Glu
    850                 855                 860

Met Leu Thr Asp Phe Phe Leu Val Lys Gly Leu Pro Leu Asn Arg Leu
865                 870                 875                 880

Ala Val Leu Lys Leu Arg Leu Arg Leu Cys Leu Leu Ser Pro Glu Leu
                885                 890                 895

Arg Gly Pro Gly Glu Leu Thr Arg Ile Tyr Ala Met Leu Gly Leu Gln
            900                 905                 910

Tyr Leu Tyr Leu Gly Tyr Thr Gly Lys Ala Gly Met Ile Phe Ala Thr
        915                 920                 925

Ala Gln Asn Tyr Asn Gln Lys Met Ser Leu Asp Ile Lys Ser Leu Val
    930                 935                 940

Glu Phe Glu Ile Ala Tyr Ile Glu Tyr Leu Ser Thr Val Gly Cys Ala
945                 950                 955                 960

Ser Ser Ser Trp Asn Ser Phe Ile Lys Val Ala Lys Ile Val Asn Gly
                965                 970                 975

Asn Phe Gln Ile Trp Asn Thr Gly Ile Gln Val Pro Leu Asp Gln Arg
            980                 985                 990

Ile Glu Trp Tyr Ser Leu Val Ala  Ser Gly Ser Phe Val  Tyr Ala Leu
        995                 1000                1005

Ile Met  Leu Glu Lys Gly Ala  Ile Phe Asp Ala Phe  His Tyr Val
    1010                1015                1020

Glu Asn  Ser Tyr Arg Leu Tyr  Lys Arg Ile Ile Lys  Lys Arg Phe
    1025                1030                1035

Ser Thr  Cys Asn Asp Asn Cys  Lys Lys Pro Ala Phe  Phe Glu Leu
    1040                1045                1050

Gly Arg  Ser His Trp Lys Ile  Leu Asn Asn Phe Ile  Ser Cys Leu
    1055                1060                1065

Leu Leu  Leu Ala Lys Leu Tyr  Glu Ile Gln Gly Ser  Ala Leu Asp
    1070                1075                1080

Ser Glu  Tyr Phe Tyr Ser Gln  Ala Leu Glu Val Ala  Glu Asn Ile
    1085                1090                1095

Asn Ser  Tyr Leu Ala Thr Ala  Thr Val Leu Val Met  Leu Gly Asn
    1100                1105                1110

Leu Tyr  Val Lys Thr Gly Lys  Phe Glu Lys Gly Gln  Glu Asn Phe
    1115                1120                1125
```

```
Asp Lys  Ala Lys Tyr Phe Phe  Ser Gln Ile Glu Asn  Ile Lys Glu
    1130                 1135                 1140

Ser Val  Ser Leu Leu Phe Ala  Gln Ala Asn Leu Gln  Ser Arg Gln
    1145                 1150                 1155

Lys Leu  Trp Cys Leu Glu Leu  Glu Ser Tyr Leu Leu  Ala Glu Lys
    1160                 1165                 1170

Leu Leu  Lys Glu Leu Met Ser  Pro Glu Phe Ile Ile  Lys Leu Asp
    1175                 1180                 1185

Glu Ile  Ala Met Glu Asn Val  Val Thr Gly Ile Glu  Thr Met Thr
    1190                 1195                 1200

Leu Ser  Ser Pro Ser Asn Leu  Ile Asp Ser Lys Lys  Pro Ser Phe
    1205                 1210                 1215

Asn Lys  Leu Ser Thr Gln Cys  Glu Cys Ile Val Leu  Ser Arg Leu
    1220                 1225                 1230

Lys Gly  Lys Ile Met Thr Ser  Lys Gly Tyr Asn Phe  Ala Leu Gln
    1235                 1240                 1245

Gly Lys  Ile Ile Asp Gly Lys  Lys Phe Leu Lys Glu  Ser Val Leu
    1250                 1255                 1260

Ile Glu  Cys Asp Met Asp Asp  Leu Ile Ile His Arg  Leu Tyr Gln
    1265                 1270                 1275

Ser Lys  Val Cys Phe Leu Glu  Ala Glu Val Leu Leu  Gln Asn Asp
    1280                 1285                 1290

Pro Ile  Tyr Gly Val Leu Gln  Asp Ser Val Ile Ser  Val Pro Asn
    1295                 1300                 1305

Ile Tyr  Met His Arg Ala Ser  Asp Lys Ser Val Thr  Asn Lys Thr
    1310                 1315                 1320

Lys Thr  Arg Leu Asp Val Ser  Lys Pro Gly Leu Asn  Gly Ser Arg
    1325                 1330                 1335

Gly Arg  Ile Leu Ser Leu Leu  Glu Glu Thr Lys Lys  Asn Ile Ile
    1340                 1345                 1350

Glu Ile  Phe Asn Glu Ala Leu  Asn Tyr Gly Gln Ser  Thr Leu Val
    1355                 1360                 1365

Arg Gln  Leu Ala Gln Met Met  Ala Ser Ala Thr Ile  Leu Gln Ser
    1370                 1375                 1380

Ala Leu  Tyr Ile Pro Gly Asp  Asn Asn Gln Ile Arg  Ser Ile Val
    1385                 1390                 1395

Pro Ser  Tyr Phe Leu Glu Ile  Ser Lys Met Ile Ser  Phe Gln Arg
    1400                 1405                 1410

Glu Arg  Ala Phe Leu Arg Lys  Asn Thr Lys Leu Glu  Asn Asn Glu
    1415                 1420                 1425

Asn Gln  Asp Val Gln Trp Pro  Leu Ile Leu Glu Glu  Phe Gln Asp
    1430                 1435                 1440

Asn Ile  Ser Leu Asp His Lys  Ile Ile Ser Ser Glu  Leu Phe Ser
    1445                 1450                 1455

Glu Leu  Phe Phe Cys Asp Ile  Ser Gln Phe Gln His  Glu Phe Ile
    1460                 1465                 1470

Asp Lys  Ile Pro His Ser Trp  Thr Ile Leu Thr Ile  Gly Val Gly
    1475                 1480                 1485

Glu Ser  Lys Asn Asp Leu Tyr  Ile Thr Arg Leu Gln  Arg Gln Leu
    1490                 1495                 1500

Ser Pro  Leu Val Leu Arg Leu  Pro Leu Asn Arg Ser  Asn Ser Arg
    1505                 1510                 1515
```

```
Asp Ala  Asp Gln Asp Thr Leu  Thr Tyr Asp Asn Val  Phe Asn Glu
    1520                 1525                 1530

Leu Asn  Glu Ile Ile Phe Arg  Ser Asn Glu Thr Ala  Gln Ile Ala
    1535                 1540                 1545

Lys Asn  Ile Ser Thr Ser Ala  His Lys Val Val Trp  Trp Lys Glu
    1550                 1555                 1560

Arg Gln  Glu Leu Asp Ala Lys  Leu Lys Gln Leu Leu  Ile Asn Val
    1565                 1570                 1575

Glu His  Cys Trp Leu Gly Gly  Phe Lys Gly Ile Phe  Phe Gln Ser
    1580                 1585                 1590

Asn Ile  Asn Gln Gly Ser Phe  Val Arg Phe Lys Ile  Ser Val Asn
    1595                 1600                 1605

Lys Ile  Ile Ala Lys His Val  Phe Ser Arg Lys Ile  Phe Arg Lys
    1610                 1615                 1620

Asn Lys  Asn Val Val Thr Phe  Glu Ile Glu Ser Arg  Leu Leu Glu
    1625                 1630                 1635

Leu Phe  Val Lys Leu Asp Leu  Asn Asp Ser Lys Ile  Asp Glu Tyr
    1640                 1645                 1650

Leu Glu  Asp Leu Ile Tyr Phe  Ile Leu Asp Ile Phe  Gln Phe His
    1655                 1660                 1665

Gly Glu  Thr Val Ala Tyr Asp  Glu Ile Asp Ile Asp  Gln Met Val
    1670                 1675                 1680

Val Asp  Phe Gln Glu Ala Ile  Ser Asn Tyr Asn Lys  Glu Ser Ala
    1685                 1690                 1695

Val Leu  Leu Glu Lys Glu Gln  Gln His Leu Ile Leu  Val Leu Asp
    1700                 1705                 1710

Lys Ser  Ile Gln Ser Phe Pro  Trp Glu Ser Leu Pro  Cys Leu Arg
    1715                 1720                 1725

Lys Leu  Ser Ile Ser Arg Val  Pro Ser Leu Tyr Cys  Ile Tyr Asp
    1730                 1735                 1740

Arg Leu  Asn Ser Ala Lys Phe  Asp Ala Tyr Gln Lys  Val Asn Arg
    1745                 1750                 1755

Asn Asn  Gly Cys Tyr Ile Leu  Asn Pro Ser Cys Asp  Leu Ile Asn
    1760                 1765                 1770

Thr Gln  Asn Asn Phe Glu Ile  Leu Leu Lys Asn Leu  Glu Gly Trp
    1775                 1780                 1785

Glu Gly  Ile Val Gly Arg Glu  Pro Asp Glu Ser Glu  Leu Gln Ser
    1790                 1795                 1800

Phe Leu  Thr Ser Phe Glu Ile  Phe Leu Tyr Phe Gly  His Gly Gly
    1805                 1810                 1815

Gly Glu  Gln Tyr Ile Arg Lys  Asn Thr Val Lys Arg  Leu Pro Arg
    1820                 1825                 1830

Cys Ala  Val Ser Phe Leu Met  Gly Cys Ser Ser Gly  Leu Leu Lys
    1835                 1840                 1845

Asp Met  Gly Asp Phe Glu Pro  Ile Gly Met Ala Ile  Ser Tyr Leu
    1850                 1855                 1860

Leu Ala  Gly Cys Pro Ala Leu  Val Ala Asn Leu Trp  Asp Val Thr
    1865                 1870                 1875

Asp Lys  Asp Ile Asp Arg Phe  Ser Thr Ser Val Leu  Lys His Trp
    1880                 1885                 1890

Gly Leu  Ile Ser Asn Asp Leu  Lys Asn Gln Asp Gln  Thr Ala Pro
    1895                 1900                 1905

Lys Ile  Gly Asn Ser Leu Val  Asp Ala Ile Ala Phe  Ser Arg Asp
```

```
    1910                1915                1920

Gln Cys  Val Leu Lys Tyr Leu  Asn Gly Ala Ala Pro  Val Ile Tyr
    1925                1930                1935

Gly Ile  Pro Ile Tyr Leu Glu
    1940                1945


<210> SEQ ID NO 57
<211> LENGTH: 1063
<212> TYPE: PRT
<213> ORGANISM: Pneumocystis murina
<220> FEATURE:
<221> NAME/KEY: MISC_FEATURE
<222> LOCATION: (1)..(1063)
<223> OTHER INFORMATION: P. murina hypothetical protein PNEG_03454

<400> SEQUENCE: 57

Met Arg Phe Ser Ser Leu Leu Leu Leu Ser Phe Thr Phe Ile Thr Gln
1               5                   10                  15

Tyr Thr Lys Ser Asn Lys Leu Pro Gly Leu Asn Asn Thr Ala Lys Asp
            20                  25                  30

Ser Asn Ser Asn Tyr Asp Pro Ser His Ile Lys Val Ile Glu Thr Asp
        35                  40                  45

Phe Glu Lys Ser Leu Ile Asp Asp Ser Glu Tyr Arg Val Ile Lys Leu
    50                  55                  60

Lys Asn Gly Leu Glu Ala Ile Leu Val Ser Asp Pro His Ala Gln Val
65                  70                  75                  80

Ser Ser Thr Ala Leu Ser Ile Arg Ile Gly His Arg Tyr Asp Pro Lys
                85                  90                  95

Glu Phe Pro Gly Leu Ala His Leu Cys Glu His Leu Leu Phe Met Gly
            100                 105                 110

Thr Lys Lys Tyr Pro Gly Lys Asp Ser Tyr Asn Arg Phe Leu His Ser
        115                 120                 125

His Gly Gly Ala Tyr Asn Ala Tyr Thr Ser Leu Asp Arg Thr Ser Tyr
    130                 135                 140

Met Ser Asp Val Ser Pro Arg Tyr His Tyr Glu Gln Leu Asp Arg Met
145                 150                 155                 160

Ala Asn Phe Phe Ile Glu Pro Leu Phe Leu Glu Asp Ala Ile Glu Arg
                165                 170                 175

Glu Thr His Ser Val Asn Ser Glu Phe Glu Met Tyr Ser Thr Arg Tyr
            180                 185                 190

Val Arg Ala Arg Tyr Gln Ile Leu Cys His Met Phe Gly Asn Ser Ser
        195                 200                 205

Phe Phe Pro Arg Phe Thr Thr Gly Asn Arg Gln Thr Leu Phe Ser Gly
    210                 215                 220

Pro Arg Ala Arg Asn Leu Ser Thr Lys Gln Ala Leu His Asp Phe Phe
225                 230                 235                 240

Asn Lys Tyr Tyr Arg Pro His Asp Met Lys Leu Ala Ile Tyr Gly Asn
                245                 250                 255

Glu Ser Leu Asp Val Tyr Gln Glu Trp Ala Gln Ser Thr Phe Gly Gln
            260                 265                 270

Ile Pro Asp Arg Gly Val Arg Val Asp Lys Asp Ile Asn Pro Phe Ser
        275                 280                 285

Phe Leu Pro Lys His His Phe Trp Phe Gly Tyr Pro Asp Met Ser Pro
    290                 295                 300

Ala Leu Ser Leu Val Phe Phe Val Pro Ser Ser Gly Ile His Tyr Lys
305                 310                 315                 320
```

```
Ser Ile Pro Tyr His Tyr Leu Asp Tyr Val Phe Thr Tyr Pro Gly His
                325                 330                 335

Lys Ser Pro Leu Tyr Tyr Phe Ser Arg Leu Ser Leu Ala Ser Ser Ile
            340                 345                 350

Glu Leu Ser Leu Met Pro Tyr Ser Gln Ser Phe Asn Leu Leu Phe Val
        355                 360                 365

Asn Phe Val Leu Leu Pro Leu Gly Lys Ala Leu Tyr Thr Glu Val Ile
    370                 375                 380

Gly Glu Phe Phe Lys Cys Leu Gln Phe Phe Lys Asp Thr Gly Pro Asn
385                 390                 395                 400

Glu Glu Val Phe Glu Glu Ile Arg Lys Ala Gln Arg Asn Glu Phe Leu
                405                 410                 415

Tyr Ser Phe Lys Gly Thr Pro Phe Asn Tyr Ala Glu Asp Leu Ser Val
            420                 425                 430

Thr Leu Leu Ser Glu Ser Phe Pro Arg Lys His Val Leu Asn Arg Phe
        435                 440                 445

Tyr Leu Lys Glu Tyr Asp Lys Glu Glu Ile Leu Asp Phe Phe Ser Tyr
    450                 455                 460

Leu Asn Pro His Asn Phe Ile Ser Phe Val Asn Met Asn Lys Lys Phe
465                 470                 475                 480

Asn Glu Thr Glu Pro Phe Tyr Gly Ile Pro Tyr Leu Lys Glu His Tyr
                485                 490                 495

Ser Glu Lys Phe Ile Glu Ser Leu Lys Asn Pro Leu Pro Thr Lys Leu
            500                 505                 510

Gln Tyr Pro Pro Lys Asn Val Tyr Ile Ser Thr Asn Ile Gln Ile Thr
        515                 520                 525

Met Glu Lys Leu Asn Glu Thr Leu Ser Lys Pro Asp Ile Leu Arg Ala
    530                 535                 540

Ser Pro Ile Thr Thr Leu Trp Tyr Lys His Gly Ser Phe Phe Tyr Cys
545                 550                 555                 560

Pro Tyr Gly Ile Ile Arg Val Leu Leu Arg Ser Gln Phe Ile Ser Ser
                565                 570                 575

Ser Pro Thr Asn Leu Tyr Lys Leu Arg Phe Leu Gln Val His Leu Tyr
            580                 585                 590

Thr Ser Leu Ser Tyr Ser Ser Phe Tyr Thr Thr Met Ala Gly Leu Asp
        595                 600                 605

Phe Ser Ile Thr Thr Val Thr Gln Gly Val Leu Ile Tyr Ile Tyr Gly
    610                 615                 620

Phe Ser Asp Lys Ile Met Glu Ile Phe Ser Lys Ile Ile Ala Leu Phe
625                 630                 635                 640

Lys Asp Leu Ser Ile Thr Ala Gln Glu Phe Gly Arg Leu Lys Ser Val
                645                 650                 655

Ile Phe Thr Ser Val Ala His Arg Ser Ile Gly Glu Pro Gly Thr Ile
            660                 665                 670

Val Asp Ser Glu Ile Asp Asp Ile Leu Phe Ser Glu Lys Thr Pro Leu
        675                 680                 685

Val Asn Leu Val Leu Leu Ser Glu Gln Phe Phe His Pro Asp Ile Ala
    690                 695                 700

Ala Phe Phe Tyr Asp Phe Leu Ser Asn Leu His Ile Asp Val Leu Ile
705                 710                 715                 720

Thr Gly Asn Val Pro Pro Gln Asp Ala Leu His Val Phe Tyr Met Met
                725                 730                 735
```

-continued

```
Glu Ala Val Phe His Ala His Pro Leu Thr Pro Ser Gln Tyr Ile Asn
            740                 745                 750

Asn Arg Ala Ile Asp Leu Asp Ser Gly Ser Asp Tyr Tyr Tyr Thr Gln
        755                 760                 765

Lys Met Tyr Asn Lys Glu Arg Lys Ser Ala Leu Leu Val Tyr Leu Gln
    770                 775                 780

Val Ala Glu Ser Asn Asn Met Lys Arg Val Gln Met Leu Tyr Leu Leu
785                 790                 795                 800

Phe Thr Ile Leu Arg Gly Phe Phe Phe Ser Gln Met Arg Thr Lys Glu
                805                 810                 815

Gln Leu Gly Tyr Tyr Val Thr Ser Asn Val Arg Ile Ser Lys Thr Ile
            820                 825                 830

Leu Gly Ile Ser Phe Leu Ile Gln Ser Glu Arg Gln Pro His Val Leu
        835                 840                 845

His Ser Arg Phe Asp Ala Phe Phe Asp Asn Ser Leu Asp Ile Leu Leu
    850                 855                 860

Asn Ile Thr Pro Lys Glu Phe Asp Tyr Tyr Leu Asp Ala Tyr Asn Val
865                 870                 875                 880

Met Phe Lys Arg Thr Pro Ile Glu Ile Ser Ser Glu Thr Ser Arg Ser
                885                 890                 895

Trp Ile Ser Ile Ile Glu Gly Thr Tyr Val Phe Glu Tyr Asp Lys Pro
            900                 905                 910

Asp Asp Pro Ile Glu Ser Ile Lys Leu Gln Asp Ile Ile Glu Leu Leu
        915                 920                 925

Lys Glu Leu Arg Ala Ser Lys Lys Arg Ile Ser Tyr Tyr Ala Tyr Ser
    930                 935                 940

Gln Ile Asn Ser Asp Ile Tyr Asn Val Phe Asp Met Pro Ile Ser Lys
945                 950                 955                 960

Leu Ser Lys Tyr Leu Ala Ser Lys Gly Glu Lys Ile Ser Glu Glu Glu
                965                 970                 975

Leu His Glu Tyr Val Leu Leu Ser His Asn Val Ser Ser Phe Arg Ala
            980                 985                 990

Asn Leu Phe Gly His Leu Ile Lys  Asn Lys Asp Asn Asp  Thr Ala Glu
        995                 1000                1005

Ser Phe  Leu Asn Glu Thr Phe  Gln Phe Leu Gln His  Leu Tyr Asn
    1010                1015                1020

Asn Glu  Lys Lys Glu Ile Leu  Lys Ser Tyr Thr Leu  Ile Glu Asp
    1025                1030                1035

Ile Thr  Tyr Phe Lys Ala Asn  Met Ser Leu Ser Ser  Gly Pro Ile
    1040                1045                1050

Arg Lys  Ser Leu Trp Ser Lys  Tyr Tyr Arg
    1055                1060


<210> SEQ ID NO 58
<211> LENGTH: 3272
<212> TYPE: DNA
<213> ORGANISM: Artificial sequence
<220> FEATURE:
<223> OTHER INFORMATION: Codon-optimized sequence

<400> SEQUENCE: 58

gtcgacatgt actccatgca gctcgcttct tgcgttacct tgactctggt gctgctcgtc      60

aacagcatgc ggttctcctc actcctcctc ctctccttca ctttcatcac acagtacact     120

aaatcaaaca aactccctgg actcaacaac actgccaagg attcaaacag caattatgac     180
```

-continued

```
cctagccaca tcaaagtgat tgaaaccgat ttcgagaagt ccctgatcga cgattctgaa    240
tacagggtca ttaagctcaa aaacggcctg gaggccatcc tcgtgtcaga tccacacgcc    300
caggtcagct ccactgctct gagcatcaga attggccatc ggtacgaccc taaggaattc    360
ccaggactgg ctcacctctg cgagcatctg ctctttatgg gcaccaagaa atatcccgga    420
aaggactcct acaacaggtt cctgcactct catggcggag catataatgc ctacacttct    480
ctggatagaa cctcctacat gtctgacgtc agtccccgct atcactacga gcagctggat    540
cgaatggcta acttctttat cgagcctctg ttcctcgaag acgcaattga acgggagaca    600
cactcagtga atagcgaatt tgagatgtat tccactcgct acgtcagggc cagataccag    660
atcctgtgtc atatgtttgg caactctagt ttctttcccc gattcaccac agggaatagg    720
cagaccctgt ttagtggtcc tcgggcacgc aacctctcaa caaagcaggc cctgcacgat    780
ttctttaaca agtactatag accacatgac atgaagctcg ccatctatgg aaacgagagc    840
ctggatgtgt accaggaatg ggctcagtcc accttcgggc agatccccga ccgaggtgtg    900
agggtggaca aggatattaa tcccttcagc ttcctgccca aacaccattt ttggttcggc    960
tatcccgata tgtctcctgc cctgagtctc gtgttctttg tcccttcaag cggaatccac   1020
tacaagagca ttccatatca ttacctggac tatgtgttca catacccctgg ccacaaatcc   1080
ccactgtact atttttcccg gctgtctctc gcttcctcta tcgagctgtc tctcatgcct   1140
tattcccagt ctttcaacct gctctttgtg aatttcgtcc tgctcccact ggggaaggca   1200
ctctacactg aagtgatcgg cgagttcttt aagtgcctgc agttctttaa agataccggg   1260
cccaacgagg aagtcttcga ggaaattcgc aaggctcagc gaaacgagtt tctgtattcc   1320
ttcaaaggta ctcccttcaa ctacgcagaa gacctgtctg tgaccctgct cagtgagtca   1380
ttccccagaa agcacgtcct caatcggttt tatctgaagg agtacgataa agaggaaatc   1440
ctcgacttct tttcctatct gaaccctcat aacttcatct ctttcgtgaa catgaataag   1500
aagttcaacg aaaccgagcc cttctatggc atcccttacc tgaaggaaca ctactctgag   1560
aaattcattg aaagtctgaa gaatcctctc ccaaccaaac tgcagtatcc ccctaagaac   1620
gtgtacatct ccacaaatat ccagattact atggagaaac tcaacgaaac actgagcaag   1680
ccagacatcc tcagggcctc cccattact accctgtggt acaagcacgg cagtttcttt   1740
tattgtcctt acggaatcat tagggtgctg ctcagaagcc agttcatcag ttcaagccca   1800
accaacctgt ataagctcag atttctgcag gtgcatctct acacaagcct gtcctattcc   1860
tctttctaca caactatggc aggactggat tttagcatca ccacagtgac acagggcgtc   1920
ctgatctata tctacggatt ctctgataag atcatggaaa tttttagtaa gatcatcgcc   1980
ctcttcaagg acctgtccat cactgctcag gagtttgggc gcctgaagag tgtgattttc   2040
acttcagtcg ctcaccgaag catcggggag cctggtacca ttgtggactc agaaatcgac   2100
gatattctgt tcagcgagaa gaccccactc gtgaacctgg tcctgctcag cgagcagttc   2160
tttcaccccg atatcgccgc tttcttttac gactttctct ccaacctgca tatcgatgtg   2220
ctgattacag ggaatgtccc accccaggac gcactgcacg tgttttatat gatggaggct   2280
gtcttccacg cacatcccct gacacctagc cagtacatca acaatcgggc cattgacctg   2340
gattctggta gtgactacta ttacactcag aagatgtata acaaggaacg gaaatctgct   2400
ctgctcgtgt acctgcaggt cgcagagagt aacaatatga agcgcgtgca gatgctctac   2460
ctgctcttca caatcctgag ggggttcttt ttctcccaga tgagaactaa ggagcagctg   2520
ggttattacg tgacttccaa cgtccgcatc tctaaaacca tcctcgggat tagtttcctg   2580
```

```
attcagtcag agcggcagcc acacgtgctg catagtcgct ttgacgcctt tttcgataac   2640

tcactggaca tcctgctcaa tattaccccc aaggagttcg attattacct ggacgcttac   2700

aacgtgatgt ttaaaagaac acctatcgag attagttcag aaacttcacg gagctggatc   2760

tctatcattg agggaacata tgtgttcgaa tacgataaac cagacgatcc catcgagagc   2820

attaagctgc aggacatcat tgagctgctc aaagaactgc gggcaagcaa gaaacgcatc   2880

tcctattacg cctattcaca gatcaacagc gatatctaca atgtgttcga catgccaatc   2940

agtaagctct caaaatatct ggcctcaaag ggcgaaaaaa ttagcgagga agagctgcac   3000

gagtacgtgc tgctctccca taacgtcagc tcctttagag caaatctctt cggacacctg   3060

atcaagaaca aagacaatga taccgccgag tctttcctga acgaaacatt tcagttcctc   3120

cagcatctgt acaacaatga aaagaaagag atcctcaagt cctataccct gatcgaggac   3180

atcacatact tcaaggctaa catgtctctg tctagtggcc ccatccgaaa gagcctgtgg   3240

tccaaatatt acaggtgagg atccgcggcc gc                                 3272
```

<210> SEQ ID NO 59
<211> LENGTH: 1200
<212> TYPE: PRT
<213> ORGANISM: Pneumocystis murina
<220> FEATURE:
<221> NAME/KEY: MISC_FEATURE
<222> LOCATION: (1)..(1200)
<223> OTHER INFORMATION: P. murina major surface glycoprotein PNEG_03599

<400> SEQUENCE: 59

```
Met Arg Ser Thr Ser Phe Thr Phe Leu Val Tyr Leu Gly Cys Ile Leu
1               5                   10                  15

Val Ala Ala Leu Glu Asn Ala Ile Ser Asn Ile Asn Lys Gln Glu Leu
            20                  25                  30

Gln Val Ile Glu Leu Phe Glu Asn Glu Lys Leu Leu Gly Ser Glu Lys
        35                  40                  45

Ile Arg Gly Ser Lys Gly Ile Trp Asn Pro Arg Ile Asn Lys Asp Ser
    50                  55                  60

Tyr Met Asp Tyr Phe Glu Asn His Pro Gly Val Asp Tyr Phe Arg Lys
65                  70                  75                  80

Asp Asp Tyr Glu Asn Phe Phe Pro Glu Gly Tyr Pro Gln Asp Asn Gln
                85                  90                  95

Trp Val Glu Glu Ile Thr Gln Lys Arg Ala Val Thr Ala Gln Leu Val
            100                 105                 110

Lys Arg Gln Ala Pro Gly Gln Ala Ala Gly Asn Asp Glu Ile Lys Glu
        115                 120                 125

Glu Gln Val Leu Gly Leu Ile Val Lys Asn Glu Tyr Lys Asn Asp Asp
    130                 135                 140

Asn Cys Lys Lys Lys Leu Lys Glu Tyr Cys Glu Glu Leu Glu Lys Ile
145                 150                 155                 160

Asp Gly Lys Leu Glu Asn Val Asp Ser Lys Val Lys Gly Leu Cys Asn
                165                 170                 175

Asp Lys Glu Lys Lys Cys Gln Asp Leu Lys Gln Lys Ile Gln Asn Glu
            180                 185                 190

Leu Asn Asn Phe Lys Thr Glu Leu Glu Asn Ala Leu Lys Asn Leu Thr
        195                 200                 205

Asp Glu Lys Cys Arg Lys Cys Glu Glu Lys Cys Val Leu Leu Glu Glu
    210                 215                 220
```

```
Ala Asp Pro Thr Asn Leu Lys Asp Asn Cys Val Lys Leu Arg Asp Arg
225                 230                 235                 240

Cys Tyr Lys Gln Arg Arg His Gly Val Ala Lys Glu Ile Leu Leu Arg
                245                 250                 255

Ala Leu Asn Gly Lys Val Thr Asp Ile Asn Glu Cys Glu Gly Lys Ile
            260                 265                 270

Lys Gly Val Cys Gln Glu Leu Ser Gly Tyr Ser Asp Glu Leu Met Phe
        275                 280                 285

Ser Cys Phe Asn Ala Tyr Thr Thr Cys Glu Tyr Leu Gly Gly Asn His
    290                 295                 300

Thr Asp Asn Cys Lys Pro Leu Glu Thr Glu Leu Lys Asp Asn Glu Leu
305                 310                 315                 320

Met Glu Lys Cys Gln Glu Tyr Leu Lys Lys Cys Tyr Phe Tyr Gly Ser
                325                 330                 335

Ser Cys Lys Asn Ala Lys Cys Asp Asn Ile Glu Lys Lys Cys Glu Glu
            340                 345                 350

Lys Gly Ile Arg Tyr Arg Ser Pro Lys Leu Asp Phe Ser Pro Ile Leu
        355                 360                 365

His Lys Pro Lys Leu Met Glu Arg Ile Glu Met Glu Asn Leu Tyr Lys
    370                 375                 380

Glu Glu Glu Ala Lys Gly Ile Ile Ile Gly Arg Pro Lys Glu Lys Ser
385                 390                 395                 400

Phe Glu Thr Val Leu Leu Leu Leu Ser Glu Gly Lys Asn Asn Lys Leu
                405                 410                 415

Glu Glu Lys Cys Lys Asn Val Ile Gly Asn Cys Glu Ala Phe Lys Tyr
            420                 425                 430

Leu Asp Ile Met Leu Glu Asn Ser Cys Arg Glu Ala Ser Lys Lys Lys
        435                 440                 445

Glu Glu Lys Cys Lys Glu Ile Pro Asn Val Lys Lys Lys Cys Leu Asn
    450                 455                 460

Phe Lys Ile Lys Leu Tyr Thr Lys Gly Met Ser Thr Glu Phe Glu Glu
465                 470                 475                 480

Asn Lys Asp Ser Gly Leu Phe Ser Trp Arg Glu Leu Gln Lys Ser Leu
                485                 490                 495

Ser Arg Glu Asp Cys Ile Glu Leu Glu Ser Glu Cys Phe Tyr Leu Glu
            500                 505                 510

Asn Val Cys Thr Asn Lys Ile Glu Asn Ala Cys Lys Asn Val Arg Ala
        515                 520                 525

Thr Cys Tyr Lys Lys Gly Gln Asp Arg Ala Leu Gly Lys Tyr Phe Glu
    530                 535                 540

Ser Gly Leu Lys Asn Leu Arg Tyr Leu Asn Phe Thr Gly Lys Lys Ser
545                 550                 555                 560

Glu Cys Gln Lys Leu Val Arg Asp Lys Cys Lys Lys Val Asn Gly Asp
                565                 570                 575

Arg Lys Tyr Met Lys Lys Cys Leu His Pro Glu Glu Leu Cys Leu Glu
            580                 585                 590

Leu Leu Asp Asp Ile Ser Val Gln Ser Lys Glu Leu Gly Glu Thr Leu
        595                 600                 605

Asp Asn Val Arg Asp Leu Pro Gly Lys Lys Asp Cys Val Glu Leu Lys
    610                 615                 620

Lys Arg Cys Asp Tyr Leu Arg Asn Asn Ser Arg Leu Ser Asp Lys Lys
625                 630                 635                 640

Cys Ala Thr Leu Asp Arg Gln Cys Arg Tyr Leu Gly Val Met Glu Glu
```

```
                645                 650                 655

Met Arg Lys Arg Phe Leu Lys Arg Lys Asp Asp Ser Leu Lys Thr Ser
            660                 665                 670

Lys Asn Cys Ile Asp Ala Leu Lys Glu Glu Cys Lys Gly Leu Ser Lys
        675                 680                 685

Glu Glu Lys Asn Pro Phe Ser Ile Leu Cys Ala Leu Pro Glu Glu Thr
    690                 695                 700

Cys Glu Phe Met Ile Ala Lys Thr Asn Ile Glu Cys Phe Thr Phe Lys
705                 710                 715                 720

Asp Arg Thr Glu Asn Ile Leu Lys Asn Asn Asn Lys Asn Lys Asn Leu
                725                 730                 735

Val Lys Arg Leu Cys Leu Ser Trp Ser Leu Tyr Ser Asp Glu Tyr Met
            740                 745                 750

Glu Ile Cys Ser Lys Ile Leu Glu Glu Lys Thr Asn Gly Lys Glu Ser
        755                 760                 765

Leu Gln Glu Leu Lys Lys Asn Cys Asp Pro Phe Trp Lys Glu Leu Glu
    770                 775                 780

Leu Glu Lys Asp Leu Met His Glu Leu Lys Gly Asn Leu Gly Lys Asp
785                 790                 795                 800

Asp Glu Cys Lys Glu Ala Leu Lys Lys His Cys Thr Glu Gln Lys Asn
                805                 810                 815

Gln Thr Asn Gln Lys Phe Asn Ser Phe Cys Asn Thr Asp Lys Asp Asn
            820                 825                 830

Gly Val Glu Glu Lys Val Cys Lys Lys Leu Val Glu Glu Val Lys Arg
        835                 840                 845

Lys Cys Pro Thr Leu Lys Asn Glu Leu Val Lys Glu Lys Asp Glu Leu
    850                 855                 860

Lys Glu Lys Lys Asp Glu Tyr Glu Lys Val Lys Gln Glu Ser Glu Lys
865                 870                 875                 880

Phe Ala Lys Glu Ala Lys Leu Leu Leu Ser Arg Leu Glu Gln Asp Gly
                885                 890                 895

Gln Gly Gly Gly Ser Lys Val Gln Asp Asn Ser Ala Pro Lys Pro Val
            900                 905                 910

Asp Pro Ala Ala Pro Val Ala Pro Val Ala Pro Val Ala Pro Val Ala
        915                 920                 925

Pro Gly Thr Pro Gly Gly Thr Pro Gly Ala Pro Ser Thr Pro Gly Thr
    930                 935                 940

Pro Gly Ala Pro Ser Thr Pro Gly Ala Pro Gly Ala Pro Ser Thr Pro
945                 950                 955                 960

Ser Thr Pro Pro Ala Pro Ala Gly Pro Ala Gly Pro Ser Gly Gly Thr
                965                 970                 975

Pro Ala Gly Pro Pro Ala Gly Pro Pro Ala Gly Pro Pro Ala Pro Gly
            980                 985                 990

Gly Ser Thr Pro Ser Gly Thr Thr  Asn Thr Ser Asn Val  Ile Leu Val
        995                 1000                1005

Arg Arg  Thr Phe Val Ser Gly  Glu Val Ser Glu Ala  Glu Lys Lys
    1010                1015                1020

Ala Phe  Val Ala Thr Ala Arg  Ala Leu Glu Leu Tyr  Leu Gly Leu
    1025                1030                1035

Lys Glu  Lys Cys Lys Thr Leu  Lys Gly Asp Cys Gly  Tyr Arg Lys
    1040                1045                1050

Asp Cys  Pro Asp Cys Asp Thr  Val Cys Lys Glu Ile  Asp Lys Leu
    1055                1060                1065
```

```
Cys Glu  Glu Ile Glu Gly Leu  Lys Ile Ile Ser His  Pro Thr Ala
    1070                 1075                 1080

Thr Leu  Thr Thr Ile Gln Ala  Thr Thr Lys Thr Ala  Thr Thr Thr
    1085                 1090                 1095

Thr Thr  Thr Thr Met Thr Thr  Thr Ala Thr Thr Thr  Ala Thr Ala
    1100                 1105                 1110

Thr Glu  Thr Thr Ala Thr Thr  Thr Thr Glu Ser Ile  Asp Gly Glu
    1115                 1120                 1125

Lys Val  Thr Glu Gln Cys Thr  Leu Val Arg Thr Thr  Asp Thr Trp
    1130                 1135                 1140

Val Thr  Ser Thr Ser Leu His  Thr Ser Thr Met Thr  Ser Thr Ser
    1145                 1150                 1155

Thr Val  Thr Ser Thr Val Thr  Leu Thr Ser Met Arg  Lys Cys Lys
    1160                 1165                 1170

Pro Thr  Arg Cys Thr Ser Asp  Ser Ser Lys Glu Thr  Glu Thr Gln
    1175                 1180                 1185

Lys Glu  Glu Lys Glu Glu Glu  Glu Val Lys Ser Asn
    1190                 1195                 1200


<210> SEQ ID NO 60
<211> LENGTH: 643
<212> TYPE: PRT
<213> ORGANISM: Pneumocystis murina
<220> FEATURE:
<221> NAME/KEY: MISC_FEATURE
<222> LOCATION: (1)..(643)
<223> OTHER INFORMATION: P. murina major surface glycoprotein PNEG_00001

<400> SEQUENCE: 60

Met Tyr Gly Tyr Phe Glu Arg Ile Ile Ser Arg Phe Arg Phe Asp Ser
1               5                   10                  15

Pro Ser His Met Leu Leu Arg Asp Lys Arg Trp Val Glu Glu Val Ala
            20                  25                  30

Gln Lys Glu Ala Ala Met Ala Gln Pro Val Lys Arg Gln Ala Ala Gly
        35                  40                  45

Gln Ala Ala Gly Asn Asp Glu Ile Lys Glu Glu Gln Val Leu Gly Leu
    50                  55                  60

Ile Val Lys Lys Glu Tyr Asn Asp Asp Ala Lys Cys Lys Lys Lys Leu
65                  70                  75                  80

Glu Glu Tyr Cys Ala Glu Leu Lys Lys Ile Asp Gly Glu Leu Lys Asn
                85                  90                  95

Val Asp Val Lys Val Lys Gly Leu Cys Glu Asn Gly Lys Gln Glu Glu
            100                 105                 110

Lys Cys Lys Asn Leu Lys Asn Lys Val Lys Lys Glu Leu Asp Asp Phe
        115                 120                 125

Lys Thr Glu Val Glu Glu Ala Leu Lys Asn Leu Thr Asp Glu Lys Cys
    130                 135                 140

Lys Lys Cys Glu Glu Lys Cys Val Leu Leu Glu Glu Ala Asp Pro Thr
145                 150                 155                 160

Asn Leu Glu Glu Lys Cys Val Lys Leu Arg Asp Arg Cys Tyr Gly Gln
                165                 170                 175

Arg Arg Arg Glu Val Thr Lys Glu Ile Leu Leu Arg Ala Leu Lys Gly
            180                 185                 190

Lys Val Asn Asp Thr Asn Glu Cys Lys Lys Lys Met Lys Glu Ile Cys
        195                 200                 205
```

```
Gln Gly Leu Ser Glu Tyr Ser Asp Glu Leu Val Phe Ser Cys Phe Asn
    210                 215                 220

Ser Asn Lys Thr Cys Glu Tyr Leu Gly Lys Asn His Gly Asp Asn Cys
225                 230                 235                 240

Lys Pro Leu Glu Lys Glu Leu Glu Asp Lys Glu Leu Val Glu Lys Cys
                245                 250                 255

Gln Glu Tyr Leu Glu Lys Cys Tyr Phe Tyr Gly Ser Ser Cys Ser Asn
            260                 265                 270

Ser Lys Cys Lys Glu Ser Lys Glu Lys Cys Lys Gly Lys Gly Ile Val
        275                 280                 285

Tyr Glu Gly Pro Lys Leu Asp Phe Ser Pro Val Gly Glu Lys Pro Arg
    290                 295                 300

Phe Pro Glu Lys Ile Glu Val Glu Asn Leu Tyr Lys Lys Glu Glu Ala
305                 310                 315                 320

Lys Gly Ile Ile Val Gly Lys Pro Lys Tyr Lys Thr Leu Gln Asp Leu
                325                 330                 335

Ile Leu Leu Leu Ile Lys Gly Arg Thr Glu Lys Asp Asn Lys Glu Lys
            340                 345                 350

Cys Lys Glu Ala Leu Glu Gly Cys Glu Phe Phe Lys His Leu Asp Tyr
        355                 360                 365

Glu Leu Glu Glu Leu Cys Glu Asp Lys Asp Lys Asp Lys Glu Asn Lys
    370                 375                 380

Cys Lys Glu Leu Val Glu Val Glu Asp Lys Cys Thr Asn Leu Lys Leu
385                 390                 395                 400

Glu Leu Tyr Leu Lys Gly Leu Ser Thr Glu Phe Glu Lys Asp Lys Glu
                405                 410                 415

Ser Glu Tyr Phe Ser Trp Glu Gln Val Ser Lys Leu Val Ser Arg Glu
            420                 425                 430

Asp Cys Arg Lys Phe Glu Ser Glu Cys Phe His Leu Glu Ser Val Cys
        435                 440                 445

Thr Asn Lys Ile Glu Lys Ala Cys Glu Asn Val Arg Val Ala Cys Tyr
    450                 455                 460

Lys Lys Gly Gln Asp Arg Met Leu Asn Arg Tyr Phe Gln Glu Gly Leu
465                 470                 475                 480

Lys Gly Leu Ile Gly Asn Leu Gly Leu Ala Asp Glu Asn Leu Lys Glu
                485                 490                 495

Cys Gln Lys Ser Val Val Gly Asn Tyr Thr Lys Leu Lys Lys Asp Arg
            500                 505                 510

Arg Tyr Phe Ala Lys Cys His Arg Pro Thr Glu Leu Cys Tyr Glu Leu
        515                 520                 525

Leu Asp Asp Val Ile Leu Gln Ser Glu Glu Leu Glu Val Val Leu Asn
    530                 535                 540

Leu Arg Arg Asp Phe Pro Arg Lys Glu Asp Cys Val Glu Leu Lys Lys
545                 550                 555                 560

Lys Cys Glu Asp Leu Glu Ser Asp Ser Tyr Leu Asn His Glu Lys Cys
                565                 570                 575

Asp Thr Leu Asn Arg Arg Cys Glu Tyr Leu Lys Val Thr Glu Glu Leu
            580                 585                 590

Arg Lys Arg Leu Leu Lys Arg Gly Asp Asp Ala Leu Arg Thr Gln Gly
        595                 600                 605

Asn Cys Thr Ala Val Leu Lys Lys Glu Cys Glu Glu Leu Ser Lys Arg
    610                 615                 620

Gly Lys Asp Glu Phe Ser Val Ser Cys Ala Leu Arg Glu Glu Thr Cys
```

625 630 635 640

Ser Phe Met

<210> SEQ ID NO 61
<211> LENGTH: 144
<212> TYPE: PRT
<213> ORGANISM: Pneumocystis murina
<220> FEATURE:
<221> NAME/KEY: MISC_FEATURE
<222> LOCATION: (1)..(144)
<223> OTHER INFORMATION: P. murina hypothetical protein PNEG_00053

<400> SEQUENCE: 61

Met Gln Ile Phe Val Lys Thr Leu Thr Gly Lys Thr Ile Thr Leu Glu
1 5 10 15

Val Glu Ser Ser Asp Thr Ile Asp Asn Val Lys Ser Lys Ile Gln Asp
20 25 30

Lys Glu Gly Ile Pro Pro Asp Gln Gln Arg Leu Ile Phe Ala Gly Lys
35 40 45

Gln Leu Glu Asp Gly Arg Thr Leu Ser Asp Tyr Asn Ile Gln Lys Glu
50 55 60

Ser Thr Leu His Leu Val Leu Arg Leu Arg Gly Gly Ala Ile Gln Arg
65 70 75 80

Cys Thr Met Lys Gln Cys Ser Ala Ser Ala Val Arg Ile Val Gly Asp
85 90 95

Cys Asn Phe Cys Asp Gly His Phe Cys Gly Arg His Arg Gln Leu Glu
100 105 110

Asn His Ala Cys Thr Gly Leu Gln Glu Cys Arg Gln Gln Ser His Glu
115 120 125

Arg Asn Arg Thr Lys Leu Gln Lys Glu Gln Cys Val Ala Ser Lys Val
130 135 140

<210> SEQ ID NO 62
<211> LENGTH: 1098
<212> TYPE: PRT
<213> ORGANISM: Pneumocystis murina
<220> FEATURE:
<221> NAME/KEY: MISC_FEATURE
<222> LOCATION: (1)..(1098)
<223> OTHER INFORMATION: P. murina major surface glycoprotein PNEG_00563

<400> SEQUENCE: 62

Met Ile Asn Lys Ile Ile Leu Ile Ala Ile Leu Asn Leu Ile Ala Leu
1 5 10 15

Thr Tyr Gly Asn Gln Ser Val Asp Leu Ser Ile Arg Asn Ser Gln Thr
20 25 30

Asn Ala Leu Asn Pro Ser Phe Lys Ser Phe Ile Glu Glu Asp Ile Tyr
35 40 45

Gly Phe Ile Leu Lys Glu Asn Tyr Asp Asp Glu Asn Lys Cys Lys Ala
50 55 60

Lys Leu Glu Glu Tyr Cys Lys Glu Leu Lys Asp Ile Asp Pro Glu Leu
65 70 75 80

Asn Lys Val Asn Ser Asn Val Lys Glu Ile Cys Asn Asn Asn Asn Lys
85 90 95

Glu Gln Lys Cys Lys Asp Leu Lys Leu Asn Ile Lys Glu Asn Leu Asp
100 105 110

Lys Ile Ser Asn Glu Leu Tyr Val Ile Leu Gln Lys Ser Leu Thr Tyr
115 120 125

```
Glu Asp Phe Asp Lys Tyr Leu Pro Arg Cys Leu Phe Leu His Asn Leu
    130                 135                 140

Thr Lys Asn Ile Leu Glu Tyr Cys Tyr Leu Leu Lys Tyr Asn Tyr Tyr
145                 150                 155                 160

Ile Arg Lys His Leu Lys Leu Thr Leu Glu Leu Ile Leu His Ala Val
                165                 170                 175

Gly Asn Ser Ile Ala Asn Tyr Asp Asp Phe Lys Glu Lys Met Lys Glu
            180                 185                 190

Ile Cys Pro Ile Leu Ile Gln Gln Gly Thr Asn Phe Ile Ser Glu Cys
        195                 200                 205

Phe Lys Ile Lys Glu Ser Phe Glu Glu Leu Asn Lys Tyr Ile Asn Tyr
    210                 215                 220

Phe Cys Asn Ser Leu Asn Ile Asn Leu Asn Asp Asn Glu Leu Gln Glu
225                 230                 235                 240

Gln Cys His Lys Lys Leu Lys Ser Cys Tyr Phe Leu Lys Asn Lys Cys
                245                 250                 255

Lys Lys Lys Cys Asn Glu Leu Lys Val Leu Cys Glu Lys Lys Asn Ile
            260                 265                 270

Thr Tyr Lys Pro Pro Gly Lys Asp Phe Asn Pro Ile Glu Pro Glu Thr
        275                 280                 285

Thr Leu Leu Lys Ile Glu Leu Glu Asp Phe Tyr Lys Lys Met Lys Asp
    290                 295                 300

Glu Gly Ile Tyr Ile Gly Asn Val Glu Ala Thr Leu Asp Asn Ile Leu
305                 310                 315                 320

Ile Tyr Leu Ser Ser Thr Thr Thr Gly Phe Ser Gly Asn Lys Cys Arg
                325                 330                 335

Ile Val Leu Ser Gly Asn Cys Asp Phe Phe Lys Phe Leu Ser Pro Glu
            340                 345                 350

Phe Lys Glu Leu Cys Gln Asn Ser Arg Arg Gln Lys Cys Arg Asp Ile
        355                 360                 365

Ser Lys Ile Thr Asn Lys Cys Arg Lys Phe Lys Ile Met Leu Tyr Leu
    370                 375                 380

Ala Gly Phe Ser Thr His Phe Gln Asp His Ile Ile Gly Gln Asp Ile
385                 390                 395                 400

Leu Trp Asp Lys Leu Ser Thr Ser Phe Ser Asp Lys Glu Leu Leu Lys
                405                 410                 415

Phe Asp Thr Asn Cys Phe Tyr Ile Gln Arg Ser Cys Arg Asn Asn Leu
            420                 425                 430

Leu Glu Val Cys Lys Asn Val Lys Ile Ala Asn Asn Lys Lys Gln Gln
        435                 440                 445

Arg Gln Leu Phe Ile Lys Leu Ile Glu Gly Lys Leu Val Glu Glu Gln
    450                 455                 460

Tyr Asn Leu Lys Ser Lys Asp Asp Lys Leu Lys Ile Cys Gln Lys Val
465                 470                 475                 480

Val Met Glu Lys Cys Val Thr Leu Val Asn Ser Asn Ile Glu Asn Phe
                485                 490                 495

Leu Lys Cys Leu Arg Pro Lys Glu Ile Cys Leu Glu Leu Glu Glu Ile
            500                 505                 510

Ile Phe Thr Arg Ser Lys Asp Leu Glu Gln Ala Leu Asp Gln Ala Arg
        515                 520                 525

Asp Phe Pro Lys Glu Glu Asp Cys Val Glu Leu Lys Lys Gly Cys Glu
    530                 535                 540

Ser Ile Ala Gly Asp Leu Gly Ser Asn Asn Ala Lys Cys Val Thr Leu
```

```
545                 550                 555                 560

Lys Glu Arg Cys Lys Tyr Leu Lys Val Thr Lys Glu Leu Lys Tyr Val
                565                 570                 575

Phe Leu Lys Asp Lys Ser Asp Ser Leu Ala Asn Ile Gln Asn Cys Met
            580                 585                 590

Lys Ala Leu Lys Glu Lys Cys Asp Arg Leu Phe Lys Arg Gly Thr Asn
        595                 600                 605

Thr Phe Asp Ile Ser Cys Ala Leu Pro Glu Glu Thr Cys Lys Phe Met
    610                 615                 620

Val Ser Glu Val Lys Asn His Cys Ser Thr Phe Lys Asn Asn Ile Glu
625                 630                 635                 640

Lys His Asp Ile Val Asn Lys Ser Lys Asn Gly Asn Glu Thr Leu Val
                645                 650                 655

Glu Glu Ile Cys Ile Leu Trp Asp Pro Tyr Cys Asp Glu Leu Met Glu
            660                 665                 670

Asn Cys Pro Asp Lys Leu Lys Lys Gly Asp Asn Gly Asn Glu Lys Gly
        675                 680                 685

Val Cys Leu Gln Leu Lys Glu Asn Cys Arg Pro Phe Phe Glu Lys Leu
    690                 695                 700

Lys Leu Glu Asn Glu Leu Met His Glu Leu Lys Gly Ser Leu Gly Asp
705                 710                 715                 720

Lys Thr Lys Cys Lys Lys Thr Leu Gly Lys His Cys Thr Glu Lys Lys
                725                 730                 735

Asn Gln Ala Asn Gln Lys Phe Asn Ser Phe Cys Asn Thr Asp Lys Asn
            740                 745                 750

Lys Asn Val Glu Glu Lys Val Cys Lys Lys Leu Val Glu Lys Ile Lys
        755                 760                 765

Arg Lys Cys Pro Thr Leu Glu Asn Glu Leu Asn Glu Glu Lys Asp Glu
    770                 775                 780

Leu Lys Lys Lys Lys Asp Glu Tyr Glu Lys Val Lys Gln Glu Ser Glu
785                 790                 795                 800

Lys Phe Ala Lys Glu Ala Lys Leu Leu Leu Ser Ile Pro Glu Gln Asp
                805                 810                 815

Gly Gln Gly Gly Gly Ser Lys Val Gln Asp Gly Asn Ala Pro Lys Ser
            820                 825                 830

Val Gly Pro Pro Val Gln Pro Pro Ala Pro Ala Gln Pro Thr Pro Gly
        835                 840                 845

Gly Ala Pro Ala Ala Pro Ala Ala Pro Gly Gly Ser Thr Pro Ser Gly
    850                 855                 860

Thr Thr Asn Thr Ser Asn Val Ile Leu Val Arg Arg Thr Phe Val Ser
865                 870                 875                 880

Gly Glu Val Ser Glu Pro Glu Lys Lys Ala Phe Val Ala Thr Ala Arg
                885                 890                 895

Thr Leu Glu Leu Tyr Leu Glu Leu Lys Glu Lys Cys Lys Gly Leu Lys
            900                 905                 910

Gly Asp Cys Gly Phe Arg Lys Asp Cys Pro Gly Cys Glu Ala Ala Cys
        915                 920                 925

Thr Glu Ile Asp Lys Leu Cys Glu Gly Ile Lys Gly Leu Lys Val Thr
    930                 935                 940

Pro His His Thr Val Thr Leu Met Thr Ile Gln Ile Thr Thr Thr Thr
945                 950                 955                 960

Met Ile Thr Thr Thr Thr Thr Thr Thr Ile Thr Thr Thr Thr Thr Ala
                965                 970                 975
```

Thr Lys Ser Ile His Gly Gly Lys Val Thr Glu Gln Cys Ala Phe Ser
980 985 990

Gln Thr Thr Glu Ile Trp Leu Leu Arg Thr Cys Leu His Thr Ser Thr
995 1000 1005

Leu Thr Ser Thr Ser Thr Val Thr Ser Thr Val Thr Leu Thr Ser
1010 1015 1020

Met Arg Lys Cys Lys Pro Thr Arg Cys Thr Ser Asp Ser Ser Lys
1025 1030 1035

Glu Thr Glu Thr Gln Lys Glu Glu Glu Lys Glu Glu Lys Ala Lys
1040 1045 1050

Gln Asn Glu Gly Met Lys Met Arg Val Pro Glu Ile Val Lys Ile
1055 1060 1065

Ile Leu Leu Gly Val Met Ser Tyr Ala Thr Gln Gly Gln Ala Met
1070 1075 1080

Gly Arg Gly Ser Arg Pro Glu Arg Gly Gly Asp Gly Thr Ala Gly
1085 1090 1095

<210> SEQ ID NO 63
<211> LENGTH: 260
<212> TYPE: PRT
<213> ORGANISM: Pneumocystis murina
<220> FEATURE:
<221> NAME/KEY: MISC_FEATURE
<222> LOCATION: (1)..(260)
<223> OTHER INFORMATION: P. murina major surface glycoprotein PNEG_00564

<400> SEQUENCE: 63

Met Tyr Asp Tyr Phe Glu Arg Ile Ile Ser Arg Ser Thr Phe Asp Ser
1 5 10 15

Pro Ser His Met Leu Leu Arg Asp Lys Arg Trp Val Glu Glu Val Ala
20 25 30

Gln Lys Glu Ala Ala Met Ala Gln Pro Val Lys Arg Gln Ala Ala Gly
35 40 45

Gln Ala Ala Gly Asn Asp Glu Ile Lys Glu Glu Gln Val Leu Gly Leu
50 55 60

Ile Val Lys Ser Asp Tyr Ser Asp Lys Asp Lys Cys Lys Lys Lys Leu
65 70 75 80

Glu Glu Tyr Cys Ala Glu Leu Lys Lys Ile Asp Gly Glu Leu Lys Asn
85 90 95

Val Asp Val Lys Val Lys Gly Leu Cys Glu Asn Lys Asp Lys Lys Cys
100 105 110

Gly Asp Leu Lys Asn Lys Val Asp Lys Glu Leu Thr Asp Phe Lys Lys
115 120 125

Glu Val Glu Glu Ala Leu Asn Asp Ile Thr Asp Glu Asn Cys Arg Lys
130 135 140

Cys Glu Glu Lys Cys Val Leu Leu Glu Glu Ala Asp Pro Ser Asn Leu
145 150 155 160

Glu Glu Lys Cys Val Lys Leu Arg Asp Arg Cys Tyr Arg Gln Arg Arg
165 170 175

Gln Gly Val Ala Lys Glu Ile Leu Leu Arg Ala Leu Lys Glu Lys Val
180 185 190

Asn Asn Lys Asp Glu Cys Lys Lys Arg Met Lys Glu Ile Cys Gln Gly
195 200 205

Leu Ser Glu Tyr Ser Asp Glu Leu Val Phe Leu Cys Phe Asn Ser Asp
210 215 220

-continued

```
Lys Thr Cys Glu Tyr Leu Lys Gly Ser His Gln Asp Ser Cys Lys Pro
225                 230                 235                 240

Leu Glu Thr Glu Leu Glu Asp Lys Glu Leu Val Glu Lys Cys Gln Glu
                245                 250                 255

Tyr Leu Glu Lys
            260


<210> SEQ ID NO 64
<211> LENGTH: 136
<212> TYPE: PRT
<213> ORGANISM: Pneumocystis murina
<220> FEATURE:
<221> NAME/KEY: MISC_FEATURE
<223> OTHER INFORMATION: P. murina major surface glycoprotein
      PNEG_00674

<400> SEQUENCE: 64

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Thr
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Ile Gly Ala Leu Gln Glu Ala
                85                  90                  95

Val Glu Ala Tyr Leu Val Ser Leu Phe Glu Asp Thr Asn Leu Cys Ala
            100                 105                 110

Ile His Gly Lys Arg Val Thr Ile Gln Pro Lys Asp Met Gln Leu Ala
        115                 120                 125

Arg Arg Leu Arg Gly Glu Arg Ser
    130                 135


<210> SEQ ID NO 65
<211> LENGTH: 1146
<212> TYPE: PRT
<213> ORGANISM: Pneumocystis murina
<220> FEATURE:
<221> NAME/KEY: MISC_FEATURE
<222> LOCATION: (1)..(1146)
<223> OTHER INFORMATION: P. murina major surface glycoprotein PNEG_00053

<400> SEQUENCE: 65

Met Pro Leu Arg Asp Lys Arg Trp Val Glu Glu Val Ala Gln Lys Glu
1               5                   10                  15

Ala Ala Met Ala Gln Pro Val Lys Arg Gln Ala Ala Gly Gln Ala Ala
            20                  25                  30

Gly Asn Asp Glu Ile Lys Glu Glu Gln Val Leu Gly Leu Ile Val Lys
        35                  40                  45

Lys Glu Tyr Glu Asp Asn Ala Lys Cys Lys Lys Lys Leu Glu Glu Tyr
    50                  55                  60

Cys Ala Glu Leu Lys Lys Ile Asp Gly Lys Leu Glu Asn Val Asp Ala
65                  70                  75                  80

Lys Val Lys Gly Leu Cys Glu Asp Gly Lys Gln Gly Glu Lys Cys Lys
                85                  90                  95

Asn Leu Lys Asp Lys Val Lys Lys Glu Leu Asp Asp Phe Lys Thr Glu
```

-continued

```
            100                 105                 110

Leu Glu Lys Thr Leu Asn Asp Ile Thr Asp Glu Asn Cys Arg Lys Cys
        115                 120                 125

Glu Glu Lys Cys Val Leu Leu Glu Glu Ala Asp Pro Ser Asn Leu Glu
    130                 135                 140

Glu Lys Cys Val Lys Leu Arg Asp Arg Cys Tyr Gly Gln Arg Arg Gln
145                 150                 155                 160

Glu Val Thr Lys Glu Ile Leu Leu Arg Ala Leu Lys Glu Lys Val Asn
                165                 170                 175

Asp Thr Asn Glu Cys Lys Lys Arg Met Lys Glu Ile Cys Gln Gly Leu
            180                 185                 190

Ser Glu Tyr Ser Asp Glu Leu Val Leu Ile Cys Phe Asn Ser Asp Lys
        195                 200                 205

Thr Cys Lys Tyr Leu Lys Asn Thr His Val Asp Ser Cys Lys Pro Leu
    210                 215                 220

Glu Thr Glu Leu Glu Asp Lys Glu Leu Val Glu Lys Cys Gln Glu Tyr
225                 230                 235                 240

Leu Glu Lys Cys Tyr Phe Tyr Gly Ser Ser Cys Lys Asn Thr Lys Cys
                245                 250                 255

Asp Lys Val Lys Asn Lys Cys Lys Gly Lys Gly Ile Glu Tyr Glu Gly
            260                 265                 270

Pro Lys Leu Asp Phe Ser Pro Val Lys Glu Lys Pro Arg Phe Pro Glu
        275                 280                 285

Lys Ile Glu Val Glu Asn Leu Tyr Lys Arg Leu Gly Ala Lys Gly Ile
    290                 295                 300

Ile Val Gly Lys Pro Lys Tyr Lys Thr Leu Gln Asp Leu Thr Leu Leu
305                 310                 315                 320

Leu Ile Lys Gly Arg Asn Gly Lys Asp Glu Gly Glu Lys Cys Lys Glu
                325                 330                 335

Ala Leu Lys Asp Cys Glu Ser Phe Lys His Leu Asp Tyr Glu Leu Glu
            340                 345                 350

Gln Leu Cys Glu Asp Lys Asp Lys Asp Asn Lys Cys Lys Glu Leu Val
        355                 360                 365

Glu Val Glu Asp Arg Cys Thr Asn Leu Lys Leu Glu Leu Tyr Leu Lys
    370                 375                 380

Gly Leu Ser Thr Glu Phe Glu Glu Ser Asn Glu Ser Lys Tyr Val Ser
385                 390                 395                 400

Trp Glu Tyr Val Pro Lys Ser Val Thr Lys Glu Asp Cys Arg Lys Phe
                405                 410                 415

Glu Ser Glu Cys Phe His Leu Glu Gly Val Cys Thr Asn Glu Ile Gly
            420                 425                 430

Lys Ala Cys Glu Asn Val Arg Val Ala Cys Tyr Lys Lys Gly Gln Asp
        435                 440                 445

Arg Met Leu Asn Arg Tyr Phe Gln Glu Gly Leu Lys Gly Leu Ile Gly
    450                 455                 460

Asp Leu Glu Leu Ala Thr Glu Asn Leu Glu Lys Cys Gln Lys Ser Val
465                 470                 475                 480

Val Gly Asn Tyr Thr Lys Leu Lys Lys Asp Arg Arg Tyr Phe Ala Lys
                485                 490                 495

Cys His Arg Pro Thr Lys Leu Cys Tyr Glu Leu Leu Asp Asp Val Ile
            500                 505                 510

Leu Gln Ser Glu Glu Leu Glu Val Val Leu Asn Leu Arg Arg Asp Phe
        515                 520                 525
```

```
Pro Ser Lys Glu Asp Cys Val Glu Leu Lys Lys Lys Cys Glu Asp Leu
    530                 535                 540

Glu Ser Asp Ser Tyr Leu Asn His Glu Lys Cys Asp Thr Leu Asn Arg
545                 550                 555                 560

Arg Cys Glu Tyr Leu Lys Val Thr Glu Glu Leu Lys Lys Arg Leu Leu
                565                 570                 575

Lys Arg Gly Asp Asp Ala Leu Arg Thr Gln Gly Asn Cys Thr Ala Val
            580                 585                 590

Leu Lys Lys Glu Cys Glu Glu Leu Ser Arg Arg Gly Lys Glu Asp Phe
        595                 600                 605

Ser Val Ser Cys Ala Leu Arg Glu Glu Thr Cys Ser Phe Met Val Glu
    610                 615                 620

Gln Thr Glu Asn Glu Cys Leu Phe Leu Lys Asn Asn Met Asp Ile Gly
625                 630                 635                 640

Lys Ile Ile Glu Lys Ile Glu Asn Gly Lys Arg Asn Glu Thr Leu Val
                645                 650                 655

Glu Glu Leu Cys Thr Leu Phe Asp Pro Tyr Cys His Gln Tyr Ile Glu
            660                 665                 670

Asn Cys Pro Asp Arg Leu Lys Lys Thr Asn Asn Ala Gly Arg Lys Gly
        675                 680                 685

Val Cys Leu Glu Leu Glu Glu Lys Cys Lys Pro Phe Phe Glu Lys Leu
    690                 695                 700

Lys Leu Glu Asn Glu Leu Thr His Lys Leu Lys Gly Ser Leu Ser Asp
705                 710                 715                 720

Glu Thr Lys Cys Lys Glu Thr Leu Gly Lys His Cys Thr Glu Trp Lys
                725                 730                 735

Lys Glu Gly Asn Gln Thr Leu Asn Ser Leu Cys Glu Asp Ala Lys Lys
            740                 745                 750

Glu Glu Leu Cys Lys Lys Leu Val Lys Lys Val Lys Glu Lys Cys Pro
        755                 760                 765

Thr Leu Lys Asn Lys Leu Asp Asn Glu Lys Asp Glu Leu Glu Lys Lys
    770                 775                 780

Lys Asp Glu Tyr Glu Lys Ala Lys Gln Glu Ser Glu Lys Phe Ala Lys
785                 790                 795                 800

Glu Ala Lys Leu Val Leu Ser Arg Pro Glu Gln Asp Gly Gln Gly Gly
                805                 810                 815

Gly Ser Lys Ala Gln Asp Gly Ser Val Pro Lys Pro Val Gly Pro Pro
            820                 825                 830

Val Gln Pro Pro Ala Pro Ala Gln Pro Thr Pro Gly Gly Val Pro Ala
        835                 840                 845

Pro Thr Leu Ala Pro Pro Ala Gln Pro Thr Ser Gly Gly Ala Pro Leu
    850                 855                 860

Pro Val Pro Pro Ala Ala Pro Ala Ala Pro Gly Ala Pro Ser Thr Pro
865                 870                 875                 880

Gly Thr Pro Ala Ala Pro Ala Gly Pro Ala Ala Pro Gly Thr Pro Ser
                885                 890                 895

Thr Pro Ser Thr Pro Pro Ala Gly Pro Ala Gly Pro Ser Gly Gly Thr
            900                 905                 910

Pro Gly Ala Pro Ala Gly Pro Pro Ala Pro Gly Gly Ser Thr Pro Ser
        915                 920                 925

Gly Thr Thr Asn Thr Ser Asn Val Ile Leu Val Arg Arg Thr Phe Val
    930                 935                 940
```

Ser Gly Glu Val Ser Gln Pro Glu Lys Lys Ala Phe Val Ala Thr Ala
945 950 955 960

Arg Ala Leu Glu Leu Tyr Leu Glu Leu Lys Glu Lys Cys Lys Gly Leu
965 970 975

Lys Gly Asp Cys Glu Phe Arg Lys Asp Cys Pro Lys Cys Glu Thr Val
980 985 990

Cys Lys Glu Ile Asp Glu Leu Cys Glu Gly Ile Glu Gly Leu Lys Val
995 1000 1005

Thr Pro His His Thr Val Thr Ser Thr Ala Thr Gln Thr Thr Thr
1010 1015 1020

Thr Thr Ala Thr Thr Thr Thr Thr Thr Thr Thr Thr Thr Thr Thr
1025 1030 1035

Thr Thr Thr Thr Thr Thr Thr Ala Thr Thr Thr Glu Ser Val Asp
1040 1045 1050

Gly Gly Lys Val Thr Glu Glu Cys Thr Leu Val Gln Thr Thr Asp
1055 1060 1065

Thr Trp Val Thr Ser Thr Ser Leu His Thr Ser Thr Leu Thr Ser
1070 1075 1080

Thr Ser Thr Val Thr Ser Thr Val Thr Leu Thr Ser Met Arg Lys
1085 1090 1095

Cys Lys Pro Thr Arg Cys Thr Ser Asp Ser Ser Lys Glu Thr Glu
1100 1105 1110

Thr Gln Lys Glu Glu Glu Lys Glu Glu Glu Val Lys Pro Asn Glu
1115 1120 1125

Gly Met Lys Ile Arg Val Pro Glu Met Ile Lys Ile Met Leu Leu
1130 1135 1140

Gly Val Ile
1145

<210> SEQ ID NO 66
<211> LENGTH: 920
<212> TYPE: PRT
<213> ORGANISM: Pneumocystis murina
<220> FEATURE:
<221> NAME/KEY: MISC_FEATURE
<222> LOCATION: (1)..(920)
<223> OTHER INFORMATION: P. murina major surface glycoprotein-like
PNEG_02613

<400> SEQUENCE: 66

Met Thr Ala Gln Leu Val Lys Arg Gln Ala Ala Gly Gln Ala Glu Gly
1 5 10 15

Asn Asp Glu Ile Lys Glu Glu Gln Val Leu Gly Leu Ile Val Lys Lys
20 25 30

Glu Tyr Asn Asn Asp Ala Lys Cys Lys Lys Lys Leu Glu Glu Tyr Cys
35 40 45

Ala Glu Leu Lys Lys Ile Asn Gly Lys Leu Glu Asn Val Asp Ala Lys
50 55 60

Val Lys Gly Leu Phe Glu Lys Glu Ser Lys Asp Leu Lys Lys Glu Leu
65 70 75 80

Leu Glu Ala Phe Lys Asn Ile Lys Asp Glu Asn Cys Arg Lys Tyr Glu
85 90 95

Asp Lys Cys Ile Phe Leu Glu Glu Ala Asp Pro Ile Asn Leu Lys Glu
100 105 110

Asn Cys Val Lys Leu Ile Asn Lys Cys Ser Lys Arg Lys Arg Gln Asp
115 120 125

-continued

```
Phe Val Tyr Gly Ile Phe Tyr Asn Thr Phe Val Phe Lys Ser Ser Val
    130                 135                 140

Glu Asp Val Cys Thr Arg Leu Asp Arg Ile Leu Asn Glu Asn Glu Leu
145                 150                 155                 160

Lys Glu Lys Cys Gln Glu Tyr Phe Glu Asn Cys Tyr Phe Tyr Lys Ser
                165                 170                 175

Asn Cys Arg Ser Thr Lys Tyr Phe Asp Pro Leu Glu Ile Lys Ala Thr
            180                 185                 190

Leu Asp Arg Ile Ile Leu Glu Lys Ile Tyr Glu Lys Ala Glu Val Lys
        195                 200                 205

Glu Ile Ile Thr Gly Lys Leu Gln Glu Lys Ser Leu Glu Asn Thr Ile
    210                 215                 220

Leu Leu Trp Ser Arg Glu Asn Asn Ser Lys Asn Leu Gln Glu Ile Cys
225                 230                 235                 240

Lys Asn Ile Leu Asn Asp Cys Asn Phe Leu Tyr Met Asn Tyr Asn Leu
                245                 250                 255

Lys Ala Leu Cys Lys Glu Ala Ser Lys Asn Ile Asp Ser Arg Cys Lys
            260                 265                 270

Glu Leu Val Lys Val Glu Thr Arg Cys Thr Asn Leu Lys Leu Glu Leu
        275                 280                 285

Tyr Ile Lys Gly Phe Ser Thr Glu Phe Glu Lys Asn Lys Asp Ser Lys
    290                 295                 300

Tyr Phe Ser Trp Glu Gln Val Pro Lys Leu Pro Ser Lys Glu Asp Cys
305                 310                 315                 320

Ile Lys Leu Glu Ser Glu Cys Phe Tyr Leu Glu Asn Val Cys Thr Asn
                325                 330                 335

Lys Ile Asp Lys Ala Cys Glu Asn Leu Arg Ile Ala Tyr Tyr Arg Lys
            340                 345                 350

Gly Gln Asn Leu Ala Phe Asn Lys Leu Ile Arg Asn Gln Phe Ile Arg
        355                 360                 365

Leu Met Val Lys Asn Cys Ile Lys Phe Lys Glu Asp Lys Arg Tyr Leu
    370                 375                 380

Leu Lys Cys Leu Gln Pro Thr Lys Leu Cys Tyr Glu Phe Leu Glu Asp
385                 390                 395                 400

Ile Ile Asp Gln Ser Lys Glu Phe Glu Ala Leu Leu Asp Ser Lys Lys
                405                 410                 415

Glu Phe Pro Lys Glu Ile Leu Asn Thr Asn Cys Gly Tyr Leu Glu Thr
            420                 425                 430

Arg Lys Lys Phe Lys Lys Ile Phe Leu Glu Lys Lys Asp Asn Ser Leu
        435                 440                 445

Lys Thr Arg Glu Asn Cys Ile Lys Ala Val Lys Glu Glu Cys Glu Arg
    450                 455                 460

Leu Ser Arg Arg Lys Lys Asn Pro Phe Val Thr Phe Cys Ala Leu Pro
465                 470                 475                 480

Glu Glu Thr Cys Asn Phe Ile Val Lys Glu Val Ile Asp Glu Cys Tyr
                485                 490                 495

Asn Leu Ala Tyr Asn Met Asn Asp Arg Asn Ile Ile Asn Lys Ile Glu
            500                 505                 510

Lys Thr Asn Lys Ala Leu Thr Lys Glu Ile Cys Met Phe Trp Asp Pro
        515                 520                 525

Tyr Cys His Gln Tyr Ile Glu Asn Cys Pro Glu Ile Leu Lys Gln Glu
    530                 535                 540

Asn Ile Asn Thr Lys Arg Ala His Cys Leu Lys Leu Gln Arg Tyr Cys
```

-continued

```
545                 550                 555                 560

Thr Pro Leu Trp Glu Asn Leu Arg Leu Glu Gly Glu Leu Ile His Glu
                565                 570                 575

Leu Lys Ser Ser Leu Ile Asn Asp Thr Ile Cys Lys Glu Thr Leu Glu
            580                 585                 590

Lys Tyr Tyr Thr Lys Trp Lys Ser Glu Lys Asn Gln Thr Phe Asp Asn
        595                 600                 605

Ala Ser Glu Asp Lys Asn Gly Ser Ser Glu His Leu Arg Arg Asn Val
    610                 615                 620

Cys Lys Lys Leu Ile Glu Lys Val Lys Arg Lys Cys Ser Thr Leu Lys
625                 630                 635                 640

Asn Glu Leu Asp Lys Glu Lys Asp Glu Leu Lys Glu Lys Asn Glu Tyr
                645                 650                 655

Glu Lys Val Lys Lys Glu Ala Glu Asn Phe Met Lys Val Thr Asn Leu
            660                 665                 670

Leu Leu Ser Lys Pro Lys Lys Asn Glu Asn Gly Gln Ser Ala Thr Leu
        675                 680                 685

Ser Val Gln Asn Asn Ser Val Leu Ala Pro Val Ala Pro Ser Thr Ala
    690                 695                 700

Pro Pro Thr Ala Ala Glu Ser Ala Ser Ser Gln Gly Gly Thr Glu His
705                 710                 715                 720

Thr Thr Glu Gln Arg Leu Ile Leu Arg Arg Phe Val Asp Glu Gly Val
                725                 730                 735

Ser Lys Thr Glu Thr Asn Ala Phe Asp Leu Met Thr Arg Ala Leu Lys
            740                 745                 750

Leu Tyr Leu Gly Met Lys Glu Asp Cys Lys Thr Leu Gln Val Asn Cys
        755                 760                 765

Gly Phe Arg Glu Asn Cys Leu Asn Phe Gly Thr Val Cys Glu Asp Ile
    770                 775                 780

Asp Lys Leu Cys Asn Val Lys Pro Leu Glu Val Ile Pro His His Thr
785                 790                 795                 800

Leu Ile Leu Thr Thr Ile Ser Thr Thr Thr Arg Thr Ala Thr Met Pro
                805                 810                 815

Asn Asn Ser Asp Ile Asp Asp Asn Val Thr Thr Ser Ile Lys Glu Ala
            820                 825                 830

Ala Thr Glu Gln Cys Thr Leu Ile Arg Thr Ile Asn Thr Ser Val Ile
        835                 840                 845

Asp Thr Ser Leu His Thr Ser Thr Met Thr Ser Thr Ser Ala Val Thr
    850                 855                 860

Ser Thr Val Thr Leu Thr Ser Met Gln Glu Cys Lys Pro Thr Arg Cys
865                 870                 875                 880

Thr Thr Asp Ser Ser Arg Lys Thr Lys Met Arg Gly Lys Leu Ile Ser
                885                 890                 895

Gly Gln Gly Met Lys Met Arg Val Pro Lys Met Ile Lys Ile Met Leu
            900                 905                 910

Gly Val Ile Val Met Arg Met Leu
        915                 920


<210> SEQ ID NO 67
<211> LENGTH: 619
<212> TYPE: PRT
<213> ORGANISM: Pneumocystis murina
<220> FEATURE:
<221> NAME/KEY: MISC_FEATURE
<222> LOCATION: (1)..(619)
```

<223> OTHER INFORMATION: P. murina major surface glycoprotein PNEG_02990

<400> SEQUENCE: 67

```
Met Tyr Gly Tyr Phe Glu Arg Ile Ile Ser Arg Ser Thr Phe Asp Leu
1               5                   10                  15

Pro Ser His Met Leu Leu Arg Asp Lys Arg Trp Val Glu Glu Val Ala
            20                  25                  30

Gln Lys Glu Ala Ala Lys Ala Gln Pro Val Lys Arg Gln Ala Ala Gly
        35                  40                  45

Gln Ala Ala Gly Gln Ala Ala Gly Asn Asp Glu Ile Lys Glu Glu Gln
    50                  55                  60

Val Leu Gly Leu Ile Val Lys Ser Asp Tyr Ser Asp Lys Asp Lys Cys
65                  70                  75                  80

Lys Lys Lys Leu Glu Glu Tyr Cys Glu Glu Leu Lys Lys Ile Asp Lys
                85                  90                  95

Lys Leu Glu Asn Val Asp Asp Lys Val Lys Gly Leu Cys Glu Asn Ile
            100                 105                 110

Asp Lys Lys Cys Gly Asp Leu Lys Asp Lys Val Glu Lys Glu Leu Asn
        115                 120                 125

Ser Phe Lys Thr Glu Val Asp Glu Ala Leu Lys Gly Pro Thr Asp Glu
    130                 135                 140

Lys Cys Arg Lys Cys Glu Glu Lys Cys Val Leu Leu Glu Glu Ala Asp
145                 150                 155                 160

Pro Ser Asn Leu Glu Glu Lys Cys Val Lys Leu Arg Asp Arg Cys Tyr
                165                 170                 175

Gly Gln Arg Arg Gln Glu Val Thr Lys Glu Ile Phe Leu Arg Ala Leu
            180                 185                 190

Glu Gly Lys Val Asn Asp Thr Asp Glu Cys Lys Lys Lys Met Lys Glu
        195                 200                 205

Ile Cys Gln Gly Leu Ser Glu Tyr Ser Asp Glu Leu Ile Phe Ser Cys
    210                 215                 220

Phe Asn Ser Asp Lys Ala Cys Asn Gly Leu Lys Val Ser Tyr Leu Asp
225                 230                 235                 240

Ser Cys Lys Pro Leu Glu Thr Glu Leu Lys Asp Asn Glu Leu Val Glu
                245                 250                 255

Lys Cys Gln Glu Tyr Leu Glu Lys Cys Tyr Phe Tyr Gly Ser Ser Cys
            260                 265                 270

Ser Asn Ser Lys Cys Lys Glu Ser Lys Glu Lys Cys Gly Lys Lys Gly
        275                 280                 285

Ile Val Tyr Glu Gly Pro Lys Leu Asp Phe Ser Pro Val Arg Glu Lys
    290                 295                 300

Pro Arg Phe Pro Glu Lys Ile Glu Val Glu Asn Leu Tyr Lys Arg Leu
305                 310                 315                 320

Gly Ala Lys Gly Ile Ile Val Gly Arg Pro Lys Tyr Lys Thr Leu Gln
                325                 330                 335

Asp Leu Ile Leu Leu Leu Ile Lys Glu Arg Asn Glu Lys Asp Asp Lys
            340                 345                 350

Glu Lys Cys Lys Gly Ala Leu Lys Gly Cys Glu Ser Phe Lys His Leu
        355                 360                 365

Asp Tyr Arg Leu Gly Glu Leu Cys Glu Asp Lys Asp Lys Asp Lys Lys
    370                 375                 380

Cys Glu Glu Leu Val Asp Val Glu Asp Arg Cys Thr Asn Phe Lys Leu
385                 390                 395                 400
```

```
Glu Leu Tyr Leu Lys Gly Leu Ser Thr Glu Phe Glu Lys Asn Lys Glu
                405                 410                 415

Ser Asp Tyr Phe Ser Trp Glu His Val Ser Lys Leu Val Thr Lys Glu
            420                 425                 430

Asp Cys Arg Lys Phe Glu Ser Glu Cys Phe His Leu Lys Ser Val Cys
        435                 440                 445

Thr Asn Lys Val Glu Lys Ala Cys Glu Asn Ala Arg Val Ala Cys Tyr
    450                 455                 460

Lys Lys Gly Gln Asp Arg Ile Leu Asn Arg Tyr Phe Gln Glu Glu Leu
465                 470                 475                 480

Lys Gly Leu Ile Gly Asp Leu Glu Leu Val Asp Glu Asn Leu Glu Lys
                485                 490                 495

Cys Gln Lys Ser Val Val Gly Asn Tyr Lys Lys Leu Lys Glu Asp Lys
            500                 505                 510

Arg Tyr Phe Glu Lys Cys His Arg Pro Thr Glu Leu Cys Tyr Lys Leu
        515                 520                 525

Leu Asp Asp Val Ile Phe Gln Ser Glu Glu Leu Glu Ile Val Leu Asn
    530                 535                 540

Leu Arg Arg Asp Phe Pro Ser Lys Glu Asp Cys Val Glu Leu Lys Lys
545                 550                 555                 560

Lys Cys Glu Asp Leu Glu Ser Asp Ser Tyr Leu Asn His Glu Lys Cys
                565                 570                 575

Asp Thr Leu Asn Arg Arg Cys Glu Tyr Leu Lys Val Thr Glu Glu Leu
            580                 585                 590

Arg Lys Arg Leu Leu Lys Arg Gly Asp Asp Ala Leu Arg Thr Gln Gly
        595                 600                 605

Asn Cys Thr Ala Val Leu Lys Lys Glu Cys Glu
    610                 615
```

<210> SEQ ID NO 68
<211> LENGTH: 1262
<212> TYPE: PRT
<213> ORGANISM: Pneumocystis murina
<220> FEATURE:
<221> NAME/KEY: MISC_FEATURE
<222> LOCATION: (1)..(1262)
<223> OTHER INFORMATION: P. murina major surface glycoprotein PNEG_035998

<400> SEQUENCE: 68

```
Met Lys Glu Ile Glu Gln Cys Thr Phe Thr Arg Thr Thr Asp Thr Trp
1               5                   10                  15

Val Thr Ser Thr Ser Leu His Thr Ser Thr Met Thr Ser Thr Ser Thr
            20                  25                  30

Val Thr Ser Thr Val Thr Leu Thr Ser Met Arg Lys Cys Lys Pro Thr
        35                  40                  45

Arg Cys Thr Ser Asp Ser Ser Lys Glu Thr Glu Thr Gln Lys Glu Glu
    50                  55                  60

Glu Lys Glu Glu Glu Val Lys Pro Asn Glu Gly Met Lys Ile Arg Val
65                  70                  75                  80

Pro Glu Ile Val Lys Ile Met Leu Leu Gly Val Met Gly Lys Val Gln
                85                  90                  95

Ala Tyr His Lys Arg Leu Ser Lys Cys Met Leu Ile Leu Lys Glu Leu
            100                 105                 110

Ala Asn Leu Tyr Leu Ser Ser Lys Ile Ile Ser Gly Ser Ile Phe His
        115                 120                 125
```

-continued

```
Ser Pro Thr Tyr Met Pro Leu Arg Asp Lys Arg Trp Val Glu Glu Val
    130                 135                 140

Ala Gln Lys Glu Ala Ala Met Ala Gln Pro Val Lys Arg Gln Ala Ala
145                 150                 155                 160

Gly Gln Ala Ala Gly Asn Asp Glu Ile Lys Glu Glu Gln Val Leu Gly
                165                 170                 175

Leu Ile Val Lys Ser Tyr Tyr Ser Asp Asp Asn Lys Cys Lys Ala Asn
            180                 185                 190

Leu Lys Gln Tyr Cys Glu Glu Leu Lys Lys Ile Asp Gly Lys Leu Glu
        195                 200                 205

Ser Val Asp Val Lys Val Lys Gly Leu Cys Glu Asn Gly Lys Glu Gly
    210                 215                 220

Glu Lys Cys Lys Glu Leu Lys Lys Lys Leu Glu Thr Glu Leu Gly Ala
225                 230                 235                 240

Phe Lys Thr Glu Val Glu Asn Ala Leu Asn Asn Leu Thr Asp Glu Lys
                245                 250                 255

Cys Arg Lys Tyr Glu Glu Lys Cys Leu Leu Leu Glu Glu Ala Asp Pro
            260                 265                 270

Asn Asn Leu Glu Glu Lys Cys Val Lys Leu Arg Asp Arg Cys Tyr Arg
        275                 280                 285

Gln Arg Arg Gln Gly Val Ala Lys Glu Ile Leu Leu Arg Ala Leu Glu
    290                 295                 300

Gly Lys Val Asn Asn Lys Asp Glu Cys Lys Lys Arg Met Lys Glu Ile
305                 310                 315                 320

Cys Gln Gly Leu Ser Glu Tyr Ser Asp Glu Leu Val Phe Ser Cys Phe
                325                 330                 335

Asn Ser Asp Lys Thr Cys Glu Tyr Leu Gln Lys Asn His Gly Asp Ser
            340                 345                 350

Cys Lys Pro Leu Glu Lys Glu Leu Glu Asp Lys Glu Leu Val Glu Lys
        355                 360                 365

Cys Gln Glu Tyr Leu Glu Lys Cys Tyr Phe Tyr Gly Ser Ser Cys Ser
    370                 375                 380

Asn Ser Lys Cys Asp Lys Val Lys Asn Lys Cys Lys Glu Lys Gly Ile
385                 390                 395                 400

Glu Tyr Glu Gly Pro Lys Leu Asp Phe Ser Pro Val Lys Glu Lys Pro
                405                 410                 415

Arg Phe Pro Glu Lys Ile Glu Val Glu Asn Leu Tyr Lys Lys Glu Glu
            420                 425                 430

Ala Lys Gly Ile Ile Val Gly Lys Pro Lys Tyr Lys Thr Leu Arg Asp
        435                 440                 445

Leu Ala Leu Leu Leu Ile Lys Glu Arg Asn Gly Lys Asp Glu Gly Glu
    450                 455                 460

Lys Cys Lys Glu Ala Leu Lys Asp Cys Glu Ser Phe Lys His Leu Asp
465                 470                 475                 480

Tyr Gly Leu Glu Glu Leu Cys Gly Asp Lys Asp Lys Glu Asp Arg Cys
                485                 490                 495

Lys Glu Leu Val Glu Val Glu Asp Arg Cys Thr Asn Phe Lys Leu Glu
            500                 505                 510

Leu Tyr Leu Lys Gly Leu Ser Thr Glu Phe Glu Lys Asp Lys Glu Ser
        515                 520                 525

Asp Tyr Phe Ser Trp Gly Gln Val Ser Lys Leu Val Ser Arg Glu Asp
    530                 535                 540

Cys Ile Lys Phe Glu Ser Glu Cys Phe His Leu Glu Gly Val Cys Thr
```

```
545                 550                 555                 560

Asn Lys Ile Gly Lys Ala Cys Glu Asn Val Arg Val Ala Cys Tyr Lys
                565                 570                 575

Lys Gly Gln Asp Arg Val Leu Asn Arg Tyr Phe Gln Glu Gly Leu Lys
            580                 585                 590

Gly Leu Ile Gly Asp Leu Glu Leu Val Thr Glu Asn Leu Glu Lys Cys
        595                 600                 605

Gln Lys Ser Val Val Gly Asn Tyr Thr Lys Leu Lys Glu Asp Arg Arg
    610                 615                 620

Tyr Phe Thr Lys Cys His Leu Pro Thr Lys Leu Cys Tyr Glu Leu Leu
625                 630                 635                 640

Asp Asp Val Ile Leu Gln Ser Glu Glu Leu Glu Val Val Leu Asn Leu
                645                 650                 655

Arg Arg Asp Phe Pro Arg Lys Glu Asp Cys Val Glu Leu Lys Lys Lys
            660                 665                 670

Cys Lys Asp Leu Glu Ser Asp Ser Tyr Leu Asn His Glu Lys Cys Asp
        675                 680                 685

Thr Leu Asn Arg Arg Cys Glu Tyr Leu Lys Val Thr Glu Glu Leu Arg
    690                 695                 700

Lys Arg Leu Leu Lys Arg Gly Asp Asp Ala Leu Arg Thr Gln Gly Asn
705                 710                 715                 720

Cys Thr Ala Val Leu Lys Lys Glu Cys Glu Glu Leu Ser Arg Arg Gly
                725                 730                 735

Lys Glu Asp Phe Ser Val Ser Cys Ala Leu Arg Glu Glu Thr Cys Ser
            740                 745                 750

Phe Met Val Glu Gln Thr Glu Asn Glu Cys Leu Phe Leu Lys Asn Asn
        755                 760                 765

Ile Glu Asn Gly Lys Ile Leu Asn Lys Ile Glu Asn Gly Lys Gly Asn
    770                 775                 780

Glu Thr Leu Val Glu Glu Leu Cys Thr Leu Phe Asp Pro Tyr Cys His
785                 790                 795                 800

Gln Tyr Ile Glu Asn Cys Pro Asp Arg Leu Lys Lys Glu Lys Asn Ser
                805                 810                 815

Asn Lys Asn Gly Val Cys Leu Gln Leu Glu Glu Lys Cys Lys Pro Phe
            820                 825                 830

Phe Glu Lys Leu Lys Leu Glu Asn Glu Leu Thr His Lys Leu Lys Gly
        835                 840                 845

Ser Leu Ser Asp Glu Thr Lys Cys Lys Glu Thr Leu Gly Lys His Cys
    850                 855                 860

Thr Glu Trp Lys Lys Glu Gly Asn Gln Thr Leu Asn Ser Leu Cys Glu
865                 870                 875                 880

Asp Ala Lys Lys Glu Glu Leu Cys Lys Lys Leu Val Lys Lys Val Lys
                885                 890                 895

Glu Lys Cys Pro Thr Leu Lys Asn Lys Leu Asp Asn Glu Lys Asp Glu
            900                 905                 910

Leu Glu Lys Lys Lys Asp Glu Tyr Glu Lys Ala Lys Gln Glu Ser Glu
        915                 920                 925

Lys Phe Ala Lys Glu Ala Lys Leu Val Leu Ser Arg Pro Glu Gln Asp
    930                 935                 940

Gly Gln Gly Gly Gly Ser Lys Ala Gln Asp Gly Ser Val Pro Lys Pro
945                 950                 955                 960

Val Gly Pro Pro Val Gln Pro Pro Ala Pro Ala Gln Pro Thr Pro Gly
                965                 970                 975
```

-continued

```
Gly Val Pro Ala Pro Thr Leu Ala Pro Pro Ala Gln Pro Thr Ser Gly
            980                 985                 990

Gly Ala Pro Leu Pro Val Pro Pro  Ala Ala Pro Gly Gly  Thr Pro Gly
        995                 1000                1005

Gly Ala  Pro Val Pro Val Pro  Pro Pro Ala Pro Gly  Thr Pro Pro
    1010                 1015                 1020

Ala Gly  Pro Ala Gly Pro Ser  Gly Pro Ser Gly Gly  Thr Pro Ala
    1025                 1030                 1035

Gly Pro  Pro Ala Pro Gly Gly  Ser Thr Pro Ser Gly  Thr Thr Asn
    1040                 1045                 1050

Thr Ser  Asn Val Ile Leu Val  Arg Arg Thr Phe Val  Ser Gly Glu
    1055                 1060                 1065

Val Ser  Glu Pro Glu Lys Lys  Ala Phe Val Ala Thr  Ala Arg Ala
    1070                 1075                 1080

Leu Glu  Leu Tyr Leu Glu Leu  Lys Glu Lys Cys Lys  Gly Leu Lys
    1085                 1090                 1095

Gly Asp  Cys Glu Phe Arg Lys  Asp Cys Pro Lys Cys  Glu Ala Val
    1100                 1105                 1110

Cys Thr  Glu Ile Asp Lys Leu  Cys Glu Gly Ile Glu  Gly Leu Lys
    1115                 1120                 1125

Val Thr  Pro His His Thr Val  Ile Ser Thr Ala Thr  Gln Thr Thr
    1130                 1135                 1140

Thr Thr  Thr Ala Thr Thr Thr  Thr Thr Thr Thr Thr  Thr Thr Thr
    1145                 1150                 1155

Thr Thr  Thr Thr Thr Thr Thr  Thr Ala Thr Thr Thr  Glu Ser Val
    1160                 1165                 1170

Asp Gly  Gly Lys Val Thr Glu  Glu Cys Thr Leu Val  Gln Thr Thr
    1175                 1180                 1185

Asp Thr  Trp Val Thr Ser Thr  Ser Leu His Thr Ser  Thr Leu Thr
    1190                 1195                 1200

Ser Thr  Ser Thr Val Thr Ser  Thr Val Thr Leu Thr  Ser Met Arg
    1205                 1210                 1215

Lys Cys  Lys Pro Thr Arg Cys  Thr Ser Asp Ser Ser  Lys Glu Thr
    1220                 1225                 1230

Glu Thr  Gln Lys Glu Glu Glu  Lys Glu Glu Glu Val  Lys Pro Asn
    1235                 1240                 1245

Glu Gly  Met Lys Ile Arg Val  Pro Glu Met Ile Lys  Ile Met
    1250                 1255                 1260
```